US012473663B2

(12) United States Patent
Looney et al.

(10) Patent No.: US 12,473,663 B2

(45) Date of Patent: Nov. 18, 2025

(54) COMPOSITIONS AND METHODS FOR IMMUNE REPERTOIRESEQUENCING

(71) Applicant: Life Technologies Corporation, Carlsbad, CA (US)

(72) Inventors: Timothy Looney, Austin, TX (US); Chenchen Yang, Foster City, CA (US); Geoffrey Lowman, Carlsbad, CA (US)

(73) Assignee: Life Technologies Corporation, Carlsbad, CA (US)

(*) Notice: Subject to any disclaimer, the term of this patent is extended or adjusted under 35 U.S.C. 154(b) by 1256 days.

(21) Appl. No.: 17/250,406

(22) PCT Filed: Jul. 18, 2019

(86) PCT No.: PCT/US2019/042473

§ 371 (c)(1),
(2) Date: Jan. 18, 2021

(87) PCT Pub. No.: WO2020/018836

PCT Pub. Date: Jan. 23, 2020

(65) Prior Publication Data

US 2022/0073983 A1 Mar. 10, 2022

Related U.S. Application Data

(60) Provisional application No. 62/846,497, filed on May 10, 2019, provisional application No. 62/700,056, filed on Jul. 18, 2018.

(51) Int. Cl.

*C40B 50/06* (2006.01)
*C12N 15/10* (2006.01)

(52) U.S. Cl.

CPC .......... *C40B 50/06* (2013.01); *C12N 15/1093* (2013.01)

(58) Field of Classification Search

None

See application file for complete search history.

(56) References Cited

U.S. PATENT DOCUMENTS 7,785,783 B2 8/2010 Morley et al.
8,236,503 B2 8/2012 Faham et al.

(Continued)

FOREIGN PATENT DOCUMENTS

CN 102325903 A 1/2012
CN 105063032 A 11/2015

(Continued)

OTHER PUBLICATIONS

Benichou et al. ("Rep-Seq: uncovering the immunological repertoire through next-generation sequencing") (Immunology, 135, 183-191).*

(Continued)

*Primary Examiner* — Christian C Boesen

(74) *Attorney, Agent, or Firm* — Klarquist Sparkman, LLP

(57) ABSTRACT

The present disclosure provides methods, compositions, kits, and systems useful in the determination and evaluation of the immune repertoire. In one aspect, target-specific primer panels provide for the effective amplification of nucleic acid sequences of murine T cell receptor and/or B cell receptor chains with improved sequencing accuracy and resolution over the repertoire. Variable regions associated with the immune cell receptor are resolved to effectively portray clonal diversity of a biological sample and/or differences associated with the immune cell repertoire of a biological sample.

15 Claims, 2 Drawing Sheets

Specification includes a Sequence Listing.

(56) References Cited

U.S. PATENT DOCUMENTS

| | | | | |
|---|---|---|---|---|
| 8,883,418 | B2 | 11/2014 | Pasqual et al. | |
| 9,068,224 | B2 | 6/2015 | Fire et al. | |
| 9,234,240 | B2 | 1/2016 | Quake et al. | |
| 9,957,558 | B2 | 5/2018 | Leamon et al. | |
| 10,920,273 | B2 | 2/2021 | Looney et al. | |
| 11,008,609 | B2 | 5/2021 | Lowman et al. | |
| 2006/0234234 | A1* | 10/2006 | Van Dongen ........ | C12Q 1/6886 435/6.12 |
| 2013/0059738 | A1 | 3/2013 | Leamon et al. | |
| 2016/0002731 | A1 | 1/2016 | Robins et al. | |
| 2016/0034637 | A1 | 2/2016 | Wang et al. | |
| 2018/0208984 | A1 | 7/2018 | Looney et al. | |

FOREIGN PATENT DOCUMENTS

| | | | |
|---|---|---|---|
| CN | 105189748 | A | 12/2015 |
| CN | 105452483 | A | 3/2016 |
| CN | 106156536 | A | 11/2016 |
| CN | 110249060 | A | 9/2019 |
| WO | WO-2004033728 | A2 | 4/2004 |
| WO | WO 2010/053587 | A2 | 5/2010 |
| WO | WO 2010/094475 | A1 | 8/2010 |
| WO | WO 2011/139371 | A1 | 11/2011 |
| WO | WO 2011/139372 | A1 | 11/2011 |
| WO | WO 2012/027503 | A2 | 3/2012 |
| WO | WO 2013/155119 | A1 | 10/2013 |
| WO | WO 2013/158936 | A1 | 10/2013 |
| WO | WO 2013/188471 | A2 | 12/2013 |
| WO | WO 2014/055561 | A1 | 4/2014 |
| WO | WO 2014/130685 | A1 | 8/2014 |
| WO | WO 2014/144713 | A2 | 9/2014 |
| WO | WO 2014/145992 | A1 | 9/2014 |
| WO | WO 2015/058159 | A1 | 4/2015 |
| WO | WO 2015/134787 | A2 | 9/2015 |
| WO | WO 2016/197131 | A1 | 12/2016 |
| WO | WO 2017/028752 | A1 | 2/2017 |
| WO | WO-2017210469 | A2 | 12/2017 |
| WO | WO 2018/136562 | A2 | 7/2018 |
| WO | WO-2019046817 | A1 | 3/2019 |
| WO | WO 2019/183582 | A1 | 9/2019 |
| WO | WO 2020/018836 | A1 | 1/2020 |
| WO | WO 2020/018837 | A1 | 1/2020 |

OTHER PUBLICATIONS

Arden et al., "Human T-cell receptor variable gene segment families," Immunogenetics 42.6: 455-500, 1995.

Arstila et al., "A direct estimate of the human αß T cell receptor diversity," Science Oct. 1999 286.5441: 958-961, Oct. 1999.

Bashford-Rogers et al., "Capturing needles in haystacks: a comparison of B-cell receptor sequencing methods—Supplementary information", BMC Immunology 15: 29, 2014, retrieved from the Internet at URL: << https://static-content.springer.com/esm/art%3A10.1186%2Fs12865-014-0029-0/MediaObjects/12865_2014_29_MOESM1_ESM.pdf>> on Oct. 17, 2019 (12 pages).

Bashford-Rogers et al., "Capturing needles in haystacks: a comparison of B- cell receptor sequencing methods", BMC Immunology 15: 29, 2014 (9 pages).

Bolotin et al., "Next generation sequencing for TCR repertoire profiling: Platform-specific features and correction algorithms," Eur J Immunol. 42.11: 3073-3083, 2012.

Brochet et al., "IMGT/V-QUEST: the highly customized and integrated system for IG and TR standardized V-J and V-D-J sequence analysis," Nucleic Acids Res. 36: W503-W508, 2008.

Calis and Rosenberg, "Characterizing immune repertoires by high throughput sequencing: strategies and applications," Trends Immunol. 35.12: 581-590, Dec. 2014.

Carlson et al., "Using synthetic templates to design an unbiased multiplex PCR assay," Nature Communications 4: 2680, 2013 (9 pages).

Chothia and Lesk, "Canonical structures for the hypervariable regions of immunoglobulins," J Mol Biol. 196.4: 901-917, 1987.

Davis et al., "T-cell antigen receptor genes and T-cell recognition," Nature 334: 395-402, 1998.

Elnifro et al., "Multiplex PCR: Optimization and Application in Diagnostic Virology," Clinical Microbiology Reviews 13.4: 559-570, Oct. 2000.

Extended European Search Report mailed in European Patent Application No. 22166477.4 by the European Patent Office on Jul. 22, 2022 (11 pages).

Extended European Search Report mailed in European Patent Application No. 22172110.3 by the European Patent Office on Jun. 19, 2023 (11 pages).

Extended European Search Report mailed in European Patent Application No. 23187659.0 by the European Patent Office on Dec. 15, 2023 (9 pages).

Gnjatic et al., "Identifying baseline immune-related biomarkers to predict clinical outcome of immunotherapy", Journal of ImmunoTherapy of Cancer 5.1: 44, 2017 (18 pages).

International Search Report and Written Opinion mailed in International Application No. PCT/US2018/014111 by the European Patent Office as International Search Authority on Aug. 9, 2018 (23 pages).

International Search Report and Written Opinion mailed in International Application No. PCT/US2018/049259 by the European Patent Office as International Search Authority on Dec. 7, 2018 (14 pages).

International Search Report and Written Opinion mailed in International Application No. PCT/US2019/023731 by the European Patent Office as International Search Authority on Sep. 9, 2019 (17 pages).

International Search Report and Written Opinion mailed in International Application No. PCT/US2019/042474 by the European Patent Office as International Search Authority on Oct. 29, 2019 (13 pages).

International Search Report and Written Opinion mailed in International Application No. PCT/US2021/070065 by the European Patent Office as International Search Authority on May 14, 2021 (13 pages).

International Search Report and Written Opinion mailed in International Application No. PCT/US2021/072421 by the European Patent Office as International Search Authority on Mar. 11, 2022 (11 pages).

International Search Report and Written Opinion mailed in International Application No. PCT/US2021/072434 by the European Patent Office as International Search Authority on Mar. 14, 2022 (12 pages).

Invitation to Pay Additional Fees and Partial Search Report mailed in International Application No. PCT/US2019/023731 by the European Patent Office as International Search Authority on Jul. 5, 2019 (12 pages).

Laydon et al., "Estimating T-cell repertoire diversity: limitations of classical estimators and a new approach", Phil Trans R Soc B 370: 20140291, 2015 (11 pages).

Liu et al., "Direct Measurement of B-cell Receptor Repertoire's Composition and Variation in Systemic Lupus Erythematosus," Genes and Immunity 18:1 2017 (6 pages).

Liu et al., "Direct Measurement of B-cell Receptor Repertoire's Composition Variation in Systemic Lupus Erythematosus T—Table S1 Multiplex-PCR Amplification Primers of the IGH CDR3 Region. Primers sequences", Genes and Immunity 18:1 2017, retrieved from the Internet at URL <<https://www.nature.com/articles/gene201645#Sec14>> on Oct. 8, 2024 (1 page) (1 page).

Liu et al., "Systematic Comparative Evaluation of Methods for Investigating the TCRß Repertoire," PLoS ONE 11.3: e0152464, Mar. 2016 (18 pages).

Looney et al., "Long-amplicon TCR Beta repertoire sequencing to reveal human T-Cell receptor variable gene polymorphism: Implications for the prediction and interpretation of immunotherapy outcome", Journal of Clinical Oncology 36: 129 2018.

Mackelprang et al., "Sequence diversity, natural selection and linkage disequilibrium in the human T cell receptor alpha/delta locus," Hum Genet. 119.3: 255-266, 2006.

(56) References Cited

OTHER PUBLICATIONS

Peng et al., "Reducing amplification artifacts in high multiplex amplicon sequencing by using molecular barcodes," BMC Genomics 16: 589, 2015 (12 pages).
Rachlin et al., "Computational tradeoffs in multiplex PCR assay design for SNP genotyping," BMC Genomics 6: 102, Jul. 2005 (11 pages).
Rowen et al., "The complete 685-kilobase DNA sequence of the human ß T cell receptor locus," Science 272.5269: 1755-1762, Jun. 1996.
Sandberg et al., "Human T-cell lines with well-defined T-cell receptor gene rearrangements as controls for the BIOMED-2 multiplex polymerase chain reaction tubes," Leukemia 21.2:.230-237, 2006.
Sarkozy et al., "Flow Index Based Characterization of Next Generation Sequencing Errors: Visualizing Pyrosequencing and Semiconductor Sequencing to Cope with Homopolymer Errors," Proceedings of the International Conference on Bioinformatics Models, Methods and Algorithms: 271-277, 2014.
Shen et al., "MPprimer: A program for reliable multiplex PCR primer design," BMC Bioinformatics 11: 143, 2010 (7 pages).
Stiller et al., "Direct multiplex sequencing (DMPS)—a novel method for targeted high-throughput sequencing of ancient and highly degraded DNA", Genome Research 19: 1843-1848, 2009.
Xie et al., "Designing highly multiplex PCR primer sets with Simulated Annealing Design using Dimer Likelihood Estimation (Saddle)," Nature Communications 13.1: 1881, 2022 (10 pages).
Yu et al., "Application Value of Immune Repertoire Sequencing in the Diagnosis and Efficacy Prediction of Lymphohematological Tumors," Chinese Medical Frontiers 10.10: 6-9, Dec. 2018 (with Eng. Abstract).
Zhang et al., "IMonitor: A Robust Pipeline for TCR and BCR Repertoire Analysis," Genetics 201.2: 459-472, 2015.
Greiff, V et al., "Quantitative Assessment of the Robustness of Next-Generation Sequencing of Antibody Variable Gene Repertoires from immunized Mice", BMC Immunology, Biomed Central, London, GB, vol. 15, No. 1, Oct. 16, 2014, pp. 40, XP021203856, ISSN: 1471-2172, DOI:10.1186/S12865-014-0040-5.
Hou, D. et al., "High-Throughput Sequencing-Based Immune Repertoire Study during Infectious Disease", Frontiers in Immunology, vol. 7, Aug. 31, 2016, XP055557258, DOI: 10.3389/fimmu.2016.00336.
Hou X., et al., "Analysis of the Repertoire Features of TCR Beta Chain CDR3 in Human by High-Throughput Sequencing," Cellular Physiology and Biochemistry, vol. 39, No. 2, Jul. 29, 2016 (Jul. 29, 2016), pp. 651-667, XP055528308, CH, ISSN: 1015-8987, DOI: 10.1159/000445656.
PCT/US2019/042473, Search Report and Written Opinion, Nov. 5, 2019.
Robins H.S., et al., "Comprehensive assessment of T-cell receptor ß-chain diversity in αß T cells", Blood, vol. 114, No. 19, Nov. 5, 2009 (Nov. 5, 2009), pp. 4099-4107.
Rosati E., et al., "Overview of Methodologies for T-Cell Receptor Repertoire Analysis," BMC Biotechnology, vol. 17, No. 1, Jul. 10, 2017 (Jul. 10, 2017), pp. 1-16, XP055518303, DOI: 10.1186/s12896-017-0379-9.
Van Dongen et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia, Dec. 2003, 17(12):2257-317.

* cited by examiner

COMPOSITIONS AND METHODS FOR IMMUNE REPERTOIRESEQUENCING

CROSS-REFERENCE TO RELATED APPLICATIONS

This application claims priority to and the benefit of U.S. Provisional Application No. 62/846,497 filed May 10, 2019 and U.S. Provisional Application No. 62/700,056 filed Jul. 18, 2018. The entire contents of each of the aforementioned applications are incorporated herein by reference.

BACKGROUND

Adaptive immune response comprises selective response of B and T cells recognizing antigens. The immunoglobulin genes encoding antibody (Ab, in B cell) and T-cell receptor (TCR, in T cell) antigen receptors comprise complex loci wherein extensive diversity of receptors is produced as a result of recombination of the respective variable (V), diversity (D), and joining (J) gene segments, as well as subsequent somatic hypermutation events during early lymphoid differentiation. The recombination process occurs separately for both subunit chains of each receptor and subsequent heterodimeric pairing creates still greater combinatorial diversity. Calculations of the potential combinatorial and junctional possibilities that contribute to the human immune receptor repertoire have estimated that the number of possibilities greatly exceeds the total number of peripheral B or T cells in an individual. See, for example, Davis and Bjorkman (1988) Nature 334:395-402; Arstila et al. (1999) Science 286:958-961; van Dongen et al., In: Leukemia, Henderson et al. (eds) Philadelphia: WB Saunders Company, 2002, pp 85-129.

Extensive efforts have been made over years to improve analysis of the immune repertoire at high resolution. Means for specific detection and monitoring of expanded clones of lymphocytes would provide significant opportunities for characterization and analysis of normal and pathogenic immune reactions and responses. Despite efforts, effective high resolution analysis has provided challenges. Low throughput techniques such as Sanger sequencing may provide resolution, but are limited to provide efficient means to broadly capture the entire immune repertoire. Advances in next generation sequencing (NGS) have provided access to capturing the repertoire, however, due to the nature of the numerous related sequences and introduction of sequence errors as a result of the technology, efficient and effective reflection of the true repertoire has proven difficult. Thus, improved sequencing methodologies and workflows capable of resolving complex populations of highly variable immune cell receptor sequences are being developed. There remains a need for new methods for effective profiling of vast repertoires of immune cell receptors to better understand immune cell response, enhance diagnostic and treatment capabilities, and devise new therapeutics.

SUMMARY OF THE INVENTION

In one aspect of the invention compositions are provided for a single stream determination of an immune repertoire in a sample. In some embodiments the composition comprises at least one set of primers i) and ii), wherein i) consists of a plurality of variable (V) gene primers directed to a majority of different V genes of an immune receptor coding sequence; and ii) consists of a plurality of joining (J) gene primers directed to a majority of different J genes of the respective target immune receptor coding sequence. In certain embodiments, the compositions comprise primer sets directed to murine V genes and J genes. In some embodiments the composition for analysis of a murine immune cell receptor repertoire in a sample comprises at least one set of primers i) and ii), wherein i) consists of a plurality of V gene primers directed to a majority of different V genes of at least one murine immune receptor coding sequence comprising at least a portion of framework region 3 (FR3) within the V gene; and ii) consists of a plurality of J gene primers directed to at least a portion of a majority of different J genes of the at least one murine immune receptor coding sequence; wherein each set of i) and ii) primers directed to coding sequences of the same target murine immune receptor gene; and wherein each set of i) and ii) primers directed to the same target murine immune receptor is configured to amplify the target murine immune receptor repertoire.

In some embodiments the V gene primers recognize at least a portion of FR3 within the TCR beta V gene and the J gene primers recognize at least a portion of the TCR beta J gene. In some embodiments the V gene primers recognize at least a portion of FR3 within the BCR IgH V gene and the J gene primers recognize at least a portion of the BCR IgH J gene. Each set of i) and ii) primers are directed to the same target murine immune receptor sequence, for example murine TCR beta sequence or murine IgH sequence, and configured such that resulting amplicons generated using such compositions represent the repertoire of sequences of the respective murine immune receptor in a sample. In particular embodiments, provided compositions include a plurality of primer pair reagents selected from primers of Table 2 and Table 3. In other embodiments, provided compositions include a plurality of primer pair reagents selected from primers of Table 4 and Table 5. In some embodiments a multiplex assay comprising compositions of the invention is provided. In some embodiments a test kit comprising compositions of the invention is provided.

In other aspects of the invention, methods are provided for determining immune repertoire activity in a biological sample. In some embodiments, the provided method is for amplification of expression nucleic acid of an immune receptor repertoire in a sample comprises performing a single multiplex amplification reaction to amplify expressed target immune receptor nucleic acid template molecules using at least one set of:

i) a plurality of V gene primers directed to a majority of different V genes of at least one immune receptor coding sequence comprising at least a portion of FR3 within the V gene; and ii) a plurality of J gene primers directed to at least a portion of a majority of different J genes of the at least one immune receptor coding sequence;

wherein each set of i) and ii) primers is directed to coding sequences of the same target immune receptor gene selected from a T cell receptor gene or an antibody receptor gene and wherein performing the amplification using the at least one set of i) and ii) primers results in amplicon molecules representing the target immune receptor repertoire in the sample; thereby generating immune receptor amplicon molecules comprising the expressed target immune receptor repertoire.

In some embodiments, the provided method is for amplification of rearranged genomic DNA sequences of an immune receptor repertoire in a sample comprises performing a single multiplex amplification reaction to amplify target immune receptor DNA template molecules having a J gene portion and a V gene portion, the target immune receptor DNA having rearranged VDJ or VJ gene segments, using at least one set of:

i) a plurality of V gene primers directed to a majority of different V genes of at least one immune receptor coding sequence comprising at least a portion of FR3 within the V gene; and ii) a plurality of J gene primers directed to at least a portion of a majority of different J genes of the at least one immune receptor coding sequence;

wherein each set of i) and ii) primers is directed to coding sequences of the same target immune receptor gene selected from a T cell receptor gene or an antibody receptor gene and wherein performing the amplification using the at least one set of i) and ii) primers results in amplicon molecules representing the target immune receptor repertoire in the sample; thereby generating immune receptor amplicon molecules comprising the target immune receptor repertoire.

In certain embodiments at least a portion of FR3 of the V gene to at least a portion of the J gene of the immune receptor sequence is encompassed within amplified target immune receptor sequences. In some embodiments, the methods use primer sets directed to murine TCR V genes and J genes. In particular embodiments, the methods use primer sets directed to murine TCR beta V genes and J genes. In some embodiments, the methods comprise the use of at least one set of a plurality of primer pair reagents selected from primers of Table 2 and Table 3. In some embodiments, the methods use primer sets directed to murine antibody (B cell receptor (BCR)) V genes and J genes. In other particular embodiments, the methods use primer sets directed to murine BCR IgH V genes and J genes. In some embodiments, the methods comprise the use of at least one set of a plurality of primer pair reagents selected from primers of Table 4 and Table 5.

Methods of the invention further comprise preparing an immune receptor repertoire library using the amplified target immune receptor sequences through introducing adapter sequences to the termini of the amplified target sequences. In some embodiments, the adapter-modified immune receptor repertoire library is clonally amplified.

The methods further comprise sequencing of the immune receptor amplicon molecules is carried out using next generation sequencing and analysis to determine sequence of the immune receptor amplicons. In particular embodiments determining the sequence of the immune receptor amplicon molecules includes obtaining initial sequence reads, aligning and identifying productive reads and correcting errors to generate rescued productive reads and determining the sequences of the resulting total productive reads, thereby providing sequence of the immune repertoire in the sample. Provided methods described herein utilize compositions of the invention provided herein. In still other aspects of the invention, particular analysis methodology for error correction is provided in order to generate comprehensive, effective sequence information from methods provided herein.

DESCRIPTION OF THE INVENTION

Figure 1:
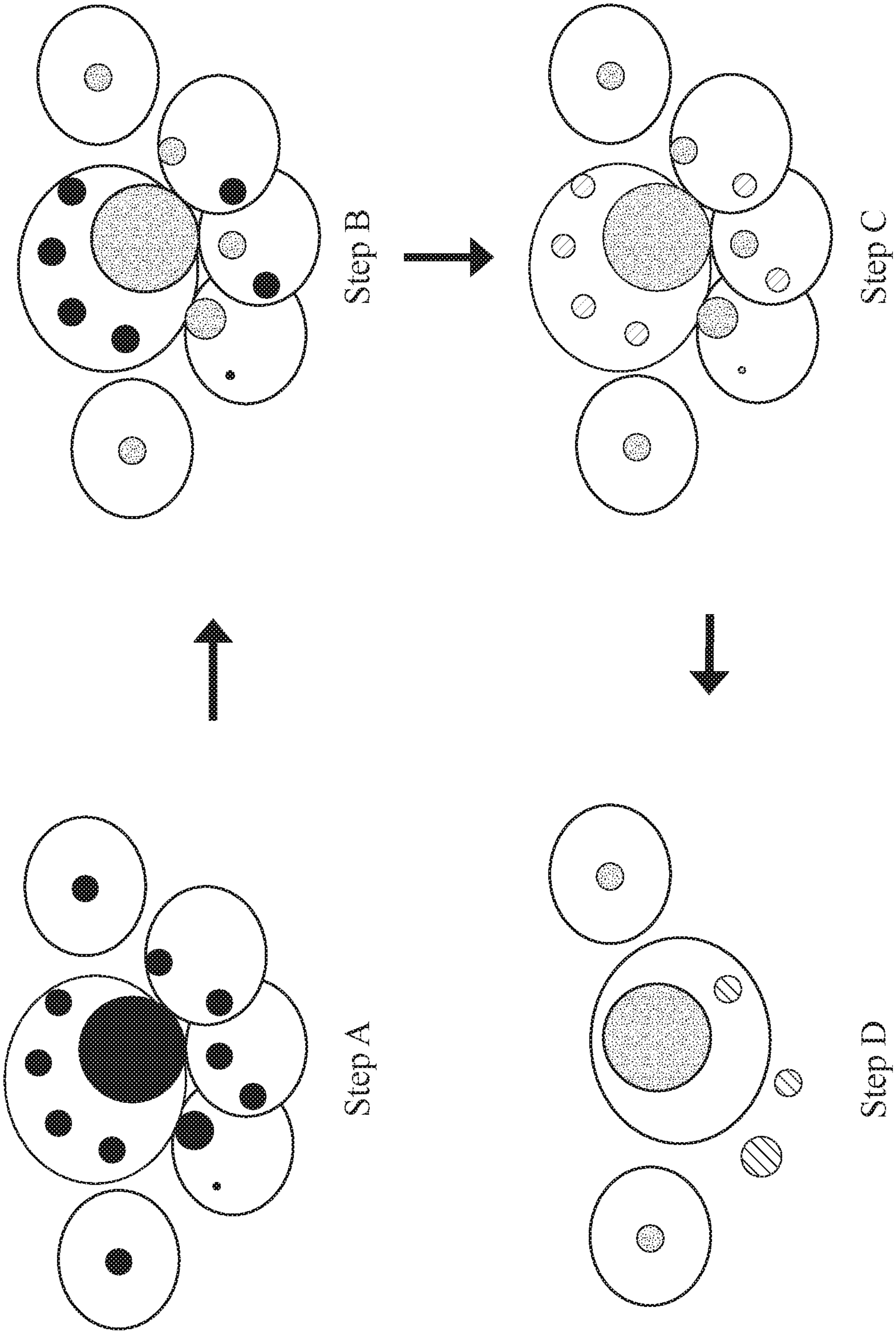
FIG. 1 is a diagram of an exemplary workflow for removal of PCR or sequencing-derived errors using stepwise clustering of similar CDR3 nucleotides sequences with steps: (A) very fast heuristic clustering into groups based on similarity (cd-hit-est); (B) cluster representative chosen as most common sequence, randomly picked for ties; (C) merge reads into representatives; (D) compare representatives and if within allotted hamming distance, merge clusters.

We have developed a multiplex next generation sequencing workflow for effective detection and analysis of the immune repertoire in a sample. Provided methods, compositions, systems, and kits are for use in high accuracy amplification and sequencing of immune cell receptor sequences (e.g., T cell receptor (TCR), B cell receptor (BCR or Ab) targets) in monitoring and resolving complex immune cell repertoire(s) in a subject. In certain embodiments, provided methods, compositions, systems, and kits are directed to amplification and sequencing immune cell receptor sequences of an animal, including animals used as models for disease(s). In some embodiments, the animal subject is a mouse and provided methods, compositions, systems, and kits are directed to amplification, sequencing, and analysis of murine immune cell receptor nucleic acid sequences. Methods and compositions provided were designed to amplify and identify expressed or rearranged immune receptor nucleic acid sequences found in most mouse strains commonly used in laboratory research and disease modeling. The target immune cell receptor genes have undergone rearrangement (or recombination) of the VDJ or VJ gene segments, the gene segments depending on the particular receptor gene (e.g., TCR beta or TCR alpha). In certain embodiments, the present disclosure provides methods, compositions, and systems that use nucleic acid amplification, such as polymerase chain reaction (PCR), to enrich expressed variable regions of immune receptor target nucleic acid for subsequent sequencing. In certain embodiments, the present disclosure provides methods, compositions, and systems that use nucleic acid amplification, such as PCR, to enrich rearranged target immune cell receptor gene sequences from gDNA for subsequent sequencing. In certain embodiments, the present disclosure also provides methods and systems for effective identification and removal of amplification or sequencing-derived error(s) to improve read assignment accuracy and lower the false positive rate. In particular, provided methods described herein may improve accuracy and performance in sequencing applications with nucleotide sequences associated with genomic recombination and high variability. In some embodiments, methods, compositions, systems, and kits provided herein are for use in amplification and sequencing of the complementarity determining regions (CDRs) of an expressed immune receptor in a sample. In some embodiments, methods, compositions, systems, and kits provided herein are for use in amplification and sequencing of the CDRs of rearranged immune cell receptor gDNA in a sample. Thus, provided herein are multiplex immune cell receptor expression compositions and immune cell receptor gene-directed compositions for multiplex library preparation, use in conjunction with next generation sequencing technologies and workflow solutions (e.g., manual or automated), for effective detection and characterization of the immune repertoire in a sample.

The CDRs of a TCR or BCR results from genomic DNA undergoing recombination of the V(D)J gene segments as well as addition and/or deletion of nucleotides at the gene segment junctions. Recombination of the V(D)J gene segments and subsequent hypermutation events leads to extensive diversity of the expressed immune cell receptors. With the stochastic nature of V(D)J recombination, it is often the case that rearrangement of the T or B cell receptor genomic DNA will fail to produce a functional receptor, instead producing what is termed an “unproductive” rearrangement. Typically, unproductive rearrangements have out-of-frame Variable and Joining coding segments, and lead to the presence of premature stop codons and synthesis of irrelevant peptides. Unproductive TCR or BCR gene rearrangements are generally rare in cDNA-based repertoire sequencing for a number of biological or physiological reasons such as: 1) nonsense-mediated decay, which destroys mRNA containing premature stop codons, 2) B and T cell selection, where only B and T cells with a functional receptor survive, and 3) allelic exclusion, where only a single rearranged receptor allele is expressed in any given B or T cell.

Accordingly, in some embodiments, methods and compositions provided herein are used for amplifying the recombined, expressed variable regions of immune cell receptor mRNA, eg TCR and BCR mRNA. In some embodiments, RNA extracted from biological samples is converted to cDNA. Multiplex amplification is used to enrich for a portion of TCR or BCR cDNA which includes at least a portion of the variable region of the receptor. In some embodiments, the amplified cDNA includes one or more complementarity determining regions CDR1, CDR2, and/or CDR3 for the target receptor. In some embodiments, the amplified cDNA includes one or more complementarity determining regions CDR1, CDR2, and/or CDR3 for TCR beta. In some embodiments, the amplified cDNA includes one or more complementarity determining regions CDR1, CDR2, and/or CDR3 for immunoglobulin heavy chain (IgH).

TCR and BCR sequences can also appear as unproductive rearrangements from errors introduced during amplification reactions or during sequencing processes. For example, an insertion or deletion (indel) error during a target amplification or sequencing reaction can cause a frameshift in the reading frame of the resulting coding sequence. Such a change may result in a target sequence read of a productive rearrangement being interpreted as an unproductive rearrangement and discarded from the group of identified clonotypes. Accordingly, in some embodiments, methods and systems provided herein include processes for identification and/or removing PCR or sequencing-derived error from the determined immune receptor sequence.

In some embodiments, methods and compositions provided are used for amplifying the rearranged variable regions of immune cell receptor gDNA, e.g., rearranged TCR and BCR gene DNA. Multiplex amplification is used to enrich for a portion of rearranged TCR or BCR gDNA which includes at least a portion of the variable region of the receptor. In some embodiments, the amplified gDNA includes one or more complementarity determining regions CDR1, CDR2, and/or CDR3 for the target receptor. In some embodiments, the amplified gDNA includes one or more complementarity determining regions CDR1, CDR2, and/or CDR3 for TCR beta. In some embodiments, the amplified gDNA includes one or more complementarity determining regions CDR1, CDR2, and/or CDR3 for IgH. In some embodiments, the amplified gDNA includes primarily CDR3 for the target receptor, e.g., CDR3 for TCR beta or CDR3 for IgH.

As used herein, “immune cell receptor” and “immune receptor” are used interchangeably.

As used herein, the terms “complementarity determining region” and “CDR” refer to regions of a T cell receptor or an antibody where the molecule complements an antigen’s conformation, thereby determining the molecule’s specificity and contact with a specific antigen. In the variable regions of T cell receptors and antibodies, the CDRs are interspersed with regions that are more conserved, termed framework regions (FR). Each variable region of a T cell receptor and an antibody contains 3 CDRs, designated CDR1, CDR2 and CDR3, and also contains 4 framework sub-regions, designated FR1, FR2, FR3 and FR4.

As used herein, the term “framework” or “framework region” or “FR” refers to the residues of the variable region other than the CDR residues as defined herein. There are four separate framework sub-regions that make up the framework: FR1, FR2, FR3, and FR4.

The particular designation in the art for the exact location of the CDRs and FRs within the receptor molecule (TCR or immunoglobulin) varies depending on what definition is employed. Unless specifically stated otherwise, the IMGT designations are used herein in describing the CDR and FR regions (see Brochet et al. (2008) Nucleic Acids Res. 36:W503-508, herein specifically incorporated by reference). As one example of CDR/FR amino acid designations, the residues that make up the FRs and CDRs of T cell receptor beta have been characterized by IMGT as follows: residues 1-26 (FR1), 27-38 (CDR1), 39-55 (FR2), 56-65 (CDR2), 66-104 (FR3), 105-117 (CDR3), and 118-128 (FR4).

Other well-known standard designations for describing the regions include those found in Kabat et al., (1991) Sequences of Proteins of Immunological Interest, 5th Ed. Public Health Service, National Institutes of Health, Bethesda, Md., and in Chothia and Lesk (1987) J. Mol. Biol. 196:901-917; herein specifically incorporated by reference. As one example of CDR designations, the residues that make up the six immunoglobulin CDRs have been characterized by Kabat as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; and by Chothia as follows: residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region.

The term “T cell receptor” or “T cell antigen receptor” or “TCR,” as used herein, refers to the antigen/MHC binding heterodimeric protein product of a vertebrate, e.g. mammalian, TCR gene complex, including the human TCR alpha, beta, gamma and delta chains. For example, the complete sequence of the human TCR beta locus has been sequenced, see, for example, Rowen et al. (1996) Science 272:1755-1762; the human TCR alpha locus has been sequenced and resequenced, see, for example, Mackelprang et al. (2006) Hum Genet. 119:255-266; and see, for example, Arden (1995) Immunogenetics 42:455-500 for a general analysis of the T-cell receptor V gene segment families; each of which is herein specifically incorporated by reference for the sequence information provided and referenced in the publication.

The term “antibody” or immunoglobulin” or “B cell receptor” or “BCR,” as used herein, is intended to refer to immunoglobulin molecules comprised of four polypeptide chains, two heavy (H) chains and two light (L) chains (lambda or kappa) inter-connected by disulfide bonds. An antibody has a known specific antigen with which it binds. Each heavy chain of an antibody is comprised of a heavy chain variable region (abbreviated herein as HCVR, HV or VH) and a heavy chain constant region. The heavy chain constant region is comprised of three domains, CH1, CH2 and CH3. Each light chain is comprised of a light chain variable region (abbreviated herein as LCVR or VL or KV or LV to designate kappa or lambda light chains) and a light chain constant region. The light chain constant region is comprised of one domain, CL.

As noted, the diversity of the TCR and BCR chain CDRs is created by recombination of germline variable (V), diversity (D), and joining (J) gene segments, as well as by independent addition and deletion of nucleotides at each of the gene segment junctions during the process of TCR and BCR gene rearrangement. In the rearranged nucleic acid encoding a TCR beta and a TCR delta, for example, CDR1 and CDR2 are found in the V gene segments and CDR3 includes some of the V gene segment, and the D and J gene segments. In the rearranged nucleic acid encoding a TCR alpha and a TCR gamma, CDR1 and CDR2 are found in the V gene segments and CDR3 includes some of the V gene segment and the J gene segment. In the rearranged nucleic acid encoding a BCR heavy chain, CDR1 and CDR2 are found in the V gene segment and CDR3 includes some of the V gene segment and the D and J gene segments. In the rearranged nucleic acid encoding a BCR light chain, CDR1 and CDR2 are found in the V gene segment and CDR3 includes some of the V gene segment and the J gene segment.

In some embodiments, a multiplex amplification reaction is used to amplify cDNA derived from mRNA expressed from rearranged TCR and/or BCR genomic DNA. In some embodiments, a multiplex amplification reaction is used to amplify at least a portion of a TCR and/or BCR CDR from cDNA derived from a biological sample. In some embodiments, a multiplex amplification reaction is used to amplify at least two CDRs of a TCR and/or BCR from cDNA derived from a biological sample. In some embodiments, a multiplex amplification reaction is used to amplify at least three CDRs of a TCR and/or BCR from cDNA derived from a biological sample. In some embodiments, the resulting amplicons are used to determine the nucleotide sequences of the TCR and/or BCR CDRs expressed in the sample. In some embodiments, determining the nucleotide sequences of such amplicons comprising at least 3 CDRs is used to identify and characterize novel TCR and/or BCR alleles. In some embodiments, determining the nucleotide sequences of such amplicons comprising at least 3 CDRs is used to identify and characterize novel TCR and/or BCR alleles.

In some embodiments, a multiplex amplification reaction is used to amplify TCR and/or BCR genomic DNA having undergone V(D)J rearrangement. In some embodiments, a multiplex amplification reaction is used to amplify nucleic acid molecule(s) comprising at least a portion of a TCR and/or BCR CDR from gDNA derived from a biological sample. In some embodiments, a multiplex amplification reaction is used to amplify nucleic acid molecule(s) comprising at least two CDRs of a TCR and/or BCR from gDNA derived from a biological sample. In some embodiments, a multiplex amplification reaction is used to amplify nucleic acid molecules comprising at least three CDRs of a TCR and/or BCR from gDNA derived from a biological sample. In some embodiments, the resulting amplicons are used to determine the nucleotide sequences of the rearranged TCR and/or BCR CDRs in the sample. In some embodiments, determining the nucleotide sequences of such amplicons comprising at least CDR3 is used to identify and characterize novel TCR and/or BCR alleles. In some embodiments, determining the nucleotide sequences of such amplicons comprising at least 3 CDRs is used to identify and characterize novel TCR and/or BCR alleles.

In the multiplex amplification reactions, each primer set used target a same TCR or BCR region however the different primers in the set permit targeting the gene's different V(D)J gene rearrangements. For example, the primer set for amplification of the expressed TCR beta or the rearranged TCR beta gDNA are all designed to target the same region(s) from TCR beta mRNA or TCR beta gDNA, respectively, but the individual primers in the set lead to amplification of the various TCR beta VDJ gene combinations. For example, the primer set for amplification of the expressed IgH or the rearranged IgH gDNA are all designed to target the same region(s) from IgH mRNA or IgH gDNA, respectively, but the individual primers in the set lead to amplification of the various IgH VDJ gene combinations. In some embodiments, at least one primer or primer set is directed to a relatively conserved region (eg, a portion of the C gene) of an immune receptor gene and the other primer set includes a variety of primers directed to a more variable region of the same gene (eg, a portion of the V gene). In other embodiments, at least one primer set includes a variety of primers directed to at least a portion of J gene segments of an immune receptor gene and the other primer set includes a variety of primers directed to at least a portion of V gene segments of the same gene.

In some embodiments, a multiplex amplification reaction is used to amplify cDNA derived from mRNA expressed from rearranged TCR genomic DNA, including rearranged TCR beta, TCR alpha, TCR gamma, and TCR delta genomic DNA. In some embodiments, at least a portion of a TCR CDR, for example CDR3, is amplified from cDNA in a multiplex amplification reaction. In some embodiments, at least two CDR portions of TCR are amplified from cDNA in a multiplex amplification reaction. In certain embodiments, a multiplex amplification reaction is used to amplify at least the CDR1, CDR2, and CDR3 regions of a TCR cDNA. In some embodiments, the resulting amplicons are used to determine the expressed TCR CDR nucleotide sequence.

In some embodiments, a multiplex amplification reaction is used to amplify rearranged TCR genomic DNA, including rearranged TCR beta, TCR alpha, TCR gamma, and TCR delta genomic DNA.

In some embodiments, at least a portion of a TCR CDR, for example CDR3, is amplified from gDNA in a multiplex amplification reaction. In some embodiments, at least two CDR portions of TCR are amplified from gDNA in a multiplex amplification reaction. In certain embodiments, a multiplex amplification reaction is used to amplify at least the CDR1, CDR2, and CDR3 regions of a rearranged TCR gDNA. In some embodiments, the resulting amplicons are used to determine the expressed TCR CDR nucleotide sequence.

In some embodiments, a multiplex amplification reaction is used to amplify cDNA derived from mRNA expressed from rearranged BCR genomic DNA, including rearranged IgH, IgK, and IgL genomic DNA. In some embodiments, at least a portion of a BCR CDR, for example CDR3, is amplified from cDNA in a multiplex amplification reaction. In some embodiments, at least two CDR portions of BCR are amplified from cDNA in a multiplex amplification reaction. In certain embodiments, a multiplex amplification reaction is used to amplify at least the CDR1, CDR2, and CDR3 regions of a BCR cDNA. In some embodiments, the resulting amplicons are used to determine the expressed BCR CDR nucleotide sequence. In some embodiments, the resulting amplicons are used to determine the expressed IgH CDR nucleotide sequence.

In some embodiments, a multiplex amplification reaction is used to amplify rearranged BCR genomic DNA, including rearranged IgH, IgK, and IgL genomic DNA. In some embodiments, at least a portion of a BCR CDR, for example CDR3, is amplified from gDNA in a multiplex amplification reaction. In some embodiments, at least two CDR portions of BCR are amplified from gDNA in a multiplex amplification reaction. In certain embodiments, a multiplex amplification reaction is used to amplify at least the CDR1, CDR2, and CDR3 regions of a rearranged BCR gDNA. In some embodiments, the resulting amplicons are used to determine the rearranged BCR CDR nucleotide sequence. In some embodiments, the resulting amplicons are used to determine the rearranged IgH CDR nucleotide sequence.

In some embodiments, multiplex amplification reactions are performed with primer sets designed to generate amplicons which include the CDR1, CDR2, and/or CDR3 regions of the target immune receptor mRNA or rearranged gDNA. In some embodiments, multiplex amplification reactions are performed using (i) one set of primers in which each primer is directed to at least a portion of the framework region FR3 of a V gene and (ii) one set of primers in which each primer is directed to at least a portion of the J gene of the target immune receptor. In some embodiments, the multiplex amplification reaction uses (i) a set of primers each of which anneals to at least a portion of the TCR V gene FR3 region and (ii) a set of primers which anneal to a portion of the TCR J gene to amplify TCR nucleic acid such that the resultant amplicons include primarily the CDR3 coding portion of the TCR mRNA or rearranged gDNA. For example, exemplary primers specific for the TRB V gene FR3 regions are shown in Table 2 and exemplary primers specific for TRB J genes are shown in Table 3.

In some embodiments, the multiplex amplification reaction uses (i) a set of primers each of which anneals to at least a portion of the BCR V gene FR3 region and (ii) a set of primers which anneal to a portion of the BCR J gene to amplify BCR nucleic acid such that the resultant amplicons include primarily the CDR3 coding portion of the BCR mRNA or rearranged gDNA. For example, exemplary primers specific for the IgH V gene FR3 regions are shown in Table 4 and exemplary primers specific for IgH J genes are shown in Table 5.

In some embodiments, provided are compositions for multiplex amplification of at least a portion of an expressed TCR or BCR variable region. In some embodiments, the composition comprises a plurality of sets of primer pair reagents directed to a portion of a V gene framework region and a portion of a J gene of rearranged target immune receptor genes selected from the group consisting of TCR beta, TCR alpha, TCR gamma, TCR delta, immunoglobulin heavy chain, immunoglobulin light chain lambda, and immunoglobulin light chain kappa.

In some embodiments, the composition comprises (i) a plurality of sets of primer pair reagents directed to a portion of an IgH V gene framework region and a portion of an IgH J gene of rearranged IgH genes and (ii) a plurality of sets of primer pair reagents directed to a portion of a TCR beta V gene framework region and a portion of a TCR beta J gene of rearranged TCR beta genes. In some embodiments, the composition comprises (i) a plurality of sets of primer pair reagents directed to a portion of an IgH V gene FR3 region and a portion of an IgH J gene of rearranged IgH genes and (ii) a plurality of sets of primer pair reagents directed to a portion of a TRB V gene FR3 region and a portion of a TRB J gene of rearranged TCR beta genes.

Amplification by PCR is performed with at least two primers. For the methods provided herein, a set of primers is used that is sufficient to amplify all or a defined portion of the variable sequences at the locus of interest, which locus may include any or all of the aforementioned TCR and Immunoglobulin loci. In some embodiments, various parameters or criteria outlined herein may be used to select the set of target-specific primers for the multiplex amplification.

In some embodiments, primer sets used in the multiplex reactions are designed to amplify at least 50% of the known expressed or gDNA rearrangements at the locus of interest. In certain embodiments, primer sets used in the multiplex reactions are designed to amplify at least 75%, at least 85%, at least 90%, at least 95%, at least 97%, at least 98% or more of the known expressed or gDNA rearrangements at the locus of interest. For example, use of 33 forward primers of Table 2, each directed to a portion of the FR3 region from different TCR beta V genes, in combination with 17 reverse primers of Table 3, each directed to a portion of different TCR beta J genes, will amplify all of the currently known murine expressed or gDNA TCR beta rearrangements. In another example, use of about 85-95 forward primers of Table 4, each directed to a portion of the FR3 region from different murine IgH V genes, in combination with about 7 reverse primers of Table 5, each directed to a portion of different murine IgH J genes, will amplify all of the currently known murine expressed or gDNA IgH rearrangements.

In some embodiments, a multiplex amplification reaction includes at least 10, 15, 20, 25, 30, 40, 45, 50, or 60 reverse primers in which each reverse primer is directed to a sequence corresponding to at least a portion of one or more TCR V gene FR3 regions. In such embodiments, the plurality of reverse primers directed to the TCR V gene FR3 regions is combined with at least 10, 12, 14, 16, 18, 20, 25, or about 15 to about 20 forward primers directed to a sequence corresponding to at least a portion of a J gene of the same TCR gene. In some embodiments of the multiplex amplification reactions, the TCR V gene FR3-directed primers may be the forward primers and the TCR J gene-directed primers may be the reverse primers. Accordingly, in some embodiments, a multiplex amplification reaction includes at least 10, 15, 20, 25, 30, 40, 45, 50, or 60 forward primers in which each forward primer is directed to a sequence corresponding to at least a portion of one or more TCR V gene FR3 regions. In such embodiments, the plurality of forward primers directed to the TCR V gene FR3 regions is combined with at least 10, 12, 14, 16, 18, 20, 25, or about 15 to about 20 reverse primers directed to a sequence corresponding to at least a portion of a J gene of the same TCR gene. In some embodiments, such FR3 and J gene amplification primer sets may be directed to TCR beta gene sequences. In some preferred embodiments, about 25 to about 40 reverse primers directed to different TRB V gene FR3 regions are combined with about 12 to about 22 forward primers directed to different TRB J genes. In some preferred embodiments, about 28 to about 38 reverse primers directed to different TRB V gene FR3 regions are combined with about 15 to about 20 forward primers directed to different TRB J genes. In some preferred embodiments, about 25 to about 40 forward primers directed to different TRB V gene FR3 regions are combined with about 12 to about 22 reverse primers directed to different TRB J genes. In some preferred embodiments, about 28 to about 38 forward primers directed to different TRB V gene FR3 regions are combined with about 15 to about 20 reverse primers directed to different TRB J genes. In some preferred embodiments, the forward primers directed to TRB V gene FR3 regions are selected from those listed in Table 2 and the reverse primers directed to the TRB J gene are selected from those listed in Table 3. In other embodiments, the FR3 and J gene amplification primer sets may be directed to TCR alpha, TCR gamma, and TCR delta, gene sequences.

In other embodiments, a multiplex amplification reaction includes at least 70, 75, 80, 85, 90, 95, 100, 105, 110, or 120 reverse primers in which each reverse primer is directed to a sequence corresponding to at least a portion of one or more BCR V gene FR3 regions. In such embodiments, the plurality of reverse primers directed to the BCR V gene FR3 regions is combined with at least 1, 2, 3, 4, 5, 6, 7, 8, 9, 10, 11, 12, or 15 forward primers directed to a sequence corresponding to at least a portion of a J gene of the same BCR gene. In some embodiments of the multiplex amplification reactions, the BCR V gene FR3-directed primers may be the forward primers and the BCR J gene-directed primer(s) may be the reverse primer(s). Accordingly, in some embodiments, a multiplex amplification reaction includes at least 70, 75, 80, 85, 90, 95, 100, 105, 110, or 120 forward primers in which each forward primer is directed to a sequence corresponding to at least a portion of one or more BCR V gene FR3 regions. In such embodiments, the plurality of forward primers directed to the BCR V gene FR3 regions is combined with at least 1, 2, 3, 4, 5, 6, 7, 8, 9, 10, 11, 12, or 15 reverse primers directed to a sequence corresponding to at least a portion of a J gene of the same BCR gene. In some embodiments, such FR3 and J gene amplification primer sets may be directed to IgH gene sequences. In some preferred embodiments, about 80 to about 105 reverse primers directed to different IgH V gene FR3 regions are combined with about 2 to about 12 forward primers directed to a portion of the IgH J genes. In other preferred embodiments, about 85 to about 95 reverse primers directed to different IgH V gene FR3 regions are combined with about 4 to about 8 forward primers directed to a portion of the IgH J genes. In other preferred embodiments, about 80 to about 105 forward primers directed to different IgH V gene FR3 regions are combined with about 2 to about 12 reverse primers directed to a portion of the IgH J genes. In other preferred embodiments, about 85 to about 95 forward primers directed to different IgH V gene FR3 regions are combined with about 4 to about 8 reverse primers directed to a portion of the IgH J genes. In some preferred embodiments, the forward primers directed to IgH V gene FR3 regions are selected from those listed in Table 4 and the reverse primers directed to the IgH J gene are selected from those listed in Table 5. In other embodiments, the FR3 and J gene amplification primer sets may be directed to Ig light chain lambda or Ig light chain kappa gene sequences.

In some embodiments, the concentration of the forward primer is about equal to that of the reverse primer in a multiplex amplification reaction. In other embodiments, the concentration of the forward primer is about twice that of the reverse primer in a multiplex amplification reaction. In other embodiments, the concentration of the forward primer is about half that of the reverse primer in a multiplex amplification reaction. In some embodiments, the concentration of each of the primers targeting the V gene FR region is about 5 nM to about 2000 nM. In some embodiments, the concentration of each of the primers targeting the V gene FR region is about 50 nM to about 800 nM. In some embodiments, the concentration of each of the primers targeting the V gene FR region is about 50 nM to about 400 nM or about 100 nM to about 500 nM. In some embodiments, the concentration of each of the primers targeting the V gene FR region is about 200 nM, about 400 nM, about 600 nM, or about 800 nM. In some embodiments, the concentration of each of the primers targeting the V gene FR region is about 5 nM, about 10 nM, about 50 nM, about 100 nM, about 150 nM. In some embodiments, the concentration of each of the primers targeting the V gene FR region is about 1000 nM, about 1250 nM, about 1500 nM, about 1750 nM, or about 2000 nM. In some embodiments, the concentration of each of the primers targeting the V gene FR region is about 50 nM to about 800 nM. In some embodiments, the concentration of each of the primers targeting the J gene is about 5 nM to about 2000 nM. In some embodiments, the concentration of each of the primers targeting the J gene is about 50 nM to about 800 nM. In some embodiments, the concentration of each of the primers targeting the J gene is about 50 nM to about 400 nM or about 100 nM to about 500 nM. In some embodiments, the concentration of each of the primers targeting the J gene is about 200 nM, about 400 nM, about 600 nM, or about 800 nM. In some embodiments, the concentration of each of the primers targeting the J gene is about 5 nM, about 10 nM, about 50 nM, about 100 nM, about 150 nM. In some embodiments, the concentration of each of the primers targeting the J gene is about 1000 nM, about 1250 nM, about 1500 nM, about 1750 nM, or about 2000 nM. In some embodiments, the concentration of each of the primers targeting the J gene is about 50 nM to about 800 nM. In some embodiments, the concentration of each forward and reverse primer in a multiplex reaction is about 50 nM, about 100 nM, about 200 nM, or about 400 nM. In some embodiments, the concentration of each forward and reverse primer in a multiplex reaction is about 5 nM to about 2000 nM. In some embodiments, the concentration of each forward and reverse primer in a multiplex reaction is about 50 nM to about 800 nM. In some embodiments, the concentration of each forward and reverse primer in a multiplex reaction is about 50 nM to about 400 nM or about 100 nM to about 500 nM. In some embodiments, the concentration of each forward and reverse primer in a multiplex reaction is about 600 nM, about 800 nM, about 1000 nM, about 1250 nM, about 1500 nM, about 1750 nM, or about 2000 nM. In some embodiments, the concentration of each forward and reverse primer in a multiplex reaction is about 5 nM, about 10 nM, about 150 nM or 50 nM to about 800 nM.

In some embodiments, the V gene FR and C gene target-directed primers combine as amplification primer pairs to amplify target immune receptor cDNA sequences and generate target amplicons. Generally, the length of a target amplicon will depend upon which V gene primer set (eg, FR1, FR2, or FR3 directed primers) is paired with the C gene primer(s). Accordingly, in some embodiments, target amplicons can range from about 100 nucleotides (or bases or base pairs) in length to about 600 nucleotides (or bases or base pairs) in length.

In some embodiments, the V gene FR and J gene target-directed primers combine as amplification primer pairs to amplify target immune receptor cDNA or rearranged gDNA sequences and generate target amplicons. Generally, the length of a target amplicon will depend upon which V gene primer set (eg, FR1, FR2, or FR3 directed primers) is paired with the J gene primers. Accordingly, in some embodiments, target amplicons can range from about 50 nucleotides to about 350 nucleotides in length. In some embodiments, target amplicons are about 50 to about 200, about 70 to about 170, about 200 to about 350, about 250 to about 320, about 270 to about 300, about 225 to about 300, about 250 to about 275, about 200 to about 235, about 200 to about 250, or about 175 to about 275 nucleotides in length. In some embodiments, TCR beta amplicons are about 80, about 60 to about 100, or about 70 to about 90 nucleotides in length. In some embodiments, TCR beta amplicons, such as those generated using V gene FR3- and J gene-directed primer pairs, are about 50 to about 200 nucleotides in length, preferably about 60 to about 160, about 65 to about 120, about 70 to about 90 nucleotides, or about 80 nucleotides in length. In some embodiments, IgH amplicons are about 80, about 60 to about 100, or about 70 to about 90 nucleotides in length. In some embodiments, IgH amplicons, such as those generated using V gene FR3- and J gene-directed primer pairs, are about 50 to about 200 nucleotides in length, preferably about 60 to about 160, about 65 to about 120, about 90 to about 120, about 70 to about 90 nucleotides, or about 80 nucleotides in length. In some embodiments, generating amplicons of such short lengths allows the provided methods and compositions to effectively detect and analyze the immune repertoire from highly degraded gDNA template material, such as that derived from an FFPE sample or cell-free DNA sample.

In some embodiments, amplification primers may include a barcode sequence, for example to distinguish or separate a plurality of amplified target sequences in a sample. In some embodiments, amplification primers may include two or more barcode sequences, for example to distinguish or separate a plurality of amplified target sequences in a sample. In some embodiments, amplification primers may include a tagging sequence that can assist in subsequent cataloguing, identification or sequencing of the generated amplicon. In some embodiments, the barcode sequence(s) or the tagging sequence(s) is incorporated into the amplified nucleotide sequence through inclusion in the amplification primer or by ligation of an adapter. Primers may further comprise nucleotides useful in subsequent sequencing, e.g. pyrosequencing. Such sequences are readily designed by commercially available software programs or companies.

In some embodiments, multiplex amplification is performed with target-directed amplification primers which do not include a tagging sequence. In other embodiments, multiplex amplification is performed with amplification primers each of which include a target-directed sequence and a tagging sequence such as, for example, the forward primer or primer set includes tagging sequence 1 and the reverse primer or primer set includes tagging sequence 2. In still other embodiments, multiplex amplification is performed with amplification primers where one primer or primer set includes target directed sequence and a tagging sequence and the other primer or primer set includes a target-directed sequence but does not include a tagging sequence, such as, for example, the forward primer or primer set includes a tagging sequence and the reverse primer or primer set does not include a tagging sequence.

Accordingly, in some embodiments, a plurality of target cDNA or gDNA template molecules are amplified in a single multiplex amplification reaction mixture with TCR or BCR directed amplification primers in which the forward and/or reverse primers include a tagging sequence and the resultant amplicons include the target TCR and/or BCR sequence and a tagging sequence on one or both ends. In some embodiments, the forward and/or reverse amplification primer or primer sets may also include a barcode and the one or more barcode is then included in the resultant amplicon.

In some embodiments, a plurality of target cDNA and/or gDNA template molecules are amplified in a single multiplex amplification reaction mixture with TCR and/or BCR directed amplification primers and the resultant amplicons contain only TCR and/or BCR sequences. In some embodiments, a tagging sequence is added to the ends of such amplicons through, for example, adapter ligation. In some embodiments, a barcode sequence is added to one or both ends of such amplicons through, for example, adapter ligation.

Nucleotide sequences suitable for use as barcodes and for barcoding libraries are known in the art. Adapters and amplification primers and primer sets including a barcode sequence are commercially available. Oligonucleotide adapters containing a barcode sequence are also commercially available including, for example, IonXpress™, IonCode™ and Ion Select barcode adapters (Thermo Fisher Scientific). Similarly, additional and other universal adapter/primer sequences described and known in the art (e.g., Illumina universal adapter/primer sequences, PacBio universal adapter/primer sequences, etc.) can be used in conjunction with the methods and compositions provided herein and the resultant amplicons sequenced using the associated analysis platform.

In some embodiments, two or more barcodes are added to amplicons when sequencing multiplexed samples. In some embodiments, at least two barcodes are added to amplicons prior to sequencing multiplexed samples to reduce the frequency of artefactual results (e.g., immune receptor gene rearrangements or clone identification) derived from barcode cross-contamination or barcode bleed-through between samples. In some embodiments, at least two bar codes are used to label samples when tracking low frequency clones of the immune repertoire. In some embodiments, at least two barcodes are added to amplicons when the assay is used to detect clones of frequency less than 1:1,000. In some embodiments, at least two barcodes are added to amplicons when the assay is used to detect clones of frequency less than 1:10,000. In other embodiments, at least two barcodes are added to amplicons when the assay is used to detect clones of frequency less than 1:20,000, less than 1:40,000, less than 1:100,000, less than 1:200,000, less than 1:400,000, less than 1:500,00, or less than 1:1,000,000. Methods for characterizing the immune repertoire which benefit from a high sequencing depth per clone and/or detection of clones at such low frequencies include, but are not limited to, monitoring a subject with a hyperproliferative disease or condition undergoing treatment and testing for minimal residual disease following treatment.

In some embodiments, target-specific primers (e.g., the V gene FR1-, FR2- and FR3-directed primers, the J gene directed primers, and the C gene directed primers) used in the methods of the invention are selected or designed to satisfy any one or more of the following criteria: (1) includes two or more modified nucleotides within the primer sequence, at least one of which is included near or at the termini of the primer and at least one of which is included at, or about the center nucleotide position of the primer sequence; (2) length of about 15 to about 40 bases in length; (3) Tm of from above 60° C. to about 70° C.; (4) has low cross-reactivity with non-target sequences present in the sample of interest; (5) at least the first four nucleotides (going from 3' to 5' direction) are non-complementary to any sequence within any other primer present in the same reaction; and (6) non-complementarity to any consecutive stretch of at least 5 nucleotides within any other produced target amplicon. In some embodiments, the target-specific primers used in the methods provided are selected or designed to satisfy any 2, 3, 4, 5, or 6 of the above criteria.

In some embodiments, the target-specific primers used in the methods of the invention include one or more modified nucleotides having a cleavable group. In some embodiments, the target-specific primers used in the methods of the invention include two or more modified nucleotides having cleavable groups. In some embodiments, the target-specific primers comprise at least one modified nucleotide having a cleavable group selected from methylguanine, 8-oxo-guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

In some embodiments, target amplicons using the amplification methods (and associated compositions, systems, and kits) disclosed herein, are used in the preparation of an immune receptor repertoire library. In some embodiments, the immune receptor repertoire library includes introducing adapter sequences to the termini of the target amplicon sequences. In certain embodiments, a method for preparing an immune receptor repertoire library includes generating target immune receptor amplicon molecules according to any of the multiplex amplification methods described herein, treating the amplicon molecule by digesting a modified nucleotide within the amplicon molecules' primer sequences, and ligating at least one adapter to at least one of the treated amplicon molecules, thereby producing a library of adapter-ligated target immune receptor amplicon molecules comprising the target immune receptor repertoire. In some embodiments, the steps of preparing the library are carried out in a single reaction vessel involving only addition steps. In certain embodiments, the method further includes clonally amplifying a portion of the at least one adapter-ligated target amplicon molecule.

In some embodiments, target amplicons using the methods (and associated compositions, systems, and kits) disclosed herein, are coupled to a downstream process, such as but not limited to, library preparation and nucleic acid sequencing. For example, target amplicons can be amplified using bridge amplification, emulsion PCR or isothermal amplification to generate a plurality of clonal templates suitable for nucleic acid sequencing. In some embodiments, the amplicon library is sequenced using any suitable DNA sequencing platform such as any next generation sequencing platform, including semi-conductor sequencing technology such as the Ion Torrent sequencing platform. In some embodiments, an amplicon library is sequenced using an Ion GeneStudio S5 540™ System or Ion GeneStudio S5 520™ System or an Ion GeneStudio S5 530™ System or an Ion PGM 318™ System.

In some embodiments, sequencing of immune receptor amplicons generated using the methods (and associated compositions and kits) disclosed herein, produces contiguous sequence reads from about 70 to about 200 nucleotides, about 80 to about 150 nucleotides, about 90 to about 140 nucleotides, or about 100 to about 120 nucleotides in length. In some embodiments, contiguous read lengths are from about 50 to about 170 nucleotides, about 60 to about 160 nucleotides, about 60 to about 120 nucleotides, about 70 to about 100 nucleotides, about 70 to about 90 nucleotides, or about 80 nucleotides in length. In some embodiments, read lengths average about 70, about 80, about 90, about 100, about 110, or about 120 nucleotides. In some embodiments, the sequence read length include the amplicon sequence and a barcode sequence. In some embodiments, the sequence read length does not include a barcode sequence.

In some embodiments, the amplification primers and primer pairs are target-specific sequences that can amplify specific regions of a nucleic acid molecule. In some embodiments, the target-specific primers can amplify expressed RNA or cDNA. In some embodiments, the target-specific primers can amplify mammalian RNA, such as murine RNA or cDNA prepared therefrom. In some embodiments, the target-specific primers can amplify DNA, such as gDNA. In some embodiments, the target-specific primers can amplify mammalian DNA, such as murine DNA.

In methods and compositions provided herein, for example those for determining, characterizing, and/or tracking the immune repertoire in a biological sample, the amount of input RNA or gDNA required for amplification of target sequences will depend in part on the fraction of immune receptor bearing cells (e.g., T cells or B cells) in the sample. For example, a higher fraction of T cells in the sample, such as samples enriched for T cells, permits use of a lower amount of input RNA or gDNA for amplification. In some embodiments, the amount of input RNA for amplification of one or more target sequences can be about 0.05 ng to about 10 micrograms. In some embodiments, the amount of input RNA used for multiplex amplification of one or more target sequences can be from about 5 ng to about 2 micrograms. In some embodiments, the amount of RNA used for multiplex amplification of one or more target sequences can be from about 5 ng to about 1 microgram or about 10 ng to about 1 microgram. In some embodiments, the amount of RNA used for multiplex amplification of one or more immune repertoire target sequences is about 1.5 micrograms, about 2 micrograms, about 2.5 micrograms, about 3 micrograms, about 3.5 micrograms, about 4.0 micrograms, about 5 micrograms, about 6 micrograms, about 7 micrograms, or about 10 micrograms. In some embodiments, the amount of RNA used for multiplex amplification of one or more immune repertoire target sequences is about 10 ng, about 25 ng, about 50 ng, about 100 ng, about 200 ng, about 250 ng, about 500 ng, about 750 ng, or about 1000 ng. In some embodiments, the amount of RNA used for multiplex amplification of one or more immune repertoire target sequences is from about 25 ng to about 500 ng RNA or from about 50 ng to about 200 ng RNA. In some embodiments, the amount of RNA used for multiplex amplification of one or more immune repertoire target sequences is from about 0.05 ng to about 10 ng RNA, from about 0.1 ng to about 5 ng RNA, from about 0.2 ng to about 2 ng RNA, or from about 0.5 ng to about 1 ng RNA. In some embodiments, the amount of RNA used for multiplex amplification of one or more immune repertoire target sequences is about 0.05 ng, about 0.1 ng, about 0.2 ng, about 0.5 ng, about 1.0 ng, about 2.0 ng, or about 5.0 ng.

As described herein, RNA from a biological sample is converted to cDNA, typically using reverse transcriptase in a reverse transcription reaction, prior to the multiplex amplification. In some embodiments, a reverse transcription reaction is performed with the input RNA and a portion of the cDNA from the reverse transcription reaction is used in the multiplex amplification reaction. In some embodiments, substantially all of the cDNA prepared from the input RNA is added to the multiplex amplification reaction. In other embodiments, a portion, such as about 80%, about 75%, about 66%, about 50%, about 33%, or about 25% of the cDNA prepared from the input RNA is added to the multiplex amplification reaction. In other embodiments, about 15%, about 10%, about 8%, about 6%, or about 5% of the cDNA prepared from the input RNA is added to the multiplex amplification reaction.

In some embodiments, the amount of cDNA from a sample added to the multiplex amplification reaction can be about 0.001 ng to about 5 micrograms. In some embodiments, the amount of cDNA used for multiplex amplification of one or more immune repertoire target sequences can be from about 0.01 ng to about 2 micrograms. In some embodiments, the amount of cDNA used for multiplex amplification of one or more target sequences can be from about 0.1 ng to about 1 microgram or about 1 ng to about 0.5 microgram. In some embodiments, the amount of cDNA used for multiplex amplification of one or more immune repertoire target sequences is about 0.5 ng, about 1 ng, about 5 ng, about 10 ng, about 25 ng, about 50 ng, about 100 ng, about 200 ng, about 250 ng, about 500 ng, about 750 ng, or about 1000 ng. In some embodiments, the amount of cDNA used for multiplex amplification of one or more immune repertoire target sequences is from about 0.01 ng to about 10 ng cDNA, from about 0.05 ng to about 5 ng cDNA, from about 0.1 ng to about 2 ng cDNA, or from about 0.01 ng to about 1 ng cDNA. In some embodiments, the amount of cDNA used for multiplex amplification of one or more immune repertoire target sequences is about 0.005 ng, about 0.01 ng, about 0.05 ng, about 0.1 ng, about 0.2 ng, about 0.5 ng, about 1.0 ng, about 2.0 ng, or about 5.0 ng.

In some embodiments, mRNA is obtained from a biological sample and converted to cDNA for amplification purposes using conventional methods. Methods and reagents for extracting or isolating nucleic acid from biological samples are well known and commercially available. In some embodiments, RNA extraction from biological samples is performed by any method described herein or otherwise known to those of skill in the art, e.g., methods involving proteinase K tissue digestion and alcohol-based nucleic acid precipitation, treatment with DNAse to digest contaminating DNA, and RNA purification using silica-gel-membrane technology, or any combination thereof. Exemplary methods for RNA extraction from biological samples using commercially available kits including RecoverAll™ Multi-Sample RNA/DNA Workflow (Invitrogen), RecoverAll™ Total Nucleic Acid Isolation Kit (Invitrogen), NucleoSpin® RNA blood (Macherey-Nagel), PAXgene® Blood RNA system, TRI Reagent™ (Invitrogen), PureLink™ RNA Micro Scale kit (Invitrogen), MagMAX™ FFPE DNA/RNA Ultra Kit (Applied Biosystems) ZR RNA MicroPrep™ kit (Zymo Research), RNeasy Micro kit (Qiagen), and ReliaPrep™ RNA Tissue miniPrep system (Promega).

In some embodiments, the amount of input gDNA for amplification of one or more target sequences can be about 0.1 ng to about 10 micrograms. In some embodiments, the amount of gDNA required for amplification of one or more target sequences can be from about 0.5 ng to about 5 micrograms. In some embodiments, the amount of gDNA required for amplification of one or more target sequences can be from about 1 ng to about 1 microgram or about 10 ng to about 1 microgram. In some embodiments, the amount of gDNA required for amplification of one or more immune repertoire target sequences is from about 10 ng to about 500 ng, about 25 ng to about 400 ng, or from about 50 ng to about 200 ng. In some embodiments, the amount of gDNA required for amplification of one or more target sequences is about 0.5 ng, about 1 ng, about 5 ng, about 10 ng, about 20 ng, about 50 ng, about 100 ng, or about 200 ng. In some embodiments, the amount of gDNA required for amplification of one or more immune repertoire target sequences is about 1 microgram, about 2 micrograms, about 3 micrograms, about 4.0 micrograms, or about 5 micrograms.

In some embodiments, gDNA is obtained from a biological sample using conventional methods. Methods and reagents for extracting or isolating nucleic acid from biological samples are well known and commercially available. In some embodiments, DNA extraction from biological samples is performed by any method described herein or otherwise known to those of skill in the art, e.g., methods involving proteinase K tissue digestion and alcohol-based nucleic acid precipitation, treatment with RNAse to digest contaminating RNA, and DNA purification using silica-gel-membrane technology, or any combination thereof. Exemplary methods for DNA extraction from biological samples using commercially available kits including Ion AmpliSeq™ Direct FFPE DNA Kit, MagMAX™ FFPE DNA/RNA Ultra Kit, TRI Reagent™ (Invitrogen), PureLink™ Genomic DNA Mini kit (Invitrogen), RecoverAll™ Total Nucleic Acid Isolation Kit (Invitrogen), MagMAX™ DNA Multi-Sample Kit (Invitrogen) and DNA extraction kits from BioChain Institute Inc. (e.g., FFPE Tissue DNA Extraction Kit, Genomic DNA Extraction Kit, Blood and Serum DNA Isolation Kit).

A sample or biological sample, as used herein, refers to a composition from an individual that contains or may contain cells related to the immune system. Exemplary biological samples, include without limitation, tissue (for example, lymph node, organ tissue, bone marrow), whole blood, synovial fluid, cerebral spinal fluid, tumor biopsy, and other clinical specimens containing cells. The sample may include normal and/or diseased cells and be a fine needle aspirate, fine needle biopsy, core sample, or other sample. In some embodiments, the biological sample may comprise hematopoietic cells, peripheral blood mononuclear cells (PBMCs), T cells, B cells, tumor infiltrating lymphocytes ("TILs") or other lymphocytes. In some embodiments, the sample may be fresh (e.g., not preserved), frozen, or formalin-fixed paraffin-embedded tissue (FFPE). Some samples comprise cancer cells, such as carcinomas, melanomas, sarcomas, lymphomas, myelomas, leukemias, and the like, and the cancer cells may be circulating tumor cells. In some embodiments, the biological sample comprises cell-free DNA (cfDNA), such as found, for example, in blood or plasma.

The biological sample can be a mix of tissue or cell types, a preparation of cells enriched for at least one particular category or type of cell, or an isolated population of cells of a particular type or phenotype. Samples can be separated by centrifugation, elutriation, density gradient separation, apheresis, affinity selection, panning, FACS, centrifugation with Hypaque, etc. prior to analysis. Methods for sorting, enriching for, and isolating particular cell types are well-known and can be readily carried out by one of ordinary skill. In some embodiments, the sample may a preparation enriched for T cells, for example CD3+ T cells, or may be a preparation enriched for B cells.

In some embodiments, the provided methods and systems include processes for analysis of immune repertoire receptor cDNA or gDNA sequence data and for identification and/or removing PCR or sequencing-derived error(s) from the determined immune receptor sequence.

In some embodiments, the error correction strategy includes the following steps:

1) Align the sequenced rearrangement to a reference database of variable, diversity and joining/constant genes to produce a query sequence/reference sequence pair. Many alignment procedures may be used for this purpose including, for example, IgBLAST, a freely-available tool from the NCBI, and custom computer scripts.
2) Realign the reference and query sequences to each other, taking into account the flow order used for sequencing. The flow order provides information that allows one to identify and correct some types of erroneous alignments.
3) Identify the borders of the CDR3 region by their characteristic sequence motifs.
4) Over the aligned portion of the rearrangement corresponding to the variable gene and joining/constant genes, excluding the CDR3 region, identify indels in the query with respect to the reference and alter the mismatching query base position so that it is consistent with the reference.
5) For the CDR3 region, if the CDR3 length is not a multiple of three (indicative of an indel error):
    (a) Search the CDR3 for the homopolymer stretch having the highest probability of containing a sequence error, based on PHRED score (denoted e).
    (b) Obtain the probability of error over the entire CDR3 region based on PHRED score (denoted t)
    (c) If e/t is greater than a defined threshold, edit the homopolymer by either increasing or decreasing the length of the homopolymer by one base such that the CDR3 nucleotide length is a multiple of three.
    (d) As an alternative to steps a-c, search the CDR3 for the longest homopolymer, and if the length of the homopolymer is above a defined threshold, edit the homopolymer by either increasing or decreasing the length of the homopolymer by one base such that the CDR3 nucleotide length is a multiple of three.

Figure 2:
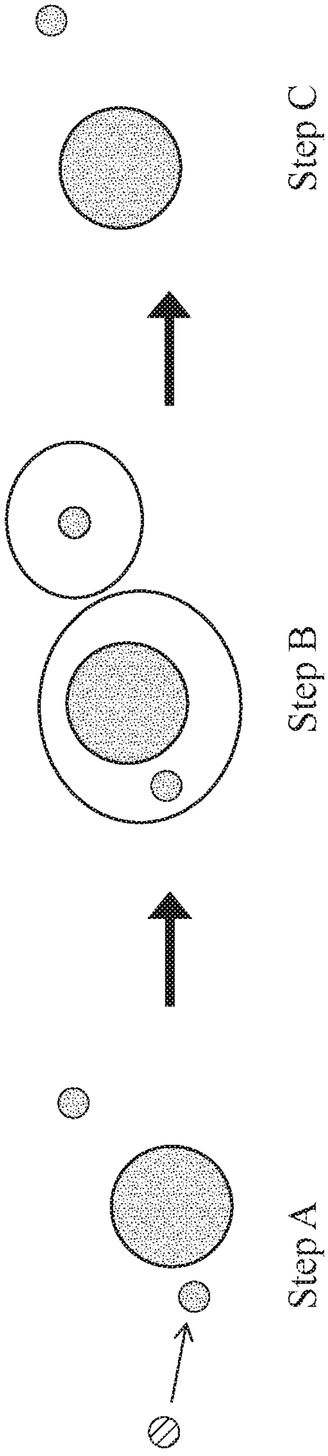
FIG. 2 is a diagram of an exemplary workflow for removal of residual insertion/deletion (indel) error by comparing homopolymer collapsed CDR3 sequences using Levenshtein distance with the steps: (A) collapse homopolymers and calculate Levenshtein distances between cluster representatives; (B) merge reads that now cluster together, these represent complex indel errors; (C) report lineages to user.

In some embodiments, methods are provided to identify T cell and/or B cell clones in repertoire data that are robust to PCR and sequencing error. Accordingly, the following describes steps that may be employed in such methods to identify T cell or B cell clones in a manner that is robust to PCR and sequencing error. Table 1 a diagram of an exemplary workflow for use in identifying and removing PCR or sequencing-derived errors from immune receptor sequencing data. Exemplary portions and embodiments of this workflow are also represented in FIGS. 1-2.

TABLE 1

| SEQUENCE CORRECTION WORKFLOW | | |
|---|---|---|
| A. Raw bam file | | |
| B. IgBLAST annotation and indel correction | → | Report high-quality fastq |
| C. Select for productive reads | → | Unproductive or off-target reads |
| D. Filter chimeras | | |
| E. Filter simple indel errors | → (D, E, F) | Frequency-based filtering |
| F. Filter singleton reads | | |
| G. Filter truncated reads | | |
| H. Filter for rearrangements with bidirectional support | | |
| I. Stepwise clustering and lineage reporting | → | Described in FIG. 1 |

For a set of TCR or BCR sequences derived from mRNA or gDNA, where 1) each sequence has been annotated as a productive rearrangement, either natively or after error correction, such as previously described, and 2) each sequence has an identified V gene and CDR3 nucleotide region, in some embodiments, methods include the following:

1) Identify and exclude chimeric sequences. For each unique CDR3 nucleotide sequence present in the dataset, tally the number of reads having that CDR3 nucleotide sequence and any of the possible V genes. Any V gene-CDR3 combination making up less than 10% of total reads for that CDR3 nucleotide sequence is flagged as a chimera and eliminated from downstream analyses. As an example, for the sequences below having the same CDR3 nucleotide sequence, e.g., the sequences having TRBV3 and TRBV6 paired with CDR3nt sequence AATTGGT will be flagged as chimeric.

| V gene | CDR3nt | Read counts |
|---|---|---|
| TRBV2 | AATTGGT | 1000 |
| TRBV3 | AATTGGT | 10 |
| TRBV6 | AATTGGT | 3 |

2) Identify and exclude sequences containing simple indel errors. For each read in the dataset, obtain the homopolymer-collapsed representation of the CDR3 sequence of that read. For each set of reads having the same V gene and collapsed-CDR3 combination, tally the number of occurrences of each non-collapsed CDR3 nucleotide sequence. Any non-collapsed CDR3 sequence making up <10% of total reads for that read set is flagged as having a simple homopolymer error. As an example, three different V gene-CDR3 nucleotide sequences are presented that are identical after homopolymer collapsing of the CDR3 nucleotide sequence. The two less frequent V gene-CDR3 combinations make up <10% of total reads for the read set and will be flagged as containing a simple indel error. For example:

| V gene | CDR3nt | Homopolymer collapsed CDR3nt | Read counts |
|---|---|---|---|
| TRBV2 | AATTGGT | ATGT | 1000 |
| TRBV2 | AAATGGT | ATGT | 10 |
| TRBV2 | AAAATTTGGT (SEQ ID NO: 1053) | ATGT | 3 |

3) Identify and exclude singleton reads. For each read in the dataset, tally the number of times that the exact read sequence is found in the dataset. Reads that appear only once in the dataset will be flagged as singleton reads.

4) Identify and exclude truncated reads. For each read in the dataset, determine whether the read possesses an annotated V gene FR1, CDR1, FR2, CDR2, and FR3 region, as indicated by the IgBLAST alignment of the read to the IgBLAST reference V gene set. Reads that do not possess the above regions are flagged as truncated if the region(s) is expected based on the particular V gene primer used for amplification.

5) Identify and exclude rearrangements lacking bidirectional support. For each read in the dataset, obtain the V gene and CDR3 sequence of the read as well as the strand orientation of the read (plus or minus strand). For each V gene-CDR3 combination in the dataset, tally the number of plus and minus strand reads having that V gene-CDR3nt combination. V gene-CDR3nt combinations that are only present in reads of one orientation will be deemed to be a spurious. All reads having a spurious V gene-CDR3nt combination will be flagged as lacking bidirectional support.

6) For genes that have not been flagged, perform stepwise clustering based on CDR3 nucleotide similarity. Separate the sequences into groups based on the V gene identity of the read, excluding allele information (v-gene groups). For each group:

a. Arrange reads in each group into clusters using cd-hit-est and the following parameters:

cd-hit-est -i vgene_groups.fa -o clustered_vgene_groups.cdhit -T 24 -d 0 -M 100000 -B 0 -r 0 -g 1 -S 0 -U 2 -uL 0.05 -n 10-1 7. (The freely available software program cd-hit-est clusters a nucleotide dataset into clusters that meet a user-defined similarity threshold. (For code and instructions on cd-hit-est, see https://github.con/weizhongli/cdhit/wiki/3.-User%27s-Guide#CDHITEST).

Where vgene_groups.fa is a fasta format file of the CDR3 nucleotide regions of sequences having the same V gene and clustered_vgene_groups.cdhit is the output, containing the subdivided sequences.

b. Assign each sequence in a cluster the same clone ID, used to denote that members of the subgroup are believed to represent the same T cell clone or B cell clone.

c. Chose a representative sequence for each cluster, such that the representative sequence is the sequence that appears the greatest number of times, or, in cases of a tie, is randomly chosen.

d. Merge all other reads in the cluster into the representative sequence such that the number of reads for the representative sequence is increased according to the number of reads for the merged sequences.

e. Compare the representative sequences within a v-gene group to each other on the basis of hamming distance. If a representative sequence is within a hamming distance of 1 to a representative sequence that is >50 times more abundant, merge that sequence into the more common representative sequence. If a representative sequence is within a hamming distance of 2 to a representative sequence that is >10000 times more abundant, merge that sequence into the more common representative sequence.

f. Identify complex sequence errors. Homopolymer-collapse the representative sequences within each V gene group, then compare to each other using Levenshtein distances. If a representative sequence is within a Levenshtein distance of 1 to a representative sequence that is >50 times more abundant, merge that sequence into the more common representative sequence.

g. Identify CDR3 misannotation errors. Homopolymer-collapse the representative sequences within each V gene group, then perform a pairwise comparison of each homopolymer-collapsed sequence. For each pair of sequences, determine whether one sequence is a subset of the other sequence. If so, merge the less abundant sequence into the more abundant sequence if the more abundance sequence is >500 fold more abundant.

7) Report cluster representatives to user.

In some embodiments, step 6 of the above workflow separates the rearrangement sequences into groups based on the V-gene identity (excluding allele information), and the CDR3 nucleotide length. In other embodiments, the J-gene identity and/or isotype identity is also used as part of the grouping criteria.

Accordingly, in some embodiments, step 6 of the above workflow includes the following steps:

a. Arrange reads in each group into clusters using cd-hit-est and the following parameters:

cd-hit-est -i vgene_groups.fa -o clustered_vgene_groups.cdhit -T 24-1 9 -d 0 -M 100000 -B0-r0-g 1 -S 15 -U 2 -uL 0.05 -n 9.

Where vgene_groups.fa is a fasta format file of the sequenced portion of the VDJ rearrangement.

In some embodiments, the full sequence of the VDJ is considered for clustering as somatic hypermutation may occur throughout the VDJ region.

b. Assign each sequence in a cluster the same clone ID, used to denote that members of the subgroup are believed to represent the same T cell clone or B cell clone.

c. Chose a representative sequence for each cluster, such that the representative sequence is the sequence that appears the greatest number of times, or, in cases of a tie, is randomly chosen.

d. Merge all other reads in the cluster into the representative sequence such that the number of reads for the representative sequence is increased according to the number of reads for the merged sequences.

e. Compare the representative sequences within a v-gene group to each other on the basis of hamming distance. If a representative sequence is within a hamming distance of 1 to a representative sequence that is >50 times more abundant, merge that sequence into the more common representative sequence. If a representative sequence is within a hamming distance of 2 to a representative sequence that is >10000 times more abundant, merge that sequence into the more common representative sequence. In some embodiments, fold thresholds of >50/3 and >10000/3, among others are used to merge sequences of hamming distances 1 or 2, respectively. Reducing the fold thresholds can be useful when comparing sequences of the entire VDJ region rather than sequences of only the CDR3 region as the longer sequence has a greater chance of accumulating amplification and/or sequencing errors.

f. Identify complex sequence errors. Homopolymer-collapse the representative sequences within each V gene group, then compare to each other using Levenshtein distances. If a representative sequence is within a Levenshtein distance of 1 to a representative sequence that is >50 times more abundant, merge that sequence into the more common representative sequence.

g. Identify CDR3 misannotation errors. Homopolymer-collapse the representative sequences within each V gene group, then perform a pairwise comparison of each homopolymer-collapsed sequence. For each pair of sequences, determine whether one sequence is a subset of the other sequence. If so, merge the less abundant sequence into the more abundant sequence if the more abundance sequence is >500 fold more abundant.

In some embodiments, the provided workflow is not limited to the frequency ratios listed in the various steps, and other frequency ratios may be substituted for the representative frequency ratios included above. The frequency ratio refers to a ratio of the abundance value of the more common representative sequence to the abundance value of the less common representative sequence. The frequency ratio threshold gives the threshold at which the less common representative sequence is merged into the more common representative sequence. For example, in some embodiments, comparing the representative sequences within a v-gene group to each other on the basis of hamming distance may use a frequency ratio other than those listed in step (e) above. For example and without limitation, frequency ratios of 1000, 5000, 20,000, etc may be used if a representative sequence is within a hamming distance of 2 to a representative sequence. For example and without limitation, frequency ratios of 20, 100, 200, etc may be used if a representative sequence is within a hamming distance of 1 to a representative sequence. The frequency ratios provided are representative of the general process of labeling the more abundant sequence of a similar pair as a correct sequence.

Similarly, when comparing the frequencies of two sequences at other steps in the workflow, eg, step (1), step (2), step (6f) and step (6g), frequency ratios other than those listed in the step above may be used.

As used herein, the term "homopolymer-collapsed sequence" is intended to represent a sequence where repeated bases are collapsed to a single base representative. As an example, for the non-collapsed sequence AAAATTTTTATCCCCCCCCGGG (SEQ ID NO: 1054), the homopolymer-collapsed sequence is ATATCG.

As used herein, the terms "clone," "clonotype," "lineage," or "rearrangement" are intended to describe a unique V gene nucleotide combination for an immune receptor, such as a TCR or BCR. For example, a unique V gene-CDR3 nucleotide combination.

As used herein, the term "productive reads" refers to a TCR or BCR sequence reads that have no stop codon and have in-frame variable gene and joining gene segments. Productive reads are biologically plausible in coding for a polypeptide.

As used herein, "chimeras" or chimeric sequences" refer to artefactual sequences that arise from template switching during target amplification, such as PCR. Chimeras typically present as a CDR3 sequence grafted onto an unrelated V gene, resulting in a CDR3 sequence that is associated with multiple V genes within a dataset. The chimeric sequence is usually far less abundant than the true sequence in the dataset.

As used herein, the term "indel" refers to an insertion and/or deletion of one or more nucleotide bases in a nucleic acid sequence. In coding regions of a nucleic acid sequence, unless the length of an indel is a multiple of 3, it will produce a frameshift when the sequence is translated. As used herein, "simple indel errors" are errors that do not alter the homopolymer-collapsed representation of the sequence. As used herein, "complex indel errors" are indel sequencing errors that alter the homopolymer-collapsed representation of the sequence and include, without limitation, errors that eliminate a homopolymer, insert a homopolymer into the sequence, or create a dyslexic-type error.

As used herein, "singleton reads" refer to sequence reads whose indel-corrected sequence appears only once in a dataset. Typically, singleton reads are enriched for reads containing a PCR or sequencing error.

As used herein, "truncated reads" refer to immune receptor sequence reads that are missing annotated V gene regions. For example, truncated reads include, without limitation, sequence reads that are missing annotated TCR or BCR V gene FR1, CDR1, FR2, CDR2, or FR3 regions. Such reads typically are missing a portion of the V gene sequence due to quality trimming. Truncated reads can give rise to artifacts if the truncation leads one to misidentify the V gene.

In the context of identified V gene-CDR3 sequences (clonotypes), "bidirectional support" indicates that a particular V gene-CDR3 sequence is found in at least one read that maps to the plus strand (proceeding from the V gene to constant gene) and at least one reads that maps to the minus strand (proceeding from the constant gene to the V gene). Systematic sequencing errors often lead to identification of V gene-CDR3 sequences having unidirectional support.

For a set of sequences that have been grouped according to a predetermined sequence similarity threshold to account for variation due to PCR or sequencing error, the "cluster representative" is the sequence that is chosen as most likely to be error free. This is typically the most abundant sequence.

As used herein, "IgBLAST annotation error" refers to rare events where the border of the CDR3 is identified to be in an incorrect adjacent position. These events typically add three bases to the 5' or 3' end of a CDR3 nucleotide sequence.

For two sequences of equal length, the "Hamming distance" is the number of positions at which the corresponding bases or amino acids are different. For any two sequences, the "Levenshtein distance" or the "edit distance" is the number of single base or amino acid edits required to make one nucleotide or amino acid sequence into another nucleotide or amino acid sequence.

In some embodiments in which J gene-directed primers are used in amplification of the immune receptor sequences, for example multiplex amplification with primers directed to V gene FR3 regions and primers directed to J genes, raw sequence reads derived from the assay undergo a J gene sequence inference process before any downstream analysis. In this process, the beginning and end of raw read sequences are interrogated for the presence of characteristic sequences of 10-30 nucleotides corresponding to the portion of the J gene sequences expected to exist after amplification with the J primer and any subsequent manipulation or processing (for example, digestion) of the amplicon termini prior to sequencing. The characteristic nucleotide sequences permit one to infer the sequence of the J primer, as well as the remaining portion of the J gene that was targeted since the sequence of each J gene is known. To complete the J gene sequence inference process, the inferred J gene sequence is added to the raw read to create an extended read that then spans the entire J gene. The extended read then contains the entire J gene sequence, the entire sequence of the CDR3 region, and at least a portion of the V gene sequence, which will be reported after downstream analysis. The portion of V gene sequence in the extended read will depend on the V gene-directed primers used for the multiplex amplification, for example, FR3-, FR2-, or FR1-directed primers.

Use of V gene FR3 and J gene primers to amplify expressed immune receptor sequences or rearranged immune receptor gDNA sequences yields a minimum length amplicon (for example, about 60-100 or about 80 nucleotides in length) while still producing data that allows for reporting of the entire CDR3 region. With the expectation of short amplicon length, reads of amplicons <100 nucleotides in length are not eliminated as low-quality and/or off target products during the sequence analysis workflow. However, the explicit search for the expected J gene sequences in the raw reads allows one to eliminate amplicons deriving from off-target amplifications by the J gene primers. In addition, this short amplicon length improves the performance of the assay on highly degraded template material, such as that derived from an FFPE sample or cfDNA.

In some embodiments, provided methods comprise sequencing an immune receptor library and subjecting the obtained sequence data to error identification and correction processes to generate rescued productive reads, and identifying productive and rescued productive sequence reads. In some embodiments, provided methods comprise sequencing an immune receptor library and subjecting the obtained sequence dataset to error identification and correction processes, identifying productive and rescued productive sequence reads, and grouping the sequence reads by clonotype to identify immune receptor clonotypes in the library.

In some embodiments, provided methods comprise sequencing a rearranged immune receptor DNA library and subjecting the obtained sequence data to error identification and correction processes for the V gene portions to generate rescued productive reads, and identifying productive, rescued productive, and unproductive sequence reads. In some embodiments, provided methods comprise sequencing a rearranged immune receptor DNA library and subjecting the obtained sequence dataset to error identification and correction processes for the V gene portions, identifying productive, rescued productive, and unproductive sequence reads, and grouping the sequence reads by clonotype to identify immune receptor clonotypes in the library. In some embodiments, both productive and unproductive sequence reads of rearranged immune receptor DNA are separately reported.

In some embodiments, the provided error identification and correction workflow is used for identifying and resolving PCR or sequencing-derived errors that lead to a sequence read being identified as from an unproductive rearrangement. In some embodiments, the provided error identification and correction workflow is applied to immune receptor sequence data generated from a sequencing platform in which indel or other frameshift-causing errors occur while generating the sequence data.

In some embodiments, the provided error identification and correction workflow is applied to sequence data generated by an Ion Torrent sequencing platform. In some embodiments, the provided error identification and correction workflow is applied to sequence data generated by Roche 454 Life Sciences sequencing platforms, PacBio sequencing platforms, and Oxford Nanopore sequencing platforms.

In some embodiments, the BCR repertoire analysis workflow includes an additional last step to identify clonal lineages in the sample. A clonal lineage represents a set of B cell clones (e.g., identified as having unique VDJ sequences) that derive from a common VDJ rearrangement but differ owing to somatic hypermutation and/or class switch recombination. It is generally assumed that members of a clonal lineage may be more likely to target the same antigen than members of different clonal lineages.

In some embodiments, the process of clonal lineage identification includes using a set of BCR clones (e.g., IgH clones) identified (for example as described herein) to perform the following:

1. Separate the clone sequences into groups where group members share the same variable gene (excluding allele information), the same CDR3 nucleotide length, and the same joining gene (excluding allele information). In some embodiments the above J-gene criterion may be omitted.
2. Arrange the clone sequences in each group into clusters based on the CDR3 nucleotide similarity of the clone sequences. Thresholds for CDR3 nucleotide similarity are about 0.70 to about 0.99. In some embodiments, the threshold for CDR3 nucleotide similarity is between about 0.80 to about 0.99. In some embodiments, the threshold for CDR3 nucleotide similarity is between about 0.80 to about 0.90. In certain embodiments, the threshold for CDR3 nucleotide similarity is about 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99.
    a. In some embodiments, the clustering is performed using cd-hit-est as described: cd-hit-est -i vgene_groups.fa -o clustered_vgene_groups.cdhit -T 24-1 9 -d 0 -M 100000 -B 0 -r 0 -g 1 -S 0 -c 0.85 -n 5, where vgene_groups.fa consists of the set of CDR3 nucleotide sequences of each clone within a group. Clones within the same cluster are considered members of the same clonal lineage.
    b. In some instances, somatic hypermutation may be extensive enough that the described clustering criteria may not group all clonal lineage members. For such cases, in some embodiments, an additional step is performed to merge clusters identified in (a). The additional step consists of searching for instances of shared somatic hypermutation-derived mutations in the variable gene between clonal lineages, then merging clonal lineages if the fraction and/or number of shared mutations is above a certain threshold. Variable gene mutations are identified by comparison of the variable gene sequence to the best matching variable gene sequence in the IMGT database, as described. In some embodiments, the threshold for number of shared mutations is 2 or more. In some embodiments, the threshold for number of shared mutations is 3 or more. In other embodiments, the threshold for number of shared mutations is 4, 5, 6, 7, 8, 9, 10 or more. In some embodiments, the fraction of shared mutations is about 0.15 to about 0.95. In some embodiments, the fraction of shared mutations is about 0.75 or about 0.85. In other embodiments, the fraction of shared mutations is about 0.15, 0.2, 0.25, 0.3, 0.35, 0.4, 0.5, 0.6, 0.7, 0.8, 0.9, or 0.95.

In some instances, a variable gene allele may be identified that is not represented in the IMGT database. In such instances, alignment to the IMGT database will indicate a mismatch that is not derived from somatic hypermutation. To avoid noise caused by such unannotated genetic variants, in some embodiments, an initial step is performed before (b) where one identifies all putative novel variable gene alleles in a sample, noting each position that differs from reference. In some embodiments, such positions are then excluded from consideration in the analysis described in (b). Methods for the identification of novel alleles from immune repertoire sequencing data have been described, for example, by Gadala-Maria et al. (2015) Proc. Natl. Acad. Sci. USA 112: E862-E870 and PCT Application Publication No. WO 2018/136562.

At the end of this clonal lineage identification process, each clone has been assigned to a clonal lineage. BCR repertoire features such as diversity, evenness, and convergence may be calculated with the clonal lineage as the unit of analysis. In some embodiments, clonal lineages features, such as the number of clones belonging to a lineage, the isotypes of those clones if identified, the maximum and minimum frequency of the clones in a lineage, the maximum and minimum variable gene somatic hypermutation in a lineage, and others, are calculated and reported to the user.

In the absence of somatic hypermutation, BCR convergence may be calculated as the frequency of clones that are identical, or functionally identical, in amino acid sequence but different in nucleotide sequence. These represent clones that independently underwent VDJ recombination and generally assumed to have proliferated in response to a common antigen. However, somatic hypermutation can create distinct VDJ sequences that do not represent B cells that independently underwent VDJ recombination. To account for this a definition of convergence is used that takes into account the clonal lineage identification. For this purpose, "BCR convergence" is defined as the frequency of B cell clones that are members of different clonal lineages, as determined above, but are similar or identical in amino acid sequence. In some embodiments, two IgH rearrangements are considered convergent if they are assigned to separate clonal lineages but have the same variable gene (excluding allele information) and the same or similar CDR3 amino acid sequence. In other embodiments where sequencing covers all three CDR domains of the IGH chain, two IgH rearrangements may be considered convergent if they are assigned to separate clonal lineages but have the same variable gene (excluding allele information) and the same or similar CDR 1, 2 and 3 amino acid sequence. In some embodiments, similar CDR amino acid sequences are within a Hamming or Levenshtein edit distance of 1. In other embodiments, similar CDR amino acid sequences are within a Hamming or Levenshtein edit distance of 2.

Accordingly, in some embodiments, functionally equivalent B cells are identified by searching for BCR clones having the same variable gene and CDR amino acid sequences that are within a Hamming or Levenshtein edit distance of 1 or 2. In some embodiments the program cd-hit may be used to identify clones having similar but functionally equivalent amino acid sequences. (For code and information on the program cd-hit, see https://github.com/weizhongli/cdhit/wiki/3.-User %27s-Guide) In some embodiments cd-hit is run using the following command:

cd-hit -i vgene_groups.fa -o clustered_vgene_groups.cdhit -T 24-1 5 -d 0 -M 100000 -B 0 -g 1 -S 1 -U 1 -n 5, where vgene_groups.fa consists of the set of CDR3 amino acid sequences of clones having the same variable gene. Clones within the same cluster are considered to be functionally equivalent.

In some embodiments, the value for the parameter -S may be 0, 1, 2, or 3. In some embodiments, the value for the parameter -U may be 0, 1, 2, or 3.

In some embodiments, vgene_groups.fa consists of the set of CDR 1, 2 and 3 amino acid sequences of clones having the same variable gene. In some embodiments, vgene_groups.fa consists of the set of clones having both the same variable gene and the same CDR3 length.

In some embodiments, provided sequence analysis workflows include a downsampling analysis. For TCR or BCR immune repertoire sequencing and subsequent analysis, use of downsampling analysis can help, for example, to eliminate variability owing to differences in sequencing depth across an assay. For example, an exemplary downsampling analysis for use with RNA or cDNA sequencing and analysis workflows applies the following procedure to the data: a) starting with the total set of productive+rescued productive reads, sequence reads are randomly removed down to one of several fixed read depths and b) this subset of reads is used to perform all downstream calculations (for example, clonotyping and calculation of secondary repertoire features including without limitation evenness, convergence, diversity, number and identity of clones detected, and clonal lineages).

In some embodiments, downsampling analysis identifies the point at which a particular sample is sequenced to saturation, for example, a point at which additional reads do not identify additional clones or lineages or add additional diversity to the detected repertoire. In some embodiments, downsampling allows the refining of sequencing depth or multiplexing among or between assays with similar sample types.

In some embodiments, provided methods comprise preparation and formation of a plurality of immune receptor-specific amplicons. In some embodiments, the method comprises hybridizing a plurality of V gene gene-specific primers and a plurality of J gene-specific primers to a cDNA molecule, extending a first primer (e.g., a V gene-specific primer) of the primer pair, denaturing the extended first primer from the cDNA molecule, hybridizing to the extended first primer product, a second primer (e.g., a J gene-specific primer) of the primer pair and extending the second primer, digesting the target-specific primer pairs to generate a plurality of target amplicons. In some embodiments, adapters are ligated to the ends of the target amplicons prior to performing a nick translation reaction to generate a plurality of target amplicons suitable for nucleic acid sequencing. In some embodiments, at least one of the ligated adapters includes at least one barcode sequence. In some embodiments, each adapter ligated to the ends of the target amplicons includes a barcode sequence. In some embodiments, the one or more target amplicons can be amplified using bridge amplification, emulsion PCR or isothermal amplification to generate a plurality of clonal templates suitable for nucleic acid sequencing.

In some embodiments, provided methods comprise preparation and formation of a plurality of immune receptor-specific amplicons. In some embodiments, the method comprises hybridizing a plurality of V gene gene-specific primers and a plurality of J gene-specific primers to a gDNA molecule, extending a first primer (eg, a V gene-specific primer) of the primer pair, denaturing the extended first primer from the gDNA molecule, hybridizing to the extended first primer product, a second primer (e.g., a J gene-specific primer) of the primer pair and extending the second primer, digesting the target-specific primer pairs to generate a plurality of target amplicons. In some embodiments, adapters are ligated to the ends of the target amplicons prior to performing a nick translation reaction to generate a plurality of target amplicons suitable for nucleic acid sequencing. In some embodiments, at least one of the ligated adapters includes at least one barcode sequence. In some embodiments, each adapter ligated to the ends of the target amplicons includes a barcode sequence. In some embodiments, the one or more target amplicons can be amplified using bridge amplification or emulsion PCR to generate a plurality of clonal templates suitable for nucleic acid sequencing.

In some embodiments, the disclosure provides methods for sequencing target amplicons and processing the sequence data to identify productive immune receptor rearrangements expressed in the biological sample from which the cDNA was derived. In other embodiments, the disclosure provides methods for sequencing target amplicons and processing the sequence data to identify productive immune receptor gene rearrangements gDNA from a biological sample. In embodiments in which J gene-directed primers are used to amplify the expressed immune receptor sequences or rearranged immune receptor gDNA sequences, processing the sequence data includes inferring the nucleotide sequence of the J gene primer used for amplification as well as the remaining portion of the J gene that was targeted, as described herein. In some embodiments, processing the sequence data includes performing provided error identification and correction steps to generate rescued productive sequences. In some embodiments, use of the provided error identification and correction workflow can result in a combination of productive reads and rescued productive reads being at least 50% of the sequencing reads for an immune receptor cDNA or gDNA sample. In some embodiments, use of the provided error identification and correction workflow can result in a combination of productive reads and rescued productive reads being at least 60%, at least 70%, at least 80%, at least 90%, or at least 95% of the sequencing reads for an immune receptor cDNA or gDNA sample. In some embodiments, use of the provided error identification and correction workflow can result in a combination of productive reads and rescued productive reads being about 50-60%, about 60-70%, about 70-80%, about 80-90%, about 50-80%, or about 60-90% of the sequencing reads for an immune receptor cDNA or gDNA sample. In some embodiments, use of the provided error identification and correction workflow can result in a combination of productive reads and rescued productive reads averaging about 50%, about 55%, about 60%, about 65%, about 70%, about 75%, about 80%, about 85%, about 90% of the sequencing reads for an immune receptor cDNA or gDNA sample.

With particular samples, the provided error identification and correction workflow can result in a combination of productive reads and rescued productive reads being less than 50% of the sequencing reads for an immune receptor cDNA or gDNA sample when particular samples are used. Such samples include, for example, those in which the RNA or gDNA is highly degraded such as FFPE samples and cfDNA samples, and those in which the number of target immune cells is very low such as, for example, samples with very low B cell count or very low T cell count or samples from subjects experiencing severe leukopenia. Accordingly, in some embodiments, use of the provided error identification and correction workflow can result in a combination of productive reads and rescued productive reads being about 30-50%, about 40-50%, about 30-40%, about 40-60%, at least 30%, or at least 40% of the sequencing reads for an immune receptor cDNA or gDNA sample.

In certain embodiments, methods of the invention comprise the use of target immune receptor primer sets wherein the primers are directed to sequences of the same target immune receptor gene, e.g, BCR (immunoglobulin) and TCR genes. Immune receptors are selected from T cell receptors and antibody receptors. In some embodiments a T cell receptor is a T cell receptor selected from the group consisting of TCR alpha, TCR beta, TCR gamma, and TCR delta. In some embodiments the immune receptor is an antibody receptor selected from the group consisting of heavy chain alpha, heavy chain delta, heavy chain epsilon, heavy chain gamma, heavy chain mu, light chain kappa, and light chain lambda. In some embodiments, methods of the invention comprise the use of target immune receptor primer sets wherein at least one of the primer sets is directed to sequences of a BCR and another primer set is directed to sequences of a TCR, and both the BCR and TCR target nucleic acids from a sample are amplified in a single multiplex amplification reaction.

In certain embodiments, provided is a method for amplification of expression nucleic acid or rearranged gDNA sequences of an immune receptor repertoire in a sample, comprising performing a multiplex amplification reaction to amplify immune receptor nucleic acid template molecules having a J gene portion and a V gene portion using at least one set of: i) a plurality of V gene primers directed to a majority of different V genes of an immune receptor coding sequence comprising at least a portion of a framework region within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In particular embodiments the one or more plurality of J gene primers of ii) are directed to sequences over about a 50 nucleotide portion of the J gene. In more particular embodiments the one or more plurality of J gene primers of ii) are directed to sequences over about a 30 nucleotide portion of the J gene. In certain embodiments, the one or more plurality of J gene primers of ii) are directed to sequences completely within the J gene.

In certain embodiments, methods are provided for providing sequence information of the immune repertoire in a sample, comprising performing a multiplex amplification reaction to amplify immune receptor nucleic acid template molecules having a J gene portion and a V gene portion using at least one set of primers comprising i) a plurality of V gene primers directed to a majority of different V gene of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence information of the immune repertoire in the sample. In some embodiments, determining the sequence of the immune receptor amplicon molecules includes obtaining initial sequence reads, aligning the initial sequence read to a reference sequence, identifying productive reads, correcting one or more indel errors to generate rescued productive sequence reads, and determining the sequences of the resulting immune receptor molecules. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads, and determining the sequences of the resulting immune receptor molecules. In particular embodiments the combination of productive reads and rescued productive reads is at least 50%, at least 60% at least 70% or at least 75% of the sequencing reads for the immune receptors. In additional embodiments the method further comprises sequence read clustering and immune receptor clonotype reporting. In some embodiments, the sequences of the identified immune repertoire are compared to a contemporaneous or current version of the IMGT database and the sequence of at least one allelic variant absent from that IMGT database is identified. In some embodiments the sequence read lengths are about 60 to about 185 nucleotides, depending in part on inclusion of any barcode sequence in the read length. In some embodiments the average sequence read length is between 70 and 90 nucleotides, or is between about 75 and about 85 nucleotides, or is about 80 nucleotides. In certain embodiments at least one set of the sequenced amplicons includes complementarity determining region CDR3 of an immune receptor expression sequence or rearranged gDNA sequence.

In certain embodiments, provided is a method for amplification of expression nucleic acid or rearranged gDNA sequences of a TCR repertoire in a sample, comprising performing a multiplex amplification reaction to amplify a TCR nucleic acid template molecules having a J gene portion and a V gene portion using at least one set of: i) a plurality of V gene primers directed to a majority of different V genes of at least one TCR coding sequence comprising at least a portion of framework region 3 (FR3) within the V gene, and ii) a plurality of J gene primers directed to a majority of different J genes of the respective target TCR coding sequence, wherein each set of i) and ii) primers directed to the same target TCR sequences and wherein performing amplification using each set results in amplicons representing the entire repertoire of the respective TCR in the sample; thereby generating immune receptor amplicons comprising the TCR repertoire. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In more particular embodiments the one or more plurality of V gene primers of i) are directed to sequences over about a 40 to about a 60 nucleotide portion of the framework region. In some embodiments the one or more plurality of V gene primers of i) anneal to at least a portion of the framework 3 region of the template molecules. In certain embodiments the plurality of J gene primers of ii) comprises at least ten primers that anneal to at least a portion of the J gene portion of the template molecules. In some embodiments the plurality of J gene primers of ii) comprises about 17 primers that anneal to at least a portion of the J gene portion of the template molecules. In some embodiments the plurality of J gene primers of ii) comprises about 12 to about 22 primers that anneal to at least a portion of the J gene portion of the template molecules. In some embodiments the plurality of J gene primers of ii) comprises about 15 to about 20 primers that anneal to at least a portion of the J gene portion of the template molecules. In particular embodiments at least one set of the generated amplicons includes complementarity determining region CDR3 of a TCR expression sequence or rearranged gDNA sequence. In some embodiments the amplicons are about 60 to about 160 nucleotides in length, about 70 to about 100 nucleotides in length, at least about 70 to about 90 nucleotides in length, about 80 to about 90 nucleotides in length, or about 80 nucleotides in length. In some embodiments the nucleic acid template used in methods is cDNA produced by reverse transcribing nucleic acid molecules extracted from a biological sample.

In particular embodiments, methods provided utilize target TCR (e.g., TCR beta or TRB) primer sets comprising V gene primers wherein the one or more of a plurality of V gene primers are directed to sequences over an FR3 region about 50 nucleotides in length. In other embodiments the one or more of a plurality of V gene primers are directed to sequences over an FR3 region about 70 nucleotides in length. In other particular embodiments the one or more of a plurality of V gene primers are directed to sequences over an FR3 region about 40 to about 60 nucleotides in length. In some embodiments a target TCR primer set comprises V gene primers comprising about 25 to about 40 different FR3-directed primers. In certain embodiments a target TCR primer set comprises V gene primers comprising about 28 to about 38 different FR3-directed primers. In some embodiments, a target TCR primer set comprises V gene primers comprising about 35 to about 60 different FR3-directed primers. In some embodiments, a target TCR primer set comprises V gene primers comprising about 29, 31, 33, 35, 37, or 40 different FR3-directed primers. In some embodiments the target TCR primer set comprises a plurality of J gene primers. In some embodiments a target TCR primer set comprises at least ten J gene primers wherein each is directed to at least a portion of a J gene within target polynucleotides. In some embodiments a target TCR primer set comprises at least 15 J gene primers wherein each is directed to at least a portion of a J gene within target polynucleotides. In some embodiments a target TCR primer set comprises about 12 to about 22 different J gene primers wherein each is directed to at least a portion of a J gene within target polynucleotides. In some embodiments a target TCR primer set comprises about 15 to about 20 different J gene primers wherein each is directed to at least a portion of a J gene within target polynucleotides. In some embodiments a target TCR primer set comprises about 13, 15, 17 or 19 different J gene primers.

In particular embodiments, methods of the invention comprise the use of at least one set of primers comprising V gene primers i) and J gene primers ii) selected from Tables 2 and 3, respectively. In certain other embodiments methods of the invention comprise the use of at least one set of primers i) and ii) comprising primers selected from SEQ ID NOs: 1-33 and 67-83 or selected from SEQ ID NOs: 34-66 and 84-100. In certain other embodiments methods of the invention comprise the use of at least one set of primers i) and ii) comprising primers selected from SEQ ID NOs: 1-33 and 84-100 or selected from SEQ ID NOs: 34-66 and 67-83.

In some embodiments methods of the invention comprise the use of at least one set of primers i) and ii) comprising at least 25 primers selected from SEQ ID NOs: 34-66 and at least 11 primers, at least 13 primers, at least 15 primers, or at least 17 primers selected from SEQ ID NOs: 84-100. In some embodiments methods of the invention comprise the use of at least one set of primers i) and ii) comprising at least 25 primers selected from SEQ ID NOs: 1-33 and at least 11 primers, at least 13 primers, at least 15 primers, or at least 17 primers selected from SEQ ID NOs: 67-83. In some embodiments methods of the invention comprise the use of at least one set of primers i) and ii) comprising at least 25 primers selected from SEQ ID NOs: 34-66 and at least 11 primers, at least 13 primers, at least 15 primers, or at least 17 primers selected from SEQ ID NOs: 67-83. In some embodiments methods of the invention comprise the use of at least one set of primers i) and ii) comprising at least 25 primers selected from SEQ ID NOs: 1-33 and at least 11 primers, at least 13 primers, at least 15 primers, or at least 17 primers selected from SEQ ID NOs: 84-100.

In certain embodiments, provided is a method for amplification of expression nucleic acid or rearranged gDNA sequences of a BCR repertoire in a sample, comprising performing a multiplex amplification reaction to amplify BCR nucleic acid template molecules having a J gene portion and a V gene portion using at least one set of: i) a plurality of V gene primers directed to a majority of different V genes of at least one BCR coding sequence comprising at least a portion of framework region 3 (FR3) within the V gene, and ii) a plurality of J gene primers directed to a majority of different J genes of the respective target BCR coding sequence, wherein each set of i) and ii) primers directed to the same target BCR sequences, and wherein performing amplification using each set results in amplicons representing the entire repertoire of the respective BCR in the sample; thereby generating BCR amplicons comprising the BCR repertoire. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In more particular embodiments the one or more plurality of V gene primers of i) are directed to sequences over about a 40 to about a 60 nucleotide portion of the framework region. In some embodiments the one or more plurality of V gene primers of i) anneal to at least a portion of the framework 3 region of the template molecules. In certain embodiments the plurality of J gene primers of ii) comprises at least one primer that anneals to at least a portion of the J gene portion of the template molecules. In some embodiments the plurality of J gene primers of ii) comprises at least 2 to about 12 primers that anneal to at least a portion of the J gene portion of the template molecules. In some embodiments the plurality of J gene primers of ii) comprises about 7 primers that anneal to at least a portion of the J gene portion of the template molecules. In some embodiments the plurality of J gene primers of ii) comprises about 4 to about 8 primers that anneal to at least a portion of the J gene portion of the template molecules. In particular embodiments at least one set of the generated amplicons includes complementarity determining region CDR3 of a BCR expression sequence. In some embodiments the amplicons are about 60 to about 160 nucleotides in length, about 70 to about 100 nucleotides in length, about 100 to about 120 nucleotides in length, at least about 70 to about 90 nucleotides in length, about 80 to about 90 nucleotides in length, or about 80 nucleotides in length. In some embodiments the nucleic acid template used in methods is cDNA produced by reverse transcribing nucleic acid molecules extracted from a biological sample.

In particular embodiments, methods provided utilize target BCR (e.g., IgH) primer sets comprising V gene primers wherein the one or more of a plurality of V gene primers are directed to sequences over an FR3 region about 50 nucleotides in length. In other embodiments the one or more of a plurality of V gene primers are directed to sequences over an FR3 region about 70 nucleotides in length. In other particular embodiments the one or more of a plurality of V gene primers are directed to sequences over an FR3 region about 40 to about 60 nucleotides in length. In certain embodiments a target BCR primer set comprises V gene primers comprising about 70 to about 120 different FR3-directed primers. In certain embodiments a target BCR primer set comprises V gene primers comprising about 80 to about 105 different FR3-directed primers. In some embodiments, a target BCR primer set comprises V gene primers comprising about 85 to about 95 different FR3-directed primers. In some embodiments, a target BCR primer set comprises V gene primers comprising about 85, 86, 87, 88, 89, 90, 91, 92, 93, 94 or 95 different FR3-directed primers. In some embodiments the target BCR primer set comprises a plurality of J gene primers. In some embodiments a target BCR primer set comprises at least one J gene primers wherein each is directed to at least a portion of a J gene within target polynucleotides. In some embodiments a target BCR primer set comprises 2 to about 12 J gene primers wherein each is directed to at least a portion of a J gene within target polynucleotides. In some embodiments a target BCR primer set comprises about 4 to about 8 different J gene primers wherein each is directed to at least a portion of a J gene within target polynucleotides. In some embodiments a target BCR primer set comprises about 3, 4, 5, 6, 7, 8, or 9 different J gene primers. In particular embodiments a target BCR primer set comprises about 7 J gene primers wherein each is directed to at least a portion of a J gene within target polynucleotides.

In particular embodiments, methods of the invention comprise the use of at least one set of primers comprising V gene primers i) and J gene primers ii) selected from Tables 4 and 5, respectively. In certain other embodiments methods of the invention comprise the use of at least one set of primers i) and ii) comprising primers selected from SEQ ID NOs: 101-541 and 983-1017 or selected from SEQ ID NOs: 542-982 and 1018-1052. In certain other embodiments methods of the invention comprise the use of at least one set of primers i) and ii) comprising primers selected from SEQ ID NOs: 101-541 and 1018-1052 or selected from SEQ ID NOs: 542-982 and 983-1017.

In some embodiments methods of the invention comprise the use of at least one set of primers i) and ii) comprising at least 85 primers selected from SEQ ID NOs: 101-541 and at least 3 primers, at least 5 primers, or at least 7 primers selected from SEQ ID NOs: 983-1017. In some embodiments methods of the invention comprise the use of at least one set of primers i) and ii) comprising at least 85 primers selected from SEQ ID NOs: 542-982 and at least 3 primers, at least 5 primers, or at least 7 primers selected from SEQ ID NOs: 1018-1052. In some embodiments methods of the invention comprise the use of at least one set of primers i) and ii) comprising at least 85 primers selected from SEQ ID NOs: 101-541 and at least 3 primers, at least 5 primers, or at least 7 primers selected from SEQ ID NOs: 1018-1052. In some embodiments methods of the invention comprise the use of at least one set of primers i) and ii) comprising at least 85 primers selected from SEQ ID NOs: 542-982 and at least 3 primers, at least 5 primers, or at least 7 primers selected from SEQ ID NOs: 983-1017.

In some embodiments methods provided comprise the use of at least one set of primers i) and ii) comprising at least 85 primers selected from SEQ ID NOs: 101-281 and at least 3 primers, at least 5 primers, or at least 7 primers selected from SEQ ID NOs: 983-996. In some embodiments methods provided comprise the use of at least one set of primers i) and ii) comprising at least 85 primers selected from SEQ ID NOs: 193-367 and at least 3 primers, at least 5 primers, or at least 7 primers selected from SEQ ID NOs: 990-1003. In some embodiments methods provided comprise the use of at least one set of primers i) and ii) comprising at least 85 primers selected from SEQ ID NOs: 282-453 and at least 3 primers, at least 5 primers, or at least 7 primers selected from SEQ ID NOs: 997-1010. In some embodiments methods provided comprise the use of at least one set of primers i) and ii) comprising at least 85 primers selected from SEQ ID NOs: 368-541 and at least 3 primers, at least 5 primers, at least 7 primers selected from SEQ ID NOs: 1004-1017.

In some embodiments methods provided comprise the use of at least one set of primers i) and ii) comprising at least 85 primers selected from SEQ ID NOs: 542-722 and at least 3 primers, at least 5 primers, or at least 7 primers selected from SEQ ID NOs: 1018-1031. In some embodiments methods provided comprise the use of at least one set of primers i) and ii) comprising at least 85 primers selected from SEQ ID NOs: 634-808 and at least 3 primers, at least 5 primers, or at least 7 primers selected from SEQ ID NOs: 1025-1038. In some embodiments methods provided comprise the use of at least one set of primers i) and ii) comprising at least 85 primers selected from SEQ ID NOs: 723-894 and at least 3 primers, at least 5 primers, or at least 7 primers selected from SEQ ID NOs: 1032-1045. In some embodiments methods provided comprise the use of at least one set of primers i) and ii) comprising at least 85 primers selected from SEQ ID NOs: 809-982 and at least 3 primers, at least 5 primers, at least 7 primers selected from SEQ ID NOs: 1039-1052.

In certain embodiments, methods of the invention comprise use of a biological sample selected from the group consisting of hematopoietic cells, lymphocytes, and tumor cells. In some embodiments the biological sample is selected from the group consisting of peripheral blood mononuclear cells (PBMCs), T cells, B cells, circulating tumor cells, and tumor infiltrating lymphocytes (herein "TILs" or "TIL"). In some embodiments, the biological sample comprises T cells undergoing ex vivo activation and/or expansion. In some embodiments, the biological sample comprises B cells undergoing ex vivo activation and/or expansion. In some embodiments, the biological sample comprises cfDNA, such as found, for example, in blood or plasma.

In some embodiments, methods, compositions, and systems are provided for determining the immune repertoire of a biological sample by assessing both expressed immune receptor RNA and rearranged immune receptor genomic DNA (gDNA) from a biological sample. The sample gDNA and expression nucleic acid sequences of a sample may be assessed using the methods, compositions, and systems provided herein. In some embodiments, the sample RNA and gDNA may be assessed concurrently and following reverse transcription of the RNA to form cDNA, the cDNA and gDNA may be amplified in the same multiplex amplification reaction. In some embodiments, cDNA from the sample RNA and the sample gDNA may undergo multiplex amplification in separate reactions. In some embodiments, cDNA from the sample RNA and sample gDNA may under multiplex amplification with parallel primer pools. In some embodiments, the same immune receptor-directed primer pools are used to assess the immune repertoire of gDNA and RNA from the sample. In some embodiments, the different immune receptor-directed primer pools are used to assess the immune repertoire of gDNA and RNA from the sample. In some embodiments, multiplex amplification reactions are performed separately with cDNA from the sample RNA and with sample gDNA to amplify target immune receptor molecules from the sample and the resulting immune receptor amplicons are sequenced, thereby providing sequence of the expressed immune receptor RNA and rearranged immune receptor gDNA of a biological sample. In some embodiments, multiplex amplification reactions are performed with a set of IgH amplification primers and a set of TCR beta amplification primers provided herein. The ability to assess both the BCR (e.g., IgH) and TCR (e.g., TCR beta) repertoires from a sample using a single multiplex amplification reaction is useful in saving time and limited biological sample and is applicable in many of the methods described herein, including methods related to allergy and autoimmunity, vaccine development and use and immuno-oncology.

In some embodiments, the methods and compositions provided are used to identify and/or characterize an immune repertoire of a subject. In some embodiments, methods and compositions provided are used to identify and characterize novel or non-canonical TCR or BCR alleles of a subject's immune repertoire. In some embodiments, the sequences of the identified immune repertoire are compared to a contemporaneous or current version of the IMGT database and the sequence of at least one allelic variant absent from that IMGT database is identified. In some embodiments, identified allelic variants absent from the IMGT database are subjected to evidence-based filtering using, for example, criteria such as clone number support, sequence read support and/or number of individuals having the allelic variant. Allelic variants identified and reported as absent from IMGT may be compared to other databases containing immune repertoire sequence information, such as NCBI NR database and Lym1K database, to cross-validate the reported novel or non-canonical TCR or BCR alleles. Characterizing the existence of undocumented or non-canonical TRB polymorphism or IgH polymorphism, for example, may help with understanding factors that influence autoimmune reactions, infectious disease, and response to immunotherapy. Thus, in some embodiments, methods and compositions are provided to identify novel or non-canonical TRBV gene allele polymorphisms and allelic variants that may predict or detect autoimmune disease or immune-mediated adverse events. In other embodiments, provided are methods for making recombinant nucleic acids encoding identified novel TRBV allelic variants. In some embodiments, provided are methods for making recombinant TRBV allelic variant molecules and for making recombinant cells which express the same. In other embodiments, provided are methods for making recombinant nucleic acids encoding identified novel IgH allelic variants. In some embodiments, provided are methods for making recombinant IgH allelic variant molecules and for making recombinant cells which express the same.

In some embodiments, methods and compositions provided are used to identify and characterize novel or non-canonical BCR alleles of a subject's immune repertoire. In some embodiments, a subject's immune repertoire may be identified or characterized before and/or after administration of a therapeutic treatment, for example treatment for a cancer or immune disorder. In some embodiments, identification or characterization of an immune repertoire may be used to assess the effect or efficacy of a treatment, to modify therapeutic regimens, and to optimize the selection of therapeutic agents. In some embodiments, identification or characterization of the immune repertoire may be used to assess a subject's response to an immunotherapy, a cancer vaccine and/or other immune-based treatment or combination(s) thereof. In some embodiments, identification or characterization of the immune repertoire may indicate a subject's likelihood to respond to a therapeutic agent or may indicate a subject's likelihood to not be responsive to a therapeutic agent.

In some embodiments, a subject's immune repertoire may be identified or characterized to monitor progression and/or treatment of hyperproliferative diseases, including detection of residual disease following disease treatment, monitor progression and/or treatment of autoimmune disease, transplantation monitoring, and to monitor conditions of antigenic stimulation, including following vaccination, exposure to bacterial, fungal, parasitic, or viral antigens, or infection by bacteria, fungi, parasites or virus. In some embodiments, identification or characterization of the immune repertoire may be used to assess a subject's response to an anti-infective or anti-inflammatory therapy.

In certain embodiments, the methods and compositions provided are used to monitor changes in TCR or BCR repertoire clonal populations and clonal lineages, for example changes in clonal expansion, changes in clonal contraction, changes in relative ratios of clones or clonal populations within a repertoire, changes in expansion or contraction of clonal lineages, changes in somatic hypermutation. In some embodiments, the provided methods and compositions are used to monitor changes in TCR or BCR repertoire clonal populations (e.g., clonal population or lineage expansion, clonal population or lineage contraction, clonal population or lineage changes in relative ratios, changes in somatic hypermutation) in response to tumor growth. In some embodiments, the provided methods and compositions are used to monitor changes in TCR or BCR repertoire clonal populations (e.g., clonal population or lineage expansion, clonal population or lineage contraction, clonal population or lineage changes in relative ratios, changes in somatic hypermutation) in response to tumor treatment. In some embodiments, the provided methods and compositions provided are used to monitor changes in immune repertoire clonal populations (e.g., clonal population or lineage expansion, clonal population or lineage contraction, clonal population or lineage changes in relative ratios, changes in somatic hypermutation) during a remission period. For many lymphoid malignancies, a clonal B cell receptor or T cell receptor sequence can be used a biomarker for the malignant cells of the particular cancer (e.g., leukemia) and to monitor residual disease, tumor expansion, contraction, and/or treatment response. In certain embodiments a clonal B cell receptor or T cell receptor may be identified and further characterized to confirm a new utility in therapeutic, biomarker and/or diagnostic use.

In some embodiments, methods and compositions are provided for identifying and/or characterizing immune repertoire clonal populations in a sample from a subject, comprising performing one or more multiplex amplification reactions with the sample or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of FR3 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying one or more immune repertoire clonal populations for the target immune receptor from the sample. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads, and determining the sequences of the resulting immune receptor molecules. In some embodiments, methods are provided to identify and/or screen for a biomarker for a disease or condition in a subject comprising identifying BCR and/or TCR clonal populations from the determined sequences of target immune receptor molecules and then identifying the sequence of at least one BCR or TCR clone for use as a biomarker for the disease or condition. Exemplary diseases or conditions, for example adverse conditions or pre-conditions, are provided herein.

In some embodiments, methods and compositions provided are used to identify and/or characterize somatic hypermutations (SHM) within a BCR repertoire or clonal populations. In some embodiments, methods and compositions provided are used to identify and/or screen for rare BCR clones or subclones, for example those having somatically hypermutated VDJ rearrangements. In some embodiments, methods for identifying and/or characterizing BCR clonal lineages and SHM comprise performing one or more multiplex amplification reaction with a subject's sample to amplify BCR nucleic acid template molecules having a J gene portion and a variable portion using at least one set of primers directed to a majority of different V genes of at least one BCR coding sequence comprising at least a portion of FR3 within the V gene, and a plurality of J gene primers directed to a majority of different J genes of the respective target BCR coding sequence, sequencing the resultant BCR amplicons, and performing VDJ sequence analysis provided herein to identify SHM and clonal lineages for the target BCR from the sample.

In some embodiments, methods and compositions are provided for monitoring changes in immune repertoire clonal populations in a subject, comprising performing one or more multiplex amplification reaction with a subject's sample to amplify immune repertoire nucleic acid template molecules having a J gene portion and a V gene portion using at least one set of primers directed to a majority of different V genes of at least one immune receptor coding sequence comprising at least a portion of FR3 within the V gene, and ii) a plurality of J gene primers directed to a majority of different J genes of the respective target immune receptor coding sequence, sequencing the resultant immune receptor amplicons, identifying immune repertoire clonal populations for the target immune receptor from the sample, and comparing the identified immune repertoire clonal populations to those identified in samples obtained from the subject at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire clonal populations include, without limitation, samples obtained prior to a disease onset, samples obtained at any stage of disease, samples obtained during a remission, samples obtained at any time prior to a treatment (pre-treatment sample), samples obtained at any time following completion of treatment (post-treatment sample), and samples obtained during the course of treatment.

In some embodiments, methods and compositions are provided for identifying and/or characterizing the immune repertoire of a subject to monitor progression and/or treatment of the subject's hyperproliferative disease, comprising performing one or more multiplex amplification reaction with a sample from the subject or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads; and determining the sequences of the resulting immune receptor molecules.

In certain embodiments, the methods and compositions provided are used to characterize and/or monitor immune repertoires associated with immune system-mediated adverse event(s), including without limitation, those associated with inflammatory conditions, autoimmune reactions, and/or autoimmune diseases or disorders. In some embodiments, the methods and compositions provided are used to identify and/or monitor T cell and/or B cell immune repertoires associated with chronic autoimmune diseases or disorders including, without limitation, multiple sclerosis, Type I diabetes, narcolepsy, rheumatoid arthritis, ankylosing spondylitis, asthma, and SLE or murine disease models based on the same. In some embodiments, a systemic sample, such as a blood sample, is used to determine the immune repertoire(s) of an individual with an autoimmune condition. In some embodiments, a localized sample, such as a fluid sample from an affected joint or region of swelling, is used to determine the immune repertoire(s) of an individual with an autoimmune condition. In some embodiments, comparison of the immune repertoire found in a localized or affected area sample to the immune repertoire found in the systemic sample can identify clonal T or B cell populations to be targeted for removal.

In some embodiments, methods and compositions are provided for identifying and/or monitoring an immune repertoire associated with a immune system-mediated adverse event(s), comprising performing one or more multiplex amplification reactions with a sample from the subject or with cDNA prepared from the sample to amplify immune repertoire nucleic acid template molecules having a J gene portion and a V gene portion using at least one set of primers comprising i) a plurality of V gene primers directed to a majority of different V genes of at least one immune receptor coding sequence comprising at least a portion of FR3 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample to an identified immune repertoire from a sample from the subject obtained at a different time. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, correcting one or more indel errors to generate rescued productive sequence reads; and determining the sequences of the resulting immune receptor molecules.

In some embodiments, methods and compositions are provided for identifying and/or monitoring an immune repertoire associated with progression and/or treatment of a subject's immune system-mediated adverse event(s), comprising performing one or more multiplex amplification reactions with a subject's sample to amplify immune repertoire nucleic acid template molecules having a J gene portion and a V gene portion using at least one set of primers directed to a majority of different V genes of at least one immune receptor coding sequence comprising at least a portion of FR3 within the V gene, and ii) a plurality of J gene primers directed to a majority of different J genes of the respective target immune receptor coding sequence, sequencing the resultant immune receptor amplicons, identifying immune repertoire sequences for the target immune receptor from the sample, and comparing the identified immune repertoire to the immune repertoire(s) identified in samples obtained from the subject at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire associated with immune system-mediated adverse event(s) include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In some embodiments, the methods and compositions provided are used to characterize and/or monitor immune repertoires associated with active immunity or vaccination therapies. For example, following exposure to a vaccine or infectious agent, the methods and compositions provided may be used to identify and/or monitor protective antibodies or protective clonal B cell or T cell populations that may provide active immunity to the exposed individual. In some embodiments, the methods and compositions provided are used to monitor the duration of B or T cell clones which contribute to immunity in an exposed individual. In some embodiments, the methods and compositions provided are used to identify and/or monitor B cell and/or T cell immune repertoires associated with exposure to bacterial, fungal, parasitic, or viral antigens. In some embodiments, the methods and compositions provided are used to identify and/or monitor B cell and/or T cell immune repertoires associated with bacterial, fungal, parasitic, or viral infection.

In some embodiments, the methods and compositions provided are used to screen or characterize lymphocyte populations which are grown and/or activated in vitro for use as immunotherapeutic agents or in immunotherapeutic-based regimens. In some embodiments, the methods and compositions provided are used to screen or characterize TIL populations or other harvested T cell populations which are grown and/or activated in vitro, for example, TILs or other harvested T cells grown and/or activated for use in adoptive immunotherapy. In some embodiments, the methods and compositions provided are used to screen or characterize CAR-T populations or other engineered T cell populations which are grown and/or activated in vitro.

In some embodiments, the methods and compositions provided are used to assess cell populations by monitoring immune repertoires during ex vivo workflows for manufacturing engineered T cell preparations, for example, for quality control or regulatory testing purposes.

In some embodiments, profiling immune receptor repertoires as provided herein may be combined with profiling immune response gene expression to provide characterization of the tumor microenvironment. In some embodiments, combining or correlating a tumor sample's immune receptor repertoire profile with a targeted immune response gene expression profile provides a more thorough analysis of the tumor microenvironment and may suggest or provide guidance for immunotherapy treatments.

Suitable cells for analysis include, without limitation, various hematopoietic cells, lymphocytes, and tumor cells, such as peripheral blood mononuclear cells (PBMCs), T cells, B cells, circulating tumor cells, and tumor infiltrating lymphocytes (TILs). Lymphocytes expressing immunoglobulin include pre-B cells, B-cells, e.g. memory B cells, and plasma cells. Lymphocytes expressing T cell receptors include thymocytes, NK cells, pre-T cells and T cells, where many subsets of T cells are known in the art, e.g. Th1, Th2, Th17, CTL, T reg, etc. For example, in some embodiments, a sample comprising PBMCs may be used as a source for TCR and/or antibody immune repertoire analysis. The sample may contain, for example, lymphocytes, monocytes, and macrophages as well as antibodies and other biological constituents.

Analysis of the immune repertoire is of interest for conditions involving cellular proliferation and antigenic exposure, including without limitation, the presence of cancer, exposure to cancer antigens, exposure to antigens from an infectious agent, exposure to vaccines, exposure to allergens, exposure to food stuffs, presence of a graft or transplant, and the presence of autoimmune activity or disease. Conditions associated with immunodeficiency are also of interest for analysis, including congenital and acquired immunodeficiency syndromes.

B cell lineage malignancies of interest include, without limitation, multiple myeloma; acute lymphocytic leukemia (ALL); relapsed/refractory B cell ALL, chronic lymphocytic leukemia (CLL); diffuse large B cell lymphoma; mucosa-associated lymphatic tissue lymphoma (MALT); small cell lymphocytic lymphoma; mantle cell lymphoma (MCL); Burkitt lymphoma; mediastinal large B cell lymphoma; Waldenström macroglobulinemia; nodal marginal zone B cell lymphoma (NMZL); splenic marginal zone lymphoma (SMZL); intravascular large B-cell lymphoma; primary effusion lymphoma; lymphomatoid granulomatosis, etc. Non-malignant B cell hyperproliferative conditions include monoclonal B cell lymphocytosis (MBL).

T cell lineage malignancies of interest include, without limitation, precursor T-cell lymphoblastic lymphoma; T-cell prolymphocytic leukemia; T-cell granular lymphocytic leukemia; aggressive NK cell leukemia; adult T-cell lymphoma/leukemia (HTLV 1-positive); extranodal NK/T-cell lymphoma; enteropathy-type T-cell lymphoma; hepatosplenic γδ T-cell lymphoma; subcutaneous panniculitis-like T-cell lymphoma; mycosis fungoides/Sezary syndrome; anaplastic large cell lymphoma, T/null cell; peripheral T-cell lymphoma; angioimmunoblastic T-cell lymphoma; chronic lymphocytic leukemia (CLL); acute lymphocytic leukemia (ALL); prolymphocytic leukemia; and hairy cell leukemia.

Other malignancies of interest include, without limitation, acute myeloid leukemia, head and neck cancers, brain cancer, breast cancer, ovarian cancer, cervical cancer, colorectal cancer, endometrial cancer, gallbladder cancer, gastric cancer, bladder cancer, prostate cancer, testicular cancer, liver cancer, lung cancer, kidney (renal cell) cancer, esophageal cancer, pancreatic cancer, thyroid cancer, bile duct cancer, pituitary tumor, wilms tumor, kaposi sarcoma, osteosarcoma, thymus cancer, skin cancer, heart cancer, oral and larynx cancer, neuroblastoma and non-hodgkin lymphoma.

Neurological inflammatory conditions are of interest, e.g. Alzheimer's Disease, Parkinson's Disease, Lou Gehrig's Disease, etc. and demyelinating diseases, such as multiple sclerosis, chronic inflammatory demyelinating polyneuropathy, etc. as well as inflammatory conditions such as rheumatoid arthritis. Systemic lupus erythematosus (SLE) is an autoimmune disease characterized by polyclonal B cell activation, which results in a variety of anti-protein and non-protein autoantibodies (see Kotzin et al. (1996) Cell 85:303-306). These autoantibodies form immune complexes that deposit in multiple organ systems, causing tissue damage. An autoimmune component may be ascribed to atherosclerosis, where candidate autoantigens include Hsp60, oxidized LDL, and 2-Glycoprotein I (2GPI).

A sample for use in the methods described herein may be one that is collected from an animal subject (eg, a mammal, such as a mouse or rat) with a disease model or a condition modeling a disease for one or more of the diseases mentioned herein. A sample for use in the methods described herein may be one that is collected from a subject with a malignancy or hyperproliferative condition, including lymphomas, leukemias, and plasmacytomas. A lymphoma is a solid neoplasm of lymphocyte origin, and is most often found in the lymphoid tissue. Thus, for example, a biopsy from a lymph node, e.g. a tonsil, containing such a lymphoma would constitute a suitable biopsy. Samples may be obtained from a subject at one or a plurality of time points in the progression of disease and/or treatment of the disease.

In some embodiments, the disclosure provides methods for performing target-specific multiplex PCR on a cDNA sample having a plurality of expressed immune receptor target sequences using primers having a cleavable group.

In certain embodiments, library and/or template preparation to be sequenced are prepared automatically from a population of nucleic acid samples using the compositions provided herein using an automated systems, e.g., the Ion ChefUM system.

As used herein, the term "subject" includes a human or other animal (usually a mammal, for example, mouse, rat or other rodent), a person, a patient, an individual, someone or an animal being evaluated, etc.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or.

As used herein, "antigen" refers to any substance that, when introduced into a body, e.g., of a subject, can stimulate an immune response, such as the production of an antibody or T cell receptor that recognizes the antigen. Antigens include molecules such as nucleic acids, lipids, ribonucleoprotein complexes, protein complexes, proteins, polypeptides, peptides and naturally occurring or synthetic modifications of such molecules against which an immune response involving T and/or B lymphocytes can be generated. With regard to autoimmune disease, the antigens herein are often referred to as autoantigens. With regard to allergic disease the antigens herein are often referred to as allergens. Autoantigens are any molecule produced by the organism that can be the target of an immunologic response, including peptides, polypeptides, and proteins encoded within the genome of the organism and post-translationally-generated modifications of these peptides, polypeptides, and proteins. Such molecules also include carbohydrates, lipids and other molecules produced by the organism. Antigens also include vaccine antigens, which include, without limitation, pathogen antigens, cancer associated antigens, allergens, and the like.

As used herein, "amplify", "amplifying" or "amplification reaction" and their derivatives, refer to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes PCR.

As used herein, "amplification conditions" and its derivatives, refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences includes PCR conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ (e.g., $MgCl_2$, etc) and can also include various modifiers of ionic strength.

As used herein, "target sequence" or "target sequence of interest" and its derivatives, refers to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises cDNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such as expressed RNA, fresh-frozen or formalin-fixed paraffin-embedded nucleic acid specimen.

As used herein, "contacting" and its derivatives, when used in reference to two or more components, refers to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. Where one or more of the referenced components to be contacted includes a plurality (e.g., "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms 'polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature ($T_m$), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPs and a polymerase. In some embodiments, the primer includes one or more cleavable groups at one or more locations within the primer.

As used herein, "target-specific primer" and its derivatives, refers to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or identical, across its entire length to at least a portion of a nucleic acid molecule that includes its corresponding target sequence. In some embodiments, a target-specific primer is at least 90%, at least 95% complementary, at least 98% complementary or at least 99% complementary, or identical, across its entire length to at least a portion of its corresponding target sequence. In some embodiments, a forward target-specific primer and a reverse target-specific primer define a target-specific primer pair that are used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification is performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer is substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3'end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

As used herein, "polymerase" and its derivatives, refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase is a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase is optionally reactivated, for example through the use of heat, chemicals or re-addition of new amounts of polymerase into a reaction mixture. In some embodiments, the polymerase can include a hot-start polymerase or an aptamer based polymerase that optionally is reactivated.

As used herein, the term "nucleotide" and its variants comprises any compound, including without limitation any naturally occurring nucleotide or analog thereof, which can bind selectively to, or is polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain is attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain is linked together with intervening O, NH, S, methylene, substituted methylene, ethylene, substituted ethylene, $CNH_2$, C(O), $C(CH_2)$, $CH_2CH_2$, or C(OH) $CH_2R$ (where R can be a 4-pyridine or 1-imidazole). In one embodiment, the phosphorus atoms in the chain has side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in U.S. Pat. No. 7,405,281. In some embodiments, the nucleotide comprises a label and referred to herein as a "labeled nucleotide"; the label of the labeled nucleotide is referred to herein as a "nucleotide label." In some embodiments, the label is in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. alpha-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the sequences where two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. In some embodiments, the amplified target sequences is less than 50% complementary to any portion of another amplified target sequence in the reaction. In other embodiments, the amplified target sequences is greater than 50%, greater than 60%, greater than 70%, greater than 80%, or greater than 90% complementary to any portion of another amplified target sequence in the reaction.

As used herein, the terms "ligating", "ligation" and their derivatives refer to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5'phosphate to a 3' hydroxyl between adjacent nucleotides can be employed. In an exemplary embodiment, an enzyme such as a ligase is used. For the purposes of this disclosure, an amplified target sequence can be ligated to an adapter to generate an adapter-ligated amplified target sequence.

As used herein, "ligase" and its derivatives, refers to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. In some embodiments, the ligase is an isothermal ligase. In some embodiments, the ligase is a thermostable ligase. Suitable ligases may include, but not limited to, T4 DNA ligase, T4 RNA ligase, and *E. coli* DNA ligase.

As used herein, "ligation conditions" and its derivatives, refers to conditions suitable for ligating two molecules to each other. In some embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap is ligated in the presence of an enzyme, such as ligase at an appropriate temperature and pH. In some embodiments, T4 DNA ligase can join a nick between nucleic acids at a temperature of about 70-72° C.

As used herein, "blunt-end ligation" and its derivatives, refers to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang". In some embodiments, the end of nucleic acid molecule does not include any single stranded portion, such that every nucleotide in one strand of the end is based paired with opposing nucleotides in the other strand of the same nucleic acid molecule. In some embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in US Pat. Publication No. 2010/0129874. In some embodiments, blunt-ended ligation includes a nick translation reaction to seal a nick created during the ligation process.

As used herein, the terms "adapter" or "adapter and its complements" and their derivatives, refers to any linear oligonucleotide which is ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some embodiments, the adapter can include one or more cleavable groups at one or more locations. In another embodiment, the adapter can include a sequence that is substantially identical, or substantially complementary, to at least a portion of a primer, for example a universal primer. The structure and properties of universal amplification primers are well known to those skilled in the art and can be implemented for utilization in conjunction with provided methods and compositions to adapt to specific analysis platforms (e.g., as described herein universal P1 and A primers have been described in the art and utilized for sequencing on Ion Torrent sequencing platforms). Similarly, additional and other universal adaptor/primer sequences described and known in the art (e.g., Illumina universal adaptor/primer sequences, PacBio universal adaptor/primer sequences, etc.) can be used in conjunction with the methods and compositions provided herein. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

In some embodiments, an adapter is ligated to a polynucleotide through a blunt-end ligation. In other embodiments, an adapter is ligated to a polynucleotide via nucleotide overhangs on the ends of the adapter and the polynucleotide. For overhang ligation, an adapter may have a nucleotide overhang added to the 3' and/or 5' ends of the respective strands if the polynucleotides to which the adapters are to be ligated (eg, amplicons) have a complementary overhang added to the 3' and/or 5' ends of the respective strands. For example, adenine nucleotides can be added to the 3' terminus of an end-repaired PCR product. Adapters having with an overhang formed by thymine nucleotides can then dock with the A-overhang of the amplicon and be ligated to the amplicon by a DNA ligase, such as T4 DNA ligase.

As used herein, “reamplifying” or “reamplification” and their derivatives refer to any process whereby at least a portion of an amplified nucleic acid molecule is further amplified via any suitable amplification process (referred to in some embodiments as a “secondary” amplification or “reamplification”, thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the reamplification can involve the use of different amplification conditions and/or different primers, including different target-specific primers than the primary amplification.

As defined herein, a “cleavable group” refers to any moiety that once incorporated into a nucleic acid can be cleaved under appropriate conditions. For example, a cleavable group can be incorporated into a target-specific primer, an amplified sequence, an adapter or a nucleic acid molecule of the sample. In an exemplary embodiment, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adapter or a nucleic acid molecule of the sample by any acceptable means. For example, a cleavable group can be removed from a target-specific primer, an amplified sequence, an adapter or a nucleic acid molecule of the sample by enzymatic, thermal, photo-oxidative or chemical treatment. In one embodiment, a cleavable group can include a nucleobase that is not naturally occurring. For example, an oligodeoxyribonucleotide can include one or more RNA nucleobases, such as uracil that can be removed by a uracil glycosylase. In some embodiments, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one embodiment, a cleavable group can include a moiety that can be removed from a primer after amplification (or synthesis) upon exposure to ultraviolet light (i.e., bromodeoxyuridine). In another embodiment, a cleavable group can include methylated cytosine. Typically, methylated cytosine can be cleaved from a primer for example, after induction of amplification (or synthesis), upon sodium bisulfite treatment. In some embodiments, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adapter or a nucleic acid molecule of the sample.

As used herein, “cleavage step” and its derivatives, refers to any process by which a cleavable group is cleaved or otherwise removed from a target-specific primer, an amplified sequence, an adapter or a nucleic acid molecule of the sample. In some embodiments, the cleavage step involves a chemical, thermal, photo-oxidative or digestive process.

As used herein, the term “hybridization” is consistent with its use in the art, and refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule. The phrase “hybridizing under stringent conditions” and its variants refers to conditions under which hybridization of a target-specific primer to a target sequence occurs in the presence of high hybridization temperature and low ionic strength. In one exemplary embodiment, stringent hybridization conditions include an aqueous environment containing about 30 mM magnesium sulfate, about 300 mM Tris-sulfate at pH 8.9, and about 90 mM ammonium sulfate at about 60-68° C., or equivalents thereof. As used herein, the phrase “standard hybridization conditions” and its variants refers to conditions under which hybridization of a primer to an oligonucleotide (i.e., a target sequence), occurs in the presence of low hybridization temperature and high ionic strength. In one exemplary embodiment, standard hybridization conditions include an aqueous environment containing about 100 mM magnesium sulfate, about 500 mM Tris-sulfate at pH 8.9, and about 200 mM ammonium sulfate at about 50-55° C., or equivalents thereof.

As used herein, "GC content" and its derivatives, refers to the cytosine and guanine content of a nucleic acid molecule. The GC content of a target-specific primer (or adapter) of the disclosure is 85% or lower. More typically, the GC content of a target-specific primer or adapter of the disclosure is between 15-85%.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and is referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. One or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some embodiments, the 3' end does not include any unlinked 3' hydroxyl group but can include any moiety capable of serving as a site for attachment of nucleotides via primer extension and/or nucleotide polymerization. In some embodiments, the term "3' end" for example when referring to a target-specific primer, can include the terminal 10 nucleotides, the terminal 5 nucleotides, the terminal 4, 3, 2 or fewer nucleotides at the 3'end. In some embodiments, the term "3' end" when referring to a target-specific primer can include nucleotides located at nucleotide positions 10 or fewer from the 3' terminus.

As used herein, "5' end", and its derivatives, refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. One or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a 3' hydroxyl group, or to the 3'end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5'end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, "DNA barcode" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode can be incorporated into the nucleotide sequence of an adapter.

As used herein, the phrases "two rounds of target-specific hybridization" or "two rounds of target-specific selection" and their derivatives refers to any process whereby the same target sequence is subjected to two consecutive rounds of hybridization-based target-specific selection, wherein a target sequence is hybridized to a target-specific sequence. Each round of hybridization based target-specific selection can include multiple target-specific hybridizations to at least some portion of a target-specific sequence. In one exemplary embodiment, a round of target-specific selection includes a first target-specific hybridization involving a first region of the target sequence and a second target-specific hybridization involving a second region of the target sequence. The first and second regions can be the same or different. In some embodiments, each round of hybridization-based target-specific selection can include use of two target specific oligonucleotides (e.g., a forward target-specific primer and a reverse target-specific primer), such that each round of selection includes two target-specific hybridizations.

As used herein, "comparable maximal minimum melting temperatures" and its derivatives, refers to the melting temperature ($T_m$) of each nucleic acid fragment for a single adapter or target-specific primer after cleavage of the cleavable groups. The hybridization temperature of each nucleic acid fragment generated by a single adapter or target-specific primer is compared to determine the maximal minimum temperature required preventing hybridization of any nucleic acid fragment from the target-specific primer or adapter to the target sequence. Once the maximal hybridization temperature is known, it is possible to manipulate the adapter or target-specific primer, for example by moving the location of the cleavable group along the length of the primer, to achieve a comparable maximal minimum melting temperature with respect to each nucleic acid fragment.

As used herein, "addition only" and its derivatives, refers to a series of steps in which reagents and components are added to a first or single reaction mixture. Typically, the series of steps excludes the removal of the reaction mixture from a first vessel to a second vessel in order to complete the series of steps. An addition only process excludes the manipulation of the reaction mixture outside the vessel containing the reaction mixture. Typically, an addition-only process is amenable to automation and high-throughput.

As used herein, "synthesizing" and its derivatives, refers to a reaction involving nucleotide polymerization by a polymerase, optionally in a template-dependent fashion. Polymerases synthesize an oligonucleotide via transfer of a nucleoside monophosphate from a nucleoside triphosphate (NTP), deoxynucleoside triphosphate (dNTP) or dideoxynucleoside triphosphate (ddNTP) to the 3' hydroxyl of an extending oligonucleotide chain. For the purposes of this disclosure, synthesizing includes to the serial extension of a hybridized adapter or a target-specific primer via transfer of a nucleoside monophosphate from a deoxynucleoside triphosphate.

As used herein, "polymerizing conditions" and its derivatives, refers to conditions suitable for nucleotide polymerization. In typical embodiments, such nucleotide polymerization is catalyzed by a polymerase. In some embodiments, polymerizing conditions include conditions for primer extension, optionally in a template-dependent manner, resulting in the generation of a synthesized nucleic acid sequence. In some embodiments, the polymerizing conditions include PCR. Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some embodiments, polymerizing conditions are practiced using thermocycling. Additionally, polymerizing conditions can include a plurality of cycles where the steps of annealing, extending, and separating the two nucleic strands are repeated. Typically, the polymerizing conditions include a cation such as $MgCl_2$. Polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids.

Polynucleotides have associated counter ions, such as $H^+$, $NH^{4+}$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U' denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As defined herein, the term "nick translation" and its variants comprise the translocation of one or more nicks or gaps within a nucleic acid strand to a new position along the nucleic acid strand. In some embodiments, a nick is formed when a double stranded adapter is ligated to a double stranded amplified target sequence. In one example, the primer can include at its 5' end, a phosphate group that can ligate to the double stranded amplified target sequence, leaving a nick between the adapter and the amplified target sequence in the complementary strand. In some embodiments, nick translation results in the movement of the nick to the 3' end of the nucleic acid strand. In some embodiments, moving the nick can include performing a nick translation reaction on the adapter-ligated amplified target sequence. In some embodiments, the nick translation reaction is a coupled 5' to 3' DNA polymerization/degradation reaction, or coupled to a 5' to 3' DNA polymerization/strand displacement reaction. In some embodiments, moving the nick can include performing a DNA strand extension reaction at the nick site. In some embodiments, moving the nick can include performing a single strand exonuclease reaction on the nick to form a single stranded portion of the adapter-ligated amplified target sequence and performing a DNA strand extension reaction on the single stranded portion of the adapter-ligated amplified target sequence to a new position. In some embodiments, a nick is formed in the nucleic acid strand opposite the site of ligation.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of expressed RNA or cDNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as "PCR". Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules are PCR amplified using a plurality of different primer pairs, in some cases, one or more primer pairs per target nucleic acid molecule of interest, thereby forming a multiplex PCR reaction. In some embodiments provided herein, multiplex PCR amplifications are performed using a plurality of different primer pairs, in typical cases, one primer pair per target nucleic acid molecule. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}P$-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from RNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers to the number of different target-specific sequences that are amplified during that single multiplex amplification. In some embodiments, the plexy is about 12-plex, 24-plex, 48-plex, 74-plex, 96-plex, 120-plex, 144-plex, 168-plex, 192-plex, 216-plex, 240-plex, 264-plex, 288-plex, 312-plex, 336-plex, 360-plex, 384-plex, or 398-plex. In some embodiments, highly multiplexed amplification reactions include reactions with a plexy of greater than 12-plex.

In some embodiments, the amplified target sequences are formed via PCR. Extension of target-specific primers can be accomplished using one or more DNA polymerases. In one embodiment, the polymerase is any Family A DNA polymerase (also known as pol I family) or any Family B DNA polymerase. In some embodiments, the DNA polymerase is a recombinant form capable of extending target-specific primers with superior accuracy and yield as compared to a non-recombinant DNA polymerase. For example, the polymerase can include a high-fidelity polymerase or thermostable polymerase. In some embodiments, conditions for extension of target-specific primers can include 'Hot Start' conditions, for example Hot Start polymerases, such as Amplitaq Gold® DNA polymerase (Applied Biosciences), Platinum® Taq DNA Polymerase High Fidelity (Invitrogen) or KOD Hot Start DNA polymerase (EMD Biosciences). A 'Hot Start' polymerase includes a thermostable polymerase and one or more antibodies that inhibit DNA polymerase and 3'-5' exonuclease activities at ambient temperature. In some instances, 'Hot Start' conditions can include an aptamer.

In some embodiments, the polymerase is an enzyme such as Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus* woesei), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*). In some embodiments, the DNA polymerase can include at least one polymerase such as Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Ihc), Platinum® Taq DNA Polymerase (Invitrogen), Hemo Klentaq™ (New England Biolabs), Platinum® Taq DNA Polymerase High Fidelity (Invitrogen), Platinum® Pfx (Invitrogen), Accuprime™ Pfx (Invitrogen), or Accuprime™ Taq DNA Polymerase High Fidelity (Invitrogen).

In some embodiments, the DNA polymerase is a thermostable DNA polymerase. In some embodiments, the mixture of dNTPs is applied concurrently, or sequentially, in a random or defined order. In some embodiments, the amount of DNA polymerase present in the multiplex reaction is significantly higher than the amount of DNA polymerase used in a corresponding single plex PCR reaction. As defined herein, the term "significantly higher" refers to an at least 3-fold greater concentration of DNA polymerase present in the multiplex PCR reaction as compared to a corresponding single plex PCR reaction.

In some embodiments, the amplification reaction does not include a circularization of amplification product, for example as disclosed by rolling circle amplification.

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, preparation of nucleic acid libraries, nucleic acid sequencing and analysis, and the like. Specific illustrations of suitable techniques can be used by reference to the examples provided herein. Other equivalent conventional procedures can also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

In certain embodiments, compositions of the invention comprise target immune receptor primer sets wherein the primers are directed to sequences of the same target immune receptor gene. Immune receptors are selected from T cell receptors and antibody receptors. In some embodiments a T cell receptor is a T cell receptor selected from the group consisting of TCR alpha, TCR beta, TCR gamma, and TCR delta. In some embodiments the immune receptor is an antibody receptor selected from the group consisting of heavy chain alpha, heavy chain delta, heavy chain epsilon, heavy chain gamma, heavy chain mu, light chain kappa, and light chain lambda.

In some embodiments, compositions of the invention comprise target immune receptor primer sets selected to have various parameters or criteria outlined herein. In some embodiments, compositions of the invention comprise a plurality of target-specific primers (e.g., V gene FR3-directed primers and J gene directed primers) of about 15 nucleotides to about 40 nucleotides in length and having at least two or more following criteria: a cleavable group located at a 3' end of substantially all of the plurality of primers, a cleavable group located near or about a central nucleotide of substantially all of the plurality of primers, substantially all of the plurality of primers at a 5' end including only non-cleavable nucleotides, minimal cross-hybridization to substantially all of the primers in the plurality of primers, minimal cross-hybridization to non-specific sequences present in a sample, minimal self-complementarity, and minimal nucleotide sequence overlap at a 3' end or a 5' end of substantially all of the primers in the plurality of primers. In some embodiments, the composition can include primers with any 3, 4, 5, 6 or 7 of the above criteria.

In some embodiments, composition comprise a plurality of target-specific primers of about 15 nucleotides to about 40 nucleotides in length having two or more of the following criteria: a cleavable group located near or about a central nucleotide of substantially all of the plurality of primers, substantially all of the plurality of primers at a 5' end including only non-cleavable nucleotides, substantially all of the plurality of primers having less than 20% of the nucleotides across the primer's entire length containing a cleavable group, at least one primer having a complementary nucleic acid sequence across its entire length to a target sequence present in a sample, minimal cross-hybridization to substantially all of the primers in the plurality of primers, minimal cross-hybridization to non-specific sequences present in a sample, and minimal nucleotide sequence overlap at a 3' end or a 5' end of substantially all of the primers in the plurality of primers. In some embodiments, the composition can include primers with any 3, 4, 5, 6 or 7 of the above criteria.

In some embodiments, target-specific primers (e.g., V gene FR3-directed primers and J gene directed primers) used in the compositions of the invention are selected or designed to satisfy any one or more of the following criteria: (1) includes two or more modified nucleotides within the primer sequence, at least one of which is included near or at the termini of the primer and at least one of which is included at, or about the center nucleotide position of the primer sequence; (2) length of about 15 to about 40 bases in length; (3) $T_m$ of from above 60° C. to about 70° C.; (4) low cross-reactivity with non-target sequences present in the sample; (5) at least the first four nucleotides (going from 3' to 5' direction) are non-complementary to any sequence within any other primer present in the composition; and (6) non-complementary to any consecutive stretch of at least 5 nucleotides within any other sequence targeted for amplification with the primers. In some embodiments, the target-specific primers used in the compositions are selected or designed to satisfy any 2, 3, 4, 5, or 6 of the above criteria. In some embodiments, the two or more modified nucleotides have cleavable groups. In some embodiments, each of the plurality of target-specific primers comprises two or more modified nucleotides selected from a cleavable group of methylguanine, 8-oxo-guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

In some embodiments compositions are provided for analysis of an immune repertoire in a sample, comprising at least one set of i) a plurality of V gene primers directed to a majority of different V gene of at least one immune receptor coding sequence comprising at least a portion of framework region 3 (FR3) within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such a set comprises primers directed to an immune receptor comprising a T cell receptor. In more particular embodiments such set comprises primers directed to amplification of TCR beta sequences. In other embodiments such set comprises primers directed to TCR alpha. In still other embodiments at least two sets of primers are encompassed in a composition wherein the sets are directed to TCR alpha and TCR beta. In particular embodiments the set of primers comprises primers directed to an immune receptor comprising a B cell receptor. In more particular embodiments such set comprises primers directed to amplification of IgH sequences. In other embodiments at least two sets of primers are encompassed in a composition wherein at least one set is directed to TCR beta amplification and at least one set is directed to IgH amplification.

In particular embodiments, compositions provided include target TCR (e.g., TRB) primer sets comprising V gene primers wherein the one or more of a plurality of V gene primers are directed to sequences over an FR3 region about 50 nucleotides in length. In other embodiments the one or more of a plurality of V gene primers are directed to sequences over an FR3 region about 70 nucleotides in length. In other particular embodiments the one or more of a plurality of V gene primers are directed to sequences over an FR3 region about 40 to about 60 nucleotides in length. In some embodiments of provided compositions, a target TCR primer set comprises V gene primers comprising about 25 to about 40 different FR3-directed primers. In certain embodiments a target TCR primer set comprises V gene primers comprising about 28 to about 38 different FR3-directed primers. In some embodiments a target TCR primer set comprises V gene primers comprising about 35 to about 60 different FR3-directed primers. In some embodiments, a target TCR primer set comprises V gene primers comprising about 29, 31, 33, 35, 37, or 40 different FR3-directed primers. In some embodiments the target TCR primer set comprises a plurality of J gene primers. In some embodiments a target TCR primer set comprises at least 10 J gene primers wherein each is directed to at least a portion of a J gene within target polynucleotides. In certain embodiments a target TCR primer set comprises at least 10 J gene primers wherein each is directed to at least a portion of the same 50 nucleotide region within a target J gene region. In some embodiments a target TCR primer set comprises at least 15 J gene primers wherein each is directed to at least a portion of a J gene within target polynucleotides. In some embodiments a target TCR primer set comprises about 12 to about 22 J gene primers wherein each is directed to at least a portion of a J gene within target polynucleotides. In some embodiments a target TCR primer set comprises about 15 to about 20 J gene primers wherein each is directed to at least a portion of the J gene portion within target polynucleotides. In some embodiments a target TCR primer set comprises about 13, 15, 17 or 19 different J gene primers.

In particular embodiments, compositions of the invention comprise at least one set of primers comprising V gene primers i) and J gene primers ii) selected from Tables 2 and 3, respectively. In certain embodiments compositions of the invention comprise at least one set of primers i) and ii) comprising primers selected from SEQ ID NOs: 1-33 and 67-83 or selected from SEQ ID NOs: 34-66 and 84-100. In other certain embodiments compositions of the invention comprise at least one set of primers i) and ii) comprising primers selected from SEQ ID NOs: 1-33 and 84-100 or selected from SEQ ID NOs: 34-66 and 67-83.

In some embodiments compositions of the invention comprise at least one set of primers i) and ii) comprising at least 25 primers selected from SEQ ID NOs: 1-33 and at least 11 primers, at least 13 primers, at least 15 primers, or at least 17 primers selected from SEQ ID NOs: 67-83. In some embodiments compositions of the invention comprise at least one set of primers i) and ii) comprising at least 25 primers selected from SEQ ID NOs: 34-66 and at least 11 primers, at least 13 primers, at least 15 primers, or at least 17 primers selected from SEQ ID NOs: 84-100. In some embodiments compositions of the invention comprise at least one set of primers i) and ii) comprising at least 25 primers selected from SEQ ID NOs: 1-33 and at least 11 primers, at least 13 primers, at least 15 primers, or at least 17 primers selected from SEQ ID NOs: 84-100. In some embodiments compositions of the invention comprise at least one set of primers i) and ii) comprising at least 25 primers selected from SEQ ID NOs: 34-66 and at least 11 primers, at least 13 primers, at least 15 primers, or at least 17 primers selected from SEQ ID NOs: 67-83.

In particular embodiments, compositions provided include target BCR (e.g., IgH) primer sets comprising V gene primers wherein the one or more of a plurality of V gene primers are directed to sequences over an FR3 region about 50 nucleotides in length. In other embodiments the one or more of a plurality of V gene primers are directed to sequences over an FR3 region about 70 nucleotides in length. In other particular embodiments the one or more of a plurality of V gene primers are directed to sequences over an FR3 region about 40 to about 60 nucleotides in length. In some embodiments of provided compositions, a target BCR primer set comprises V gene primers comprising about 70 to about 120 different FR3-directed primers. In certain embodiments a target TCR primer set comprises V gene primers comprising about 80 to about 105 different FR3-directed primers. In some embodiments a target BCR primer set comprises V gene primers comprising about 85 to about 95 different FR3-directed primers. In some embodiments, a target BCR primer set comprises V gene primers comprising about 85, 86, 87, 88, 89, 90, 91, 92, 93, 94 or 95 different FR3-directed primers. In some embodiments the target BCR primer set comprises a plurality of J gene primers. In some embodiments a target BCR primer set comprises at least one J gene primers wherein each is directed to at least a portion of a J gene within target polynucleotides. In certain embodiments a target BCR primer set comprises at least 2 to about 12 J gene primers wherein each is directed to at least a portion of the same 50 nucleotide region within a target J gene region. In some embodiments a target BCR primer set comprises about 4 to about 8 different J gene primers wherein each is directed to at least a portion of a J gene within target polynucleotides. In some embodiments a target BCR primer set comprises about 3, 4, 5, 6, 7, 8, or 9 different J gene primers wherein each is directed to at least a portion of a J gene within target polynucleotides. In particular embodiments a target BCR primer set comprises about 7 J gene primers wherein each is directed to at least a portion of the J gene portion within target polynucleotides.

In particular embodiments, compositions of the invention comprise at least one set of primers comprising V gene primers i) and J gene primers ii) selected from Tables 4 and 5, respectively. In certain embodiments compositions of the invention comprise at least one set of primers i) and ii) comprising primers selected from SEQ ID NOs: 101-541 and 983-1017 or selected from SEQ ID NOs: 542-982 and 1018-1052. In other certain embodiments compositions of the invention comprise at least one set of primers i) and ii) comprising primers selected from SEQ ID NOs: 101-541 and 1018-1052 or selected from SEQ ID NOs: 542-982 and 983-1017.

In some embodiments compositions of the invention comprise at least one set of primers i) and ii) comprising at least 85 primers selected from SEQ ID NOs: 101-541 and at least 3 primers, at least 5 primers, or at least 7 primers selected from SEQ ID NOs: 983-1017. In some embodiments compositions of the invention comprise at least one set of primers i) and ii) comprising at least 85 primers selected from SEQ ID NOs: 542-982 and at least 3 primers, at least 5 primers, or at least 7 primers selected from SEQ ID NOs: 1018-1052. In some embodiments compositions of the invention comprise at least one set of primers i) and ii) comprising at least 85 primers selected from SEQ ID NOs: 101-541 and at least 3 primers, at least 5 primers, or at least 7 primers selected from SEQ ID NOs: 1018-1052. In some embodiments compositions of the invention comprise at least one set of primers i) and ii) comprising at least 85 primers selected from SEQ ID NOs: 542-982 and at least 3 primers, at least 5 primers, at least 7 primers selected from SEQ ID NOs: 983-1017.

In some embodiments compositions of the invention comprise at least one set of primers i) and ii) comprising at least 85 primers selected from SEQ ID NOs: 101-281 and at least 3 primers, at least 5 primers, or at least 7 primers selected from SEQ ID NOs: 983-996. In some embodiments compositions of the invention comprise at least one set of primers i) and ii) comprising at least 85 primers selected from SEQ ID NOs: 193-367 and at least 3 primers, at least 5 primers, or at least 7 primers selected from SEQ ID NOs: 990-1003. In some embodiments compositions of the invention comprise at least one set of primers i) and ii) comprising at least 85 primers selected from SEQ ID NOs: 282-453 and at least 3 primers, at least 5 primers, or at least 7 primers selected from SEQ ID NOs: 997-1010. In some embodiments compositions of the invention comprise at least one set of primers i) and ii) comprising at least 85 primers selected from SEQ ID NOs: 368-541 and at least 3 primers, at least 5 primers, at least 7 primers selected from SEQ ID NOs: 1004-1017.

In some embodiments compositions of the invention comprise at least one set of primers i) and ii) comprising at least 85 primers selected from SEQ ID NOs: 542-722 and at least 3 primers, at least 5 primers, or at least 7 primers selected from SEQ ID NOs: 1018-1031. In some embodiments compositions of the invention comprise at least one set of primers i) and ii) comprising at least 85 primers selected from SEQ ID NOs: 634-808 and at least 3 primers, at least 5 primers, or at least 7 primers selected from SEQ ID NOs: 1025-1038. In some embodiments compositions of the invention comprise at least one set of primers i) and ii) comprising at least 85 primers selected from SEQ ID NOs: 723-894 and at least 3 primers, at least 5 primers, or at least 7 primers selected from SEQ ID NOs: 1032-1045. In some embodiments compositions of the invention comprise at least one set of primers i) and ii) comprising at least 85 primers selected from SEQ ID NOs: 809-982 and at least 3 primers, at least 5 primers, at least 7 primers selected from SEQ ID NOs: 1039-1052.

In some embodiments, multiple different primers including at least one modified nucleotide can be used in a single amplification reaction. For example, multiplexed primers including modified nucleotides can be added to the amplification reaction mixture, where each primer (or set of primers) selectively hybridizes to, and promotes amplification of different rearranged target nucleic acid molecules within the nucleic acid population. In some embodiments, the target specific primers can include at least one uracil nucleotide.

In some embodiments, multiplex amplification may be performed using PCR and cycles of denaturation, primer annealing, and polymerase extension steps at set temperatures for set times. In some embodiments, about 12 cycles to about 30 cycles are used to generate the amplicon library in the multiplex amplification reaction. In some embodiments, 13 cycles, 14 cycles, 15 cycles, 16 cycles, 17 cycles, 18 cycles, 19 cycles, preferably 20 cycles, 23 cycles, or 25 cycles are used to generate the amplicon library in the multiplex amplification reaction. In some embodiments, 17-25 cycles are used to generate the amplicon library in the multiplex amplification reaction.

In some embodiments, the amplification reactions are conducted in parallel within a single reaction phase (for example, within the same amplification reaction mixture within a single well or tube). In some instances, an amplification reaction can generate a mixture of products including both the intended amplicon product as well as unintended, unwanted, nonspecific amplification artifacts such as primer-dimers. Post amplification, the reactions are then treated with any suitable agent that will selectively cleave or otherwise selectively destroy the nucleotide linkages of the modified nucleotides within the excess unincorporated primers and the amplification artifacts without cleaving or destroying the specification amplification products. For example, the primers can include uracil-containing nucleobases that can be selectively cleaved using UNG/UDG (optionally with heat and/or alkali). In some embodiments, the primers can include uracil-containing nucleotides that can be selectively cleaved using UNG and Fpg. In some embodiments, the cleavage treatment includes exposure to oxidizing conditions for selective cleavage of dithiols, treatment with RNAse H for selective cleavage of modified nucleotides including RNA-specific moieties (e.g., ribose sugars, etc.), and the like. This cleavage treatment can effectively fragment the original amplification primers and non-specific amplification products into small nucleic acid fragments that include relatively few nucleotides each. Such fragments are typically incapable of promoting further amplification at elevated temperatures. Such fragments can also be removed relatively easily from the reaction pool through the various post-amplification cleanup procedures known in the art (e.g., spin columns, NaEtOH precipitation, etc).

In some embodiments, amplification products following cleavage or other selective destruction of the nucleotide linkages of the modified nucleotides are optionally treated to generate amplification products that possess a phosphate at the 5' termini. In some embodiments, the phosphorylation treatment includes enzymatic manipulation to produce 5' phosphorylated amplification products. In one embodiment, enzymes such as polymerases can be used to generate 5' phosphorylated amplification products. For example, T4 polymerase can be used to prepare 5' phosphorylated amplicon products. Klenow can be used in conjunction with one or more other enzymes to produce amplification products with a 5' phosphate. In some embodiments, other enzymes known in the art can be used to prepare amplification products with a 5' phosphate group. For example, incubation of uracil nucleotide containing amplification products with the enzyme UDG, Fpg and T4 polymerase can be used to generate amplification products with a phosphate at the 5' termini. It will be apparent to one of skill in the art that other techniques, other than those specifically described herein, can be applied to generate phosphorylated amplicons. It is understood that such variations and modifications that are applied to practice the methods, systems, kits, compositions and apparatuses disclosed herein, without resorting to undue experimentation are considered within the scope of the disclosure.

In some embodiments, primers that are incorporated in the intended (specific) amplification products, these primers are similarly cleaved or destroyed, resulting in the formation of "sticky ends" (e.g., 5' or 3' overhangs) within the specific amplification products. Such "sticky ends" can be addressed in several ways. For example, if the specific amplification products are to be cloned, the overhang regions can be designed to complement overhangs introduced into the cloning vector, thereby enabling sticky ended ligations that are more rapid and efficient than blunt ended ligations. Alternatively, the overhangs may need to be repaired (as with several next-generation sequencing methods). Such repair can be accomplished either through secondary amplification reactions using only forward and reverse amplification primers (e.g., correspond to A and P1 primers) comprised of only natural bases. In this manner, subsequent rounds of amplification rebuild the double-stranded templates, with nascent copies of the amplicon possessing the complete sequence of the original strands prior to primer destruction. Alternatively, the sticky ends can be removed using some forms of fill-in and ligation processing, wherein the forward and reverse primers are annealed to the templates. A polymerase can then be employed to extend the primers, and then a ligase, optionally a thermostable ligase, can be utilized to connect the resulting nucleic acid strands. This could obviously be also accomplished through various other reaction pathways, such as cyclical extend-ligation, etc. In some embodiments, the ligation step can be performed using one or more DNA ligases.

In some embodiments, the amplicon library prepared using target-specific primer pairs can be used in downstream enrichment applications such as emulsion PCR, bridge PCR or isothermal amplification. In some embodiments, the amplicon library can be used in an enrichment application and a sequencing application. For example, an amplicon library can be sequenced using any suitable DNA sequencing platform, including any suitable next generation DNA sequencing platform. In some embodiments, an amplicon library can be sequenced using an Ion Torrent PGM Sequencer or an Ion GeneStudio S5 Sequencer (Thermo Fisher Scientific). In some embodiments, a PGM Sequencer or S5 Sequencer can be coupled to server that applies parameters or software to determine the sequence of the amplified target nucleic acid molecules. In some embodiments, the amplicon library can be prepared, enriched and sequenced in less than 24 hours. In some embodiments, the amplicon library can be prepared, enriched and sequenced in approximately 9 hours.

In some embodiments, methods for generating an amplicon library can include: amplifying cDNA of immune receptor genes using V gene-specific and C gene-specific primers to generate amplicons; purifying the amplicons from the input DNA and primers; phosphorylating the amplicons; ligating adapters to the phosphorylated amplicons; purifying the ligated amplicons; nick-translating the amplified amplicons; and purifying the nick-translated amplicons to generate the amplicon library. In some embodiments, methods for generating an amplicon library can include: amplifying cDNA or rearranged gDNA of immune receptor genes using V gene-specific and J gene-specific primers to generate amplicons; purifying the amplicons from the input DNA and primers; phosphorylating the amplicons; ligating adapters to the phosphorylated amplicons; purifying the ligated amplicons; nick-translating the amplified amplicons; and purifying the nick-translated amplicons to generate the amplicon library. In some embodiments, additional amplicon library manipulations can be conducted following the step of amplification of rearranged immune receptor gene targets to generate the amplicons. In some embodiments, any combination of additional reactions can be conducted in any order, and can include: purifying; phosphorylating; ligating adapters; nick-translating; amplification and/or sequencing. In some embodiments, any of these reactions can be omitted or can be repeated. It will be readily apparent to one of skill in the art that the method can repeat or omit any one or more of the above steps. It will also be apparent to one of skill in the art that the order and combination of steps may be modified to generate the required amplicon library, and is not therefore limited to the exemplary methods provided.

A phosphorylated amplicon can be joined to an adapter to conduct a nick translation reaction, subsequent downstream amplification (e.g., template preparation), or for attachment to particles (e.g., beads), or both. For example, an adapter that is joined to a phosphorylated amplicon can anneal to an oligonucleotide capture primer which is attached to a particle, and a primer extension reaction can be conducted to generate a complimentary copy of the amplicon attached to the particle or surface, thereby attaching an amplicon to a surface or particle. Adapters can have one or more amplification primer hybridization sites, sequencing primer hybridization sites, barcode sequences, and combinations thereof. In some embodiments, amplicons prepared by the methods disclosed herein can be joined to one or more Ion Torrent™ compatible adapters to construct an amplicon library. Amplicons generated by such methods can be joined to one or more adapters for library construction to be compatible with a next generation sequencing platform. For example, the amplicons produced by the teachings of the present disclosure can be attached to adapters provided in the Ion AmpliSeq™ Library Kit 2.0 or Ion AmpliSeq™ Library Kit Plus (Thermo Fisher Scientific).

In some embodiments, amplification of immune receptor cDNA or rearranged gDNA can be conducted using a 5× Ion AmpliSeq™ HiFi Master Mix. In some embodiments, the 5× Ion AmpliSeq™ HiFi Master Mix can include glycerol, dNTPs, and a DNA polymerase such as Platinum™ Taq DNA polymerase High Fidelity. In some embodiments, the 5× Ion AmpliSeq™ HiFi Master Mix can further include at least one of the following: a preservative, magnesium chloride, magnesium sulfate, tris-sulfate and/or ammonium sulfate.

In some embodiments, the immune receptor rearranged gDNA multiplex amplification reaction further includes at least one PCR additive to improve on-target amplification, amplification yield, and/or the percentage of productive sequencing reads. In some embodiments, the at least one PCR additive includes at least one of potassium chloride or additional dNTPs (e.g., dATP, dCTP, dGTP, dTTP). In some embodiments, the dNTPs as a PCR additive is an equimolar mixture of dNTPs. In some embodiments, the dNTP mix as a PCR additive is an equimolar mixture of dATP, dCTP, dGTP, and dTTP In some embodiments, about 0.2 mM to about 5.0 mM dNTPs is added to the multiplex amplification reaction. In some embodiments, amplification of rearranged immune receptor gDNA can be conducted using a 5× Ion AmpliSeq™ HiFi Master Mix and an additional about 0.2 mM to about 5.0 mM dNTPs in the reaction mixture. In some embodiments, amplification of rearranged immune receptor gDNA can be conducted using a 5× Ion AmpliSeq™ HiFi Master Mix and an additional about 0.5 mM to about 4 mM, about 0.5 mM to about 3 mM, about 0.5 mM to about 2.5 mM, about 0.5 mM to about 1.0 mM, about 0.75 mM to about 1.25 mM, about 1.0 mM to about 1.5 mM, about 1.0 to about 2.0 mM, about 2.0 mM to about 3.0 mM, about 1.25 to about 1.75 mM, about 1.3 to about 1.8 mM, about 1.4 mM to about 1.7 mM, or about 1.5 to about 2.0 mM dNTPs in the reaction mixture. In some embodiments, amplification of rearranged immune receptor gDNA can be conducted using a 5× Ion AmpliSeq™ HiFi Master Mix and an additional about 0.2 mM, about 0.4 mM, about 0.6 mM, about 0.8 mM, about 1.0 mM, about 1.2 mM, about 1.4 mM, about 1.6 mM, about 1.8 mM, about 2.0 mM, about 2.2 mM, about 2.4 mM, about 2.6 mM, about 2.8 mM, about 3.0 mM, about 3.5 mM, or about 4.0 mM dNTPs in the reaction mixture. In some embodiments, about 10 mM to about 200 mM potassium chloride is added to the multiplex amplification reaction. In some embodiments, amplification of rearranged immune receptor gDNA can be conducted using a 5× Ion AmpliSeq™ HiFi Master Mix and an additional about 10 mM to about 200 mM potassium chloride in the reaction mixture. In some embodiments, amplification of rearranged immune receptor gDNA can be conducted using a 5× Ion AmpliSeq™ HiFi Master Mix and an additional about 10 mM to about 60 mM, about 20 mM to about 70 mM, about 30 mM to about 80 mM, about 40 mM to about 90 mM, about 50 mM to about 100 mM, about 60 mM to about 120 mM, about 80 mM to about 140 mM, about 50 mM to about 150 mM, about 150 mM to about 200 mM or about 100 mM to about 200 mM potassium chloride in the reaction mixture. In some embodiments, amplification of rearranged immune receptor gDNA can be conducted using a 5× Ion AmpliSeq™ HiFi Master Mix and an additional about 10 mM, about 20 mM, about 30 mM, about 40 mM, about 50 mM, about 60 mM, about 70 mM, about 80 mM, about 90 mM, about 100 mM, about 120 mM, about 140 mM, about 150 mM, about 160 mM, about 180 mM, or about 200 mM potassium chloride in the reaction mixture.

In some embodiments, phosphorylation of the amplicons can be conducted using a FuPa reagent. In some embodiments, the FuPa reagent can include a DNA polymerase, a DNA ligase, at least one uracil cleaving or modifying enzyme, and/or a storage buffer. In some embodiments, the FuPa reagent can further include at least one of the following: a preservative and/or a detergent.

In some embodiments, phosphorylation of the amplicons can be conducted using a FuPa reagent. In some embodiments, the FuPa reagent can include a DNA polymerase, at least one uracil cleaving or modifying enzyme, an antibody and/or a storage buffer. In some embodiments, the FuPa reagent can further include at least one of the following: a preservative and/or a detergent. In some embodiments, the antibody is provided to inhibit the DNA polymerase and 3'-5' exonuclease activities at ambient temperature.

In some embodiments, the amplicon library produced by the teachings of the present disclosure are sufficient in yield to be used in a variety of downstream applications including the Ion Chef™ instrument and the Ion S5™ Sequencing Systems (Thermo Fisher Scientific).

It will be apparent to one of ordinary skill in the art that numerous other techniques, platforms or methods for clonal amplification such as wildfire PCR and bridge amplification can be used in conjunction with the amplified target sequences of the present disclosure. It is also envisaged that one of ordinary skill in art upon further refinement or optimization of the conditions provided herein can proceed directly to nucleic acid sequencing (for example using Ion PGM™ System or Ion S5™ System or Ion Proton™ System sequencers, Thermo Fisher Scientific) without performing a clonal amplification step.

In some embodiments, at least one of the amplified targets sequences to be clonally amplified can be attached to a support or particle. The support can be comprised of any suitable material and have any suitable shape, including, for example, planar, spheroid or particulate. In some embodiments, the support is a scaffolded polymer particle as described in U.S. Published App. No. 20100304982, hereby incorporated by reference in its entirety.

In some embodiments, a kit is provided for amplifying multiple immune receptor expression sequences or rearranged gDNA sequences from a population of nucleic acid molecules in a single reaction. In some embodiments, the kit includes a plurality of target-specific primer pairs containing one or more cleavable groups, one or more DNA polymerases, a mixture of dNTPs and at least one cleaving reagent. In one embodiment, the cleavable group is 8-oxo-deoxyguanosine, deoxyuridine or bromodeoxyuridine. In some embodiments, the at least one cleaving reagent includes RNaseH, uracil DNA glycosylase, Fpg or alkali. In one embodiment, the cleaving reagent is uracil DNA glycosylase. In some embodiments, the kit is provided to perform multiplex PCR in a single reaction chamber or vessel. In some embodiments, the kit includes at least one DNA polymerase, which is a thermostable DNA polymerase. In some embodiments, the concentration of the one or more DNA polymerases is present in a 3-fold excess as compared to a single PCR reaction. In some embodiments, the final concentration of each target-specific primer pair is present at about 5 nM to about 2000 nM. In some embodiments, the final concentration of each target-specific primer pair is present at about 25 nM to about 50 nM or about 100 nM to about 800 nM. In some embodiments, the final concentration of each target-specific primer pair is present at about 50 nM to about 400 nM or about 50 nM to about 200 nM. In some embodiments, the final concentration of each target-specific primer pair is present at about 200 nM or about 400 nM. In some embodiments, the kit provides amplification of immune repertoire expression sequences or rearranged gDNA sequences from TCR beta, TCR alpha, TCR gamma, TCR delta, immunoglobulin heavy chain gamma, immunoglobulin heavy chain mu, immunoglobulin heavy chain alpha, immunoglobulin heavy chain delta, immunoglobulin heavy chain epsilon, immunoglobulin light chain lambda, or immunoglobulin light chain kappa from a population of nucleic acid molecules in a single reaction chamber. In particular embodiments, a provided kit is a test kit. In some embodiments, the kit further comprises one or more adapters, barcodes, and/or antibodies.

TABLE 2

| TRB V gene FR3 | |
|---|---|
| Sequence | SEQ ID NO. |
| CCTTTTCATCTATGACAGTTTTAAATGCAT | 1 |
| GAACCCAACATCCTAAAGTGGGGCCAGCAGATC | 2 |
| AGAGCTTTCCCCTGACATTAGAGTCAACCAGTT | 3 |
| CTCATTTGAATCTTCGAATCAAGTCTGTAGAGC | 4 |
| CTTCTCCCTCATTCTGGAGTTGGCTA | 5 |
| CTCTGAAATGAACATGAGTGCCTTGG | 6 |
| TTTCTCTCTCATTCTGGAGTTGGCTT | 7 |
| GTGCATCCTGGAAATCCTATCCTCTG | 8 |
| CTGCAGCTTGGAAATCAGTTCCTCTG | 9 |
| GCTACTTTTACATGTATCTGCCGTGG | 10 |
| CTGCATCCTGGAAATCCTATCCTCUG | 11 |
| CTCCACTCTGAAGATTCAACCTACAG | 12 |
| CTCAACTCTGAAGATCCAGAGCACGC | 13 |
| CTTCACCTTCACTGTGGAATTGGCCT | 14 |
| TTTCTCCCTGATTCTGGATTCTGCTA | 15 |
| CTTCATCTTGGAAATGCAGTCCTCAG | 16 |
| CTCTGAGATTAACCTGAGTGCCTTGG | 17 |
| TTGCAGCCTAGAAATTCAGTCCTCTG | 18 |
| GCTACTTTTACATATATCTGCCGTGG | 19 |
| CTGCTCTCTCTACATTGGCTCTGCAG | 20 |
| CTTCTTCCTCCTGCTGGAATTGGCTT | 21 |
| CTCCACTCTCAAGATCCAGTCTGCAA | 22 |
| ATTCTCCCTCATTCTGGAGTTGGCTA | 23 |
| CTCAACGTTGACAGTGAACAATGCAA | 24 |
| TTTAGACCTTCAGATCACAGCTCTAA | 25 |
| ATGTACCATAGAGATCCAGTCCAGCA | 26 |
| CTCTGAGATGAACATGAGTGCCTTGG | 27 |
| TTTCACTCTGAAAATCCAACCCACAG | 28 |
| ATTCATCCTAAGCACGGAGAAGCTGC | 29 |
| CTCCATGTTGAAGAGCCAATCAACAC | 30 |

TABLE 2-continued

| TRB V gene FR3 | |
|---|---|
| Sequence | SEQ ID NO. |
| ACTGTGACATCTGCCCAGAAG | 31 |
| CTGCAAGTGGCCAACATGAGC | 32 |
| GGAATCAGAACGTGCGAAGCA | 33 |
| CCTTTTCATCTAUGACAGTTTTAAATGCAU | 34 |
| GAACCCAACAUCCTAAAGUGGGGCCAGCAGAUC | 35 |
| AGAGCTTUCCCCTGACAUTAGAGTCAACCAGTU | 36 |
| CTCATTTGAATCTUCGAATCAAGTCTGUAGAGC | 37 |
| CTTCTCCCTCATUCTGGAGTTGGCUA | 38 |
| CTCTGAAATGAACAUGAGTGCCTUGG | 39 |
| TTTCTCTCTCATUCTGGAGTTGGCTU | 40 |
| GTGCATCCTGGAAAUCCTATCCTCUG | 41 |
| CTGCAGCTTGGAAAUCAGTTCCTCUG | 42 |
| GCTACTTTTACAUGTATCTGCCGUGG | 43 |
| CTGCATCCTGGAAAUCCTATCCTCUG | 44 |
| CTCCACTCUGAAGATTCAACCUACAG | 45 |
| CUCAACTCTGAAGAUCCAGAGCACGC | 46 |
| CTTCACCTTCACUGTGGAATTGGCCU | 47 |
| TTTCTCCCTGATUCTGGATTCTGCUA | 48 |
| CTTCATCTTGGAAAUGCAGTCCUCAG | 49 |
| CTCTGAGATUAACCTGAGTGCCTUGG | 50 |
| TTGCAGCCTAGAAAUTCAGTCCTCUG | 51 |
| GCTACTTTTACAUATATCTGCCGUGG | 52 |
| CTGCTCTCTCUACATTGGCTCUGCAG | 53 |
| CTTCTTCCTCCUGCTGGAATTGGCTU | 54 |
| CTCCACTCUCAAGATCCAGTCUGCAA | 55 |
| ATTCTCCCTCATUCTGGAGTTGGCUA | 56 |
| CTCAACGTUGACAGTGAACAAUGCAA | 57 |
| TTTAGACCTTCAGAUCACAGCTCUAA | 58 |
| ATGTACCAUAGAGATCCAGUCCAGCA | 59 |
| CTCTGAGATGAACAUGAGTGCCTUGG | 60 |
| UTTCACTCTGAAAAUCCAACCCACAG | 61 |
| ATTCATCCUAAGCACGGAGAAGCUGC | 62 |
| CTCCATGTUGAAGAGCCAAUCAACAC | 63 |
| ACUGTGACATCUGCCCAGAAG | 64 |
| CTGCAAGUGGCCAACAUGAGC | 65 |
| GGAAUCAGAACGUGCGAAGCA | 66 |

TABLE 3

| TRB J gene | |
|---|---|
| Sequence | SEQ ID NO. |
| CTTATACCTAAGTTCCTTTCCAAGACC | 67 |
| CGAGGAGCCGAGTGCCTG | 68 |
| CAGTGAGCCGGGTGCCTG | 69 |
| TACAACTGTGAGTGTGGTTCCT | 70 |
| CTACAACTGTGAGTCTGGTTCCT | 71 |
| CTAGGACGGTGAGTCGTGTCCC | 72 |
| CCAAGACAGACAGCTTGGTTCC | 73 |
| CTACAACAATGAGCCGGCTTCC | 74 |
| CTATTACCAAAAGCCTGGTCCC | 75 |
| CTAAAACCGTGAGCCTGGTGCC | 76 |
| CCAGCACTGTCAGCTTTGAGCC | 77 |
| ATAGGCTGTTCAATCGGCTGCC | 78 |
| CGAGAACAGTCAGTCTGGTTCC | 79 |
| TAAAACCGTGAGCCTAGTGCC | 80 |
| CTAGCACCGATAGTCGGGTGCC | 81 |
| CCAGGACAGACAGCTTGGTTCC | 82 |
| CTAGAACAGAGAGTCGAGTCCC | 83 |
| CTTATACCUAAGTTCCTTUCCAAGACC | 84 |
| CGAGGAGCCGAGUGCCUG | 85 |
| CAGTGAGCCGGGUGCCUG | 86 |
| TACAACTGTGAGUGTGGTTCCU | 87 |
| CTACAACTGUGAGTCTGGTTCCU | 88 |
| CTAGGACGGUGAGTCGTGUCCC | 89 |
| CCAAGACAGACAGCUTGGTUCC | 90 |
| CTACAACAAUGAGCCGGCTUCC | 91 |
| CTATUACCAAAAGCCTGGUCCC | 92 |
| CTAAAACCGUGAGCCTGGUGCC | 93 |
| CCAGCACUGTCAGCTTUGAGCC | 94 |
| ATAGGCTGTUCAATCGGCUGCC | 95 |
| CGAGAACAGUCAGTCTGGTUCC | 96 |
| TAAAACCGUGAGCCTAGUGCC | 97 |
| CTAGCACCGAUAGTCGGGUGCC | 98 |
| CCAGGACAGACAGCUTGGTUCC | 99 |
| CTAGAACAGAGAGUCGAGUCCC | 100 |

TABLE 4

| IgH V gene FR3 | |
|---|---|
| Sequence | SEQ ID NO. |
| GCAGCTCAGAAGCCTGACAT | 101 |
| GGAGCTCAGCAGCCTGACAT | 102 |
| GCAGCTCAGCAGCCTGACTT | 103 |
| GGAGCTCCGCAGCCTGACAT | 104 |
| GCAACTCAGCAGCCTGACAA | 105 |
| GCAGCTCAGCAGCCTGACCT | 106 |
| GCAACTCAGCAGCCCGACAT | 107 |
| GGAGCTCCACAGCCTGACAT | 108 |
| GCAGTTCAACAGCCTGACAT | 109 |
| TCAGCTCAGCAGCCTGGCAT | 110 |
| GGAGCTTAGTAGATTGACAT | 111 |
| GCAGCTCAGCAGCCTGACAT | 112 |
| GTTGCTCAGCAGCCTGACCT | 113 |
| GGATCTCAGCAGCCTGACCT | 114 |
| GGAGCTCCGGAGCCTGGCAT | 115 |
| GGATCTCAGCAGCCCGACAT | 116 |
| GGAGCTCAACAGTCTGACAT | 117 |
| GCAGCTCAAGAGCCTGACAT | 118 |
| GGAGCTCAGCCGATTAACAT | 119 |
| GCAACTCAGCAGCCTGACAT | 120 |
| GGAACTTGCCAGATTGACAT | 121 |
| GGAGCTCAGCAGCCTGACAA | 122 |
| GGACGTCCGCAGCCTGACAT | 123 |
| GGAGCTCCTGAGCCTGACAT | 124 |
| GCACCTCAGCAGCCTGACAT | 125 |
| GGAGCTCAACAGCCTGACAT | 126 |
| GCAACTGAGCAGCCTGACAT | 127 |
| GGAGCTAAACAGCCTGACTT | 128 |
| GGAACTCAGCAGCCTCACAT | 129 |
| GCAACTCAGCAGCTTGACAT | 130 |
| GGATCTCAGCAGCCTGACAT | 131 |
| GGAGCTCAGCAGCCTGACCT | 132 |
| GCAGTTCAGCAGCCTGACAT | 133 |
| GCAGCTCAACAGCCTGACAT | 134 |
| GCATCTCAACAGCCTGACAT | 135 |
| GCAGTCCAGCAGCCTGACAT | 136 |
| GCAGCTGAGCAGCCTGACAT | 137 |
| GCAGCTCAGCAGCCTAACAT | 138 |

TABLE 4-continued

| IgH V gene FR3 | |
|---|---|
| Sequence | SEQ ID NO. |
| GGAGCTCCGGAGCCTGACAT | 139 |
| GGTGTTGAACAGCCTGACAT | 140 |
| TGTACCTGCAAATGAGCAGTCTGAGTT | 141 |
| TGTACCTGGAAATGAGCAGTCTGAGGT | 142 |
| TGTACCTGCAAATGAGCCATCTGAAGT | 143 |
| TATACCTGCAAATGAGCAGTCTGAAGT | 144 |
| TTTACCTGCAAATGACCAGTCTGAAGT | 145 |
| TGTACCTGCAAATGAGCCGTCTGAAGT | 146 |
| TGTACCTGCAAATGAGCAGTCTGAAGT | 147 |
| TGTTCCTGCAAATGACCAGTCTAAGGT | 148 |
| TGTACCTGCAAATGAGCAGTCTGAGGT | 149 |
| TGTTCCTGCAAATGACCAGTCTGAGGT | 150 |
| CTTAAAAATGAACAGTCTCCAAA | 151 |
| CTTAAAACTGAACAGTCTGCAAA | 152 |
| CTTAAAAATGAACAGTCTGCAAA | 153 |
| CTTTAAAATGAACAGTCTGCAAG | 154 |
| CTTTAAAATGAACAGTCTGCAAT | 155 |
| ATGCTCTATCTGCAAATGAACAACCTGAAAA | 156 |
| ATGCTCTATCTGCAAATGAACAACTTGAAAA | 157 |
| GTCTACCTGCAAATGAACAACTTAAGGG | 158 |
| GTCTACCTGCAGATGGACAGATTAAGAG | 159 |
| GTCTACCTGCAAAAGAACAGCTTAAGAG | 160 |
| GTCTACCTGCAAATGAACAGCTTAAGAG | 161 |
| GTCTACCTGCATATGAACAGCTTAAGAG | 162 |
| GTATACCTGCAAATGAACAACTTAAGAG | 163 |
| GTCTACCTGCAAATGAACAACTTAAGAG | 164 |
| GTCTACCTAGAGATGAACAGATTAAGAG | 165 |
| GTCTACCTGCAGATGAACAGATTAAGAG | 166 |
| GCTGTACCTGCAAATGAGCAAAGTGAGAT | 167 |
| AGTTTTCTTTAAAATGAGCAGTCTGCAAA | 168 |
| CCTGTACCTGCAGATGAGCAATGTGCGAT | 169 |
| GTTCTTCCTCCAATTGAACTCTGTGACCA | 170 |
| GTTCTTTCTGCAATTGAACTCTGTGACCA | 171 |
| ATTCTTTATCCAGCTGAGCTCTGTGACAA | 172 |
| TTCCTGCAGTTGAATTCTGTGACTAC | 173 |
| TTCCTGAAGTTGAATTCTGTGACTAC | 174 |
| TTCCTGCAGTTGAACTCTGTGACTAT | 175 |
| TCACTGAAGTTGAGTTCTGTGACTAC | 176 |

TABLE 4-continued

IgH V gene FR3

| Sequence | SEQ ID NO. |
|---|---|
| TTCCTGCAGTTGAACTCTGTGACTAC | 177 |
| TTCCTGGAAATGAACTCTTTGACTGC | 178 |
| TTCTTGAAGTTGAATTCTGTGACTAC | 179 |
| TACCTGCAGTTGAATTCTGTGACTAC | 180 |
| TACCTACAGTTGAATTCTGTGACTAC | 181 |
| TACCTGCAGTTGAATTCTGTGACTTC | 182 |
| TCCTCTATCTTCAAATGAACACCCTGAGAG | 183 |
| TCCTCTACCTTCAGATGAATGCCCTGAGAG | 184 |
| TCCTCTATCTTCAAATGAACACCCTGAGGG | 185 |
| TCCTCTATCTTCAAATGAATGCCCTGAGAG | 186 |
| TTGCAGATCAACAACCTCAAAAA | 187 |
| TTACAGATAAGCAACCTCAAAAA | 188 |
| GGTATTCCTCAAGATCACCACTGTGGACA | 189 |
| GGTATTCCTCAAGATCGCCAGTGTGGACA | 190 |
| GGTATTCCTCAAGATCGCCAATGTGGACA | 191 |
| GGTATTCCTCAAGATCACCAGTGTGGACA | 192 |
| GCTCAAGAGCCTGACATCTGA | 193 |
| TCTCAACAGCCTGACATCTGA | 194 |
| GCTTAGTAGATTGACATCTGA | 195 |
| ACTTGCCAGATTGACATCTGA | 196 |
| GCTCAGCAGCCTGACAAATGA | 197 |
| GTTCAGCAGCCTGACATCTGA | 198 |
| GCTCAGCCGATTAACATCTGA | 199 |
| GCTCAACAGCCTGACATCTGA | 200 |
| GCTCAGCAGCCTGACATCTGA | 201 |
| ACTCAGCAGCCTCACATCTGA | 202 |
| TCTCAGCAGCCTGACCTCTGA | 203 |
| GCTCCGGAGCCTGACATCTGA | 204 |
| GCTCCGCAGCCTGACATCGGA | 205 |
| ACTGAGCAGCCTGACATCTGA | 206 |
| GCTCAGCAGCCTAACATCTGA | 207 |
| TCTCAGCAGCCTGACATCTGA | 208 |
| ACTCAGCAGCCCGACATCTGA | 209 |
| GCTCAGCAGCCTGACTTCTGA | 210 |
| GCTCCTGAGCCTGACATCTGA | 211 |
| ACTCAGCAGCTTGACATCTGA | 212 |
| GTCCAGCAGCCTGACATCTGA | 213 |
| GCTGAGCAGCCTGACATATGA | 214 |

TABLE 4-continued

IgH V gene FR3

| Sequence | SEQ ID NO. |
|---|---|
| GCTCCACAGCCTGACATCTGA | 215 |
| GCTCAACAGTCTGACATCCGA | 216 |
| CCTCAGCAGCCTGACATCTGA | 217 |
| GCTCCGCAGCCTGACATCTGA | 218 |
| TCTCAGCAGCCCGACATCTGA | 219 |
| GCTCAGCAGCCTGGCATCTGA | 220 |
| ACTCAGCAGCCTGACATCTGA | 221 |
| GCTCAGAAGCCTGACATCTGA | 222 |
| TCTCAGCAGCCTGACATCTAA | 223 |
| GCTCCGGAGCCTGGCATCTGA | 224 |
| GTTGAACAGCCTGACATCTGA | 225 |
| ACTCAGCAGCCTGACAACTGA | 226 |
| GCTAAACAGCCTGACTTCTGA | 227 |
| CGTCCGCAGCCTGACATCTGA | 228 |
| GCTCAACAGTCTGACATCTGA | 229 |
| GCTCAGCAGCCTGACCTCTGA | 230 |
| GTTCAACAGCCTGACATCTGA | 231 |
| AATGACCAGTCTGAGGTCTGAG | 232 |
| AATGAGCAGTCTGAAGTCTGAG | 233 |
| AATGACCAGTCTAAGGTCTGAG | 234 |
| AATGAGCCATCTGAAGTCTGAG | 235 |
| AATGAGCCGTCTGAAGTCTGAG | 236 |
| AATGAGCAGTCTGAGTTCTAAG | 237 |
| AATGAGCAGTCTGAGGTCTGAG | 238 |
| AATGACCAGTCTGAAGTCAGAG | 239 |
| TAAAAATGAACAGTCTCCAAACTGAT | 240 |
| TTAAAATGAACAGTCTGCAAGCTAAT | 241 |
| TTAAAATGAACAGTCTGCAATCTAAT | 242 |
| TTAAAATGAACAGTCTGCAAGCTGAT | 243 |
| TAAAACTGAACAGTCTGCAAACTGAT | 244 |
| TAAAAATGAACAGTCTGCAAACTGAT | 245 |
| TCTATCTGCAAATGAACAACTTGAAAACTGAG | 246 |
| TCTATCTGCAAATGAACAACCTGAAAACTGAG | 247 |
| CTGCAAATGAACAACTTAAGAGCTGAA | 248 |
| CTGCAAAAGAACAGCTTAAGAGCTGAA | 249 |
| CTGCAGATGAACAGATTAAGAGAGGAA | 250 |
| CTAGAGATGAACAGATTAAGAGAGGAA | 251 |
| CTGCAGATGGACAGATTAAGAGAGGAA | 252 |

TABLE 4-continued

IgH V gene FR3

| Sequence | SEQ ID NO. |
|---|---|
| CTGCAAATGAACAGCTTAAGAGCTGAA | 253 |
| CTGCAAATGAACAACTTAAGGGCTGAA | 254 |
| CTGCATATGAACAGCTTAAGAGCCGAA | 255 |
| CCTGCAGATGAGCAATGTGCGATCTGAG | 256 |
| CCTGCAGATGAGCAATGTGCGATCGGAG | 257 |
| TATCCAGCTGAGCTCTGTGACAAATGAG | 258 |
| CCTCCAATTGAACTCTGTGACCACAGAG | 259 |
| TCTGCAATTGAACTCTGTGACCACAGAG | 260 |
| CTTTAAAATGAGCAGTCTGCAAAGTGAA | 261 |
| CCTGCAAATGAGCAAAGTGAGATCTGAG | 262 |
| AGTTGAGTTCTGTGACTACTGAGG | 263 |
| AAATGAACTCTTTGACTGCTGAGG | 264 |
| AGTTGAATTCTGTGACTTCTGAGG | 265 |
| AAATGAACTCTTTGACTGCTGAAG | 266 |
| AGTTGAACTCTGTGACTACTGAAG | 267 |
| AGTTGAATTCTGTGACTACTGAGG | 268 |
| AGTTGAACTCTGTGACTATTGAAG | 269 |
| CTTCAAATGAACACCCTGAGGGCTGAG | 270 |
| CTTCAGATGAATGCCCTGAGAGCTGAG | 271 |
| CTTCAAATGAATGCCCTGAGAGCTGAG | 272 |
| CTTCAAATGAACACCCTGAGAGCTGAG | 273 |
| CAGATCAACAACCTCAAAAATCAG | 274 |
| CAGATAAGCAACCTCAAAAATGAG | 275 |
| CAGATCAACAACCTCAAAAATGAG | 276 |
| TATTCCTCAAGATCACCAGTGTGGACACTGCA | 277 |
| TATTCCTCAAGATCGCCAGTGTGGACACTGCA | 278 |
| TATTCCTCAAGATCGCCAATGTGGACACTGCA | 279 |
| TATTCCTCAAGATCACCACTGTGGACACTGCA | 280 |
| TATTCCTCAAGATCACCACTGTGGACACTGTA | 281 |
| CAGCAGCCTGACATCTGAGGAC | 282 |
| CAACAGTCTGACATCTGAGGAC | 283 |
| TGCCAGATTGACATCTGAGGAT | 284 |
| CAGCAGCCTGACATCTAAGGAC | 285 |
| CAGAAGCCTGACATCTGAG | 286 |
| CAACAGCCTGACATCTGAGGAT | 287 |
| CAGCAGCCTCACATCTGAGGAC | 288 |
| GAGCAGCCTGACATATGAGGAC | 289 |
| CAGCAGCTTGACATCTGAGGAC | 290 |

TABLE 4-continued

IgH V gene FR3

| Sequence | SEQ ID NO. |
|---|---|
| CAGCCGATTAACATCTGATGAC | 291 |
| CAGCAGCCTGACAAATGAGGAC | 292 |
| CAGCAGCCTGACAACTGAGGAC | 293 |
| TAGTAGATTGACATCTGAAGAC | 294 |
| CAGCAGCCCGACATCTGAGGAC | 295 |
| CAGCAGCCTGACATCTGAAGAC | 296 |
| AAACAGCCTGACTTCTGAGGAC | 297 |
| GAGCAGCCTGACATCTGAGGAC | 298 |
| CAGAAGCCTGACATCTGAGGAC | 299 |
| CCACAGCCTGACATCTGAGGAC | 300 |
| CCGCAGCCTGACATCTGAGGAC | 301 |
| CAGCAGCCTGACATCTGATGAC | 302 |
| CAAGAGCCTGACATCTGAGGAC | 303 |
| CAGCAGCCTGACCTCTGAGGAC | 304 |
| CCGGAGCCTGGCATCTGAGGAC | 305 |
| CAACAGCCTGACATCTGAGGAC | 306 |
| CAACAGCCTGACATCTGAAGAC | 307 |
| CCTGAGCCTGACATCTGAGGAC | 308 |
| CAGCAGCCTAACATCTGAGGAC | 309 |
| CAGCAGCCTGGCATCTGAGGAC | 310 |
| GAACAGCCTGACATCTGAGGAC | 311 |
| CAGCAGCCTGACTTCTGAGAAC | 312 |
| CAACAGTCTGACATCCGAGGAC | 313 |
| CCGGAGCCTGACATCTGAGGAC | 314 |
| CCGCAGCCTGACATCGGAGGAT | 315 |
| CAGCAGCCTGACATCTGACGAC | 316 |
| GACCAGTCTGAGGTCTGAGGAC | 317 |
| GAGCAGTCTGAGTTCTAAGGAC | 318 |
| GAGCCATCTGAAGTCTGAGGAC | 319 |
| GACCAGTCTAAGGTCTGAGGAC | 320 |
| GAGCAGTCTGAAGTCTGAGGAC | 321 |
| GAGCCGTCTGAAGTCTGAGGAC | 322 |
| GAGCAGTCTGAGGTCTGAGGAC | 323 |
| GACCAGTCTGAAGTCAGAGGAC | 324 |
| AAATGAACAGTCTGCAAGCTAATGAC | 325 |
| AAATGAACAGTCTCCAAACTGATGAC | 326 |
| AAATGAACAGTCTGCAAGCTGATGAC | 327 |
| AAATGAACAGTCTGCAAACTGATGAC | 328 |

TABLE 4-continued

| IgH V gene FR3 | |
|---|---|
| Sequence | SEQ ID NO. |
| AAATGAACAGTCTGCAATCTAATGAC | 329 |
| AACTGAACAGTCTGCAAACTGATGAC | 330 |
| CTGCAAATGAACAACTTGAAAACTGAGGAC | 331 |
| CTGCAAATGAACAACCTGAAAACTGAGGAC | 332 |
| CAAATGAACAGCTTAAGAGCTGAAGAC | 333 |
| CATATGAACAGCTTAAGAGCCGAAGAT | 334 |
| CAAAAGAACAGCTTAAGAGCTGAAGAT | 335 |
| CAAATGAACAACTTAAGAGCTGAAGAC | 336 |
| CAGATGAACAGATTAAGAGAGGAAGAC | 337 |
| GAGATGAACAGATTAAGAGAGGAAGAC | 338 |
| CAAATGAACAACTTAAGGGCTGAAGAC | 339 |
| CAGATGGACAGATTAAGAGAGGAAGAC | 340 |
| CCAGCTGAGCTCTGTGACAAATGAGGAC | 341 |
| GCAAATGAGCAAAGTGAGATCTGAGGAC | 342 |
| CCAATTGAACTCTGTGACCACAGAGGAC | 343 |
| TAAAATGAGCAGTCTGCAAAGTGAAGAC | 344 |
| GCAGATGAGCAATGTGCGATCGGAGGAC | 345 |
| GCAATTGAACTCTGTGACCACAGAGGAC | 346 |
| GCAGATGAGCAATGTGCGATCTGAGGAC | 347 |
| TTGAACTCTGTGACTACTGAAGA | 348 |
| ATGAACTCTTTGACTGCTGAGGA | 349 |
| TTGAATTCTGTGACTTCTGAGGA | 350 |
| TTGAGTTCTGTGACTACTGAGGA | 351 |
| TTGAACTCTGTGACTATTGAAGA | 352 |
| TTGAATTCTGTGACTACTGAGGA | 353 |
| ATGAACTCTTTGACTGCTGAAGA | 354 |
| CAGATGAATGCCCTGAGAGCTGAGGAC | 355 |
| CAAATGAACACCCTGAGAGCTGAGGAC | 356 |
| CAAATGAATGCCCTGAGAGCTGAGGAC | 357 |
| CAAATGAACACCCTGAGGGCTGAGGAC | 358 |
| CAAATGAACACCCTGAGAGCTGAGGCC | 359 |
| CAACAACCTCAAAAATCAGGAC | 360 |
| AAGCAACCTCAAAAATGAGGAC | 361 |
| CAACAACCTCAAAAATGAGGAC | 362 |
| AAGATCGCCAATGTGGACACTGCAGAT | 363 |
| AAGATCACCACTGTGGACACTGCAGAT | 364 |
| AAGATCACCAGTGTGGACACTGCAGAT | 365 |
| AAGATCGCCAGTGTGGACACTGCAGAT | 366 |

TABLE 4-continued

| IgH V gene FR3 | |
|---|---|
| Sequence | SEQ ID NO. |
| AAGATCACCACTGTGGACACTGTAGAT | 367 |
| AGCAGCCCGACATCTGAGGACT | 368 |
| AGCAGCCTGACATCTGATGACT | 369 |
| GCCAGATTGACATCTGAGGATT | 370 |
| CGGAGCCTGGCATCTGAGGACT | 371 |
| AACAGCCTGACTTCTGAGGACT | 372 |
| AGAAGCCTGACATCTGAGGACT | 373 |
| AACAGCCTGACATCTGAGGATT | 374 |
| AGCAGCCTGACATCTGAGGACA | 375 |
| AGAAGCCTGACATCTGAG | 376 |
| AACAGCCTGACATCTGAGGACC | 377 |
| AGCCGATTAACATCTGATGACT | 378 |
| AGCAGCCTGACTTCTGAGAACT | 379 |
| AGCAGCCTGACCTCTGAGGACT | 380 |
| CTGAGCCTGACATCTGAGGACT | 381 |
| AACAGCCTGACATCTGAGGACT | 382 |
| AACAGCCTGACATCTGAAGACT | 383 |
| AGCAGCCTGACATCTGAAGACT | 384 |
| AGCAGCTTGACATCTGAGGACT | 385 |
| AGCAGCCTGACATCTGAGGACT | 386 |
| AAGAGCCTGACATCTGAGGACT | 387 |
| AGCAGCCTGACAACTGAGGACT | 388 |
| CGCAGCCTGACATCTGAGGACT | 389 |
| AGCAGCCTGGCATCTGAGGACT | 390 |
| AGCAGCCTGACATCTAAGGACT | 391 |
| AGTAGATTGACATCTGAAGACT | 392 |
| CGGAGCCTGACATCTGAGGACT | 393 |
| AGCAGCCTGACATCTGACGACT | 394 |
| CACAGCCTGACATCTGAGGACT | 395 |
| AGCAGCCTAACATCTGAGGACT | 396 |
| AACAGTCTGACATCCGAGGACT | 397 |
| AACAGTCTGACATCTGAGGACT | 398 |
| AGCAGCCTGACAAATGAGGACT | 399 |
| AGCAGCCTGACATATGAGGACT | 400 |
| CGCAGCCTGACATCTGAGGACA | 401 |
| AGCAGCCTCACATCTGAGGACT | 402 |
| CGCAGCCTGACATCGGAGGATT | 403 |
| GAGCAGTCTGAGGTCTGAGGACA | 404 |

TABLE 4-continued

| IgH V gene FR3 | |
|---|---|
| Sequence | SEQ ID NO. |
| GACCAGTCTAAGGTCTGAGGACA | 405 |
| GAGCAGTCTGAGTTCTAAGGACA | 406 |
| GACCAGTCTGAGGTCTGAGGACA | 407 |
| GAGCCGTCTGAAGTCTGAGGACA | 408 |
| GACCAGTCTGAAGTCAGAGGACA | 409 |
| GAGCCATCTGAAGTCTGAGGACA | 410 |
| GAGCAGTCTGAAGTCTGAGGACA | 411 |
| AAATGAACAGTCTGCAATCTAATGACA | 412 |
| AACTGAACAGTCTGCAAACTGATGACA | 413 |
| AAATGAACAGTCTGCAAGCTAATGACA | 414 |
| AAATGAACAGTCTGCAAGCTGATGACA | 415 |
| AAATGAACAGTCTGCAAACTGATGACA | 416 |
| AAATGAACAGTCTCCAAACTGATGACA | 417 |
| CAAATGAACAACCTGAAAACTGAGGACA | 418 |
| CAAATGAACAACTTGAAAACTGAGGACA | 419 |
| ATGAACAACTTAAGAGCTGAAGACA | 420 |
| ATGAACAACTTAAGGGCTGAAGACA | 421 |
| ATGAACAGCTTAAGAGCTGAAGACA | 422 |
| ATGGACAGATTAAGAGAGGAAGACA | 423 |
| AAGAACAGCTTAAGAGCTGAAGATA | 424 |
| ATGAACAGATTAAGAGAGGAAGACA | 425 |
| ATGAACAGCTTAAGAGCCGAAGATA | 426 |
| CAAATGAGCAAAGTGAGATCTGAGGACA | 427 |
| CAGATGAGCAATGTGCGATCTGAGGACA | 428 |
| CAGATGAGCAATGTGCGATCTGAGGACC | 429 |
| CAATTGAACTCTGTGACCACAGAGGACA | 430 |
| CAGATGAGCAATGTGCGATCGGAGGACA | 431 |
| AAAATGAGCAGTCTGCAAAGTGAAGACA | 432 |
| CAGCTGAGCTCTGTGACAAATGAGGACA | 433 |
| GAACTCTGTGACTACTGAAGATA | 434 |
| GAATTCTGTGACTTCTGAGGACA | 435 |
| GAACTCTGTGACTATTGAAGATA | 436 |
| GAATTCTGTGACTACTGAGGACG | 437 |
| GAACTCTTTGACTGCTGAGGACA | 438 |
| GAATTCTGTGACTACTGAGGACA | 439 |
| GAACTCTTTGACTGCTGAAGACA | 440 |
| GAGTTCTGTGACTACTGAGGACA | 441 |
| TCAAATGAATGCCCTGAGAGCTGAGGACA | 442 |

TABLE 4-continued

| IgH V gene FR3 | |
|---|---|
| Sequence | SEQ ID NO. |
| TCAAATGAACACCCTGAGAGCTGAGGACA | 443 |
| TCAAATGAACACCCTGAGGGCTGAGGACA | 444 |
| TCAAATGAACACCCTGAGAGCTGAGGCCA | 445 |
| TCAGATGAATGCCCTGAGAGCTGAGGACA | 446 |
| AACCTCAAAAATGAGGACA | 447 |
| AACCTCAAAAATCAGGACA | 448 |
| AAGATCGCCAATGTGGACACTGCAGATA | 449 |
| AAGATCGCCAGTGTGGACACTGCAGATA | 450 |
| AAGATCACCACTGTGGACACTGCAGATA | 451 |
| AAGATCACCAGTGTGGACACTGCAGATA | 452 |
| AAGATCACCACTGTGGACACTGTAGATA | 453 |
| CGCAGCCTGACATCTGAGGACTC | 454 |
| CACAGCCTGACATCTGAGGACTC | 455 |
| AGCAGCCTCACATCTGAGGACTC | 456 |
| AGCAGCCTGACTTCTGAGAACTC | 457 |
| AGCAGCCTGACATATGAGGACTC | 458 |
| AACAGCCTGACTTCTGAGGACTC | 459 |
| AACAGCCTGACATCTGAGGACTT | 460 |
| AGCAGCCTGACATCTGACGACTC | 461 |
| AGCAGCCTGACATCTGAAGACTC | 462 |
| AGCAGCCTGACATCTGAGGACAC | 463 |
| AACAGCCTGACATCTGAAGACTC | 464 |
| AGCCGATTAACATCTGATGACTC | 465 |
| AACAGCCTGACATCTGAGGATTC | 466 |
| AGAAGCCTGACATCTGAG | 467 |
| AGCAGCCTGACAAATGAGGACTC | 468 |
| AACAGTCTGACATCTGAGGACTC | 469 |
| AGCAGCCTGACATCTGATGACTC | 470 |
| AGCAGCCTGGCATCTGAGGACTC | 471 |
| AGCAGCCCGACATCTGAGGACTC | 472 |
| AACAGCCTGACATCTGAGGACTC | 473 |
| AGCAGCTTGACATCTGAGGACTC | 474 |
| AGCAGCCTGACATCTAAGGACTC | 475 |
| CGGAGCCTGGCATCTGAGGACTC | 476 |
| AGCAGCCTGACAACTGAGGACTC | 477 |
| CGCAGCCTGACATCGGAGGATTC | 478 |
| AGAAGCCTGACATCTGAGGACTC | 479 |
| AGCAGCCTGACATCTGAGGACTC | 480 |

TABLE 4-continued

| IgH V gene FR3 | |
|---|---|
| Sequence | SEQ ID NO. |
| AGTAGATTGACATCTGAAGACTC | 481 |
| AACAGTCTGACATCCGAGGACTC | 482 |
| AGCAGCCTGACCTCTGAGGACTC | 483 |
| GCCAGATTGACATCTGAGGATTC | 484 |
| CGGAGCCTGACATCTGAGGACTC | 485 |
| AAGAGCCTGACATCTGAGGACTC | 486 |
| CTGAGCCTGACATCTGAGGACTT | 487 |
| AACAGCCTGACATCTGAGGACCC | 488 |
| CGCAGCCTGACATCTGAGGACAC | 489 |
| AGCAGCCTAACATCTGAGGACTC | 490 |
| AGCAGTCTGAAGTCTGAGGACAC | 491 |
| ACCAGTCTGAAGTCAGAGGACAC | 492 |
| AGCCATCTGAAGTCTGAGGACAC | 493 |
| ACCAGTCTGAGGTCTGAGGACAC | 494 |
| ACCAGTCTAAGGTCTGAGGACAC | 495 |
| AGCAGTCTGAGGTCTGAGGACAC | 496 |
| AGCAGTCTGAGTTCTAAGGACAC | 497 |
| AGCCGTCTGAAGTCTGAGGACAC | 498 |
| GAACAGTCTGCAAGCTAATGACAC | 499 |
| GAACAGTCTCCAAACTGATGACAC | 500 |
| GAACAGTCTGCAAACTGATGACAC | 501 |
| GAACAGTCTGCAATCTAATGACAC | 502 |
| GAACAGTCTGCAAGCTGATGACAC | 503 |
| TGAACAACTTGAAAACTGAGGACAC | 504 |
| TGAACAACCTGAAAACTGAGGACAC | 505 |
| ATATGAACAGCTTAAGAGCCGAAGATAC | 506 |
| AAATGAACAGCTTAAGAGCTGAAGACAC | 507 |
| AAAAGAACAGCTTAAGAGCTGAAGATAC | 508 |
| AGATGGACAGATTAAGAGAGGAAGACAC | 509 |
| AAATGAACAACTTAAGAGCTGAAGACAT | 510 |
| AGATGAACAGATTAAGAGAGGAAGACAC | 511 |
| AAATGAACAACTTAAGGGCTGAAGACAC | 512 |
| AAATGAACAACTTAAGAGCTGAAGACAC | 513 |
| AAATGAGCAAAGTGAGATCTGAGGACAC | 514 |
| AAATGAGCAGTCTGCAAAGTGAAGACAC | 515 |
| AATTGAACTCTGTGACCACAGAGGACAC | 516 |
| AGATGAGCAATGTGCGATCTGAGGACCC | 517 |
| AGATGAGCAATGTGCGATCGGAGGACAC | 518 |

TABLE 4-continued

| IgH V gene FR3 | |
|---|---|
| Sequence | SEQ ID NO. |
| AGATGAGCAATGTGCGATCTGAGGACAC | 519 |
| AGCTGAGCTCTGTGACAAATGAGGACAC | 520 |
| AACTCTGTGACTATTGAAGATAT | 521 |
| AACTCTGTGACTACTGAAGATAT | 522 |
| AATTCTGTGACTACTGAGGACGC | 523 |
| AACTCTTTGACTGCTGAGGACAC | 524 |
| AACTCTTTGACTGCTGAAGACAC | 525 |
| AATTCTGTGACTACTGAGGACAC | 526 |
| AGTTCTGTGACTACTGAGGACAC | 527 |
| AATTCTGTGACTTCTGAGGACAC | 528 |
| TCAAATGAATGCCCTGAGAGCTGAGGACA | 529 |
| TCAAATGAACACCCTGAGAGCTGAGGACA | 530 |
| TCAAATGAACACCCTGAGGGCTGAGGACA | 531 |
| TCAAATGAACACCCTGAGAGCTGAGGCCA | 532 |
| TCAGATGAATGCCCTGAGAGCTGAGGACA | 533 |
| CAACCTCAAAAATCAGGACAC | 534 |
| CAACCTCAAAAATGAGGACAC | 535 |
| CAACCTCAAAAATGAGGACAT | 536 |
| AGATCACCACTGTGGACACTGTAGATAC | 537 |
| AGATCGCCAATGTGGACACTGCAGATAC | 538 |
| AGATCACCAGTGTGGACACTGCAGATAC | 539 |
| AGATCGCCAGTGTGGACACTGCAGATAC | 540 |
| AGATCACCACTGTGGACACTGCAGATAC | 541 |
| GCAGCUCAGAAGCCUGACAT | 542 |
| GGAGCUCAGCAGCCUGACAT | 543 |
| GCAGCUCAGCAGCCTGACUT | 544 |
| GGAGCUCCGCAGCCUGACAT | 545 |
| GCAACUCAGCAGCCUGACAA | 546 |
| GCAGCUCAGCAGCCUGACCT | 547 |
| GCAACUCAGCAGCCCGACAT | 548 |
| GGAGCUCCACAGCCUGACAT | 549 |
| GCAGTUCAACAGCCUGACAT | 550 |
| TCAGCUCAGCAGCCUGGCAT | 551 |
| GGAGCUTAGTAGATUGACAT | 552 |
| GCAGCUCAGCAGCCUGACAT | 553 |
| GTTGCUCAGCAGCCUGACCT | 554 |
| GGATCUCAGCAGCCUGACCT | 555 |
| GGAGCUCCGGAGCCUGGCAT | 556 |

TABLE 4-continued

IgH V gene FR3

| Sequence | SEQ ID NO. |
|---|---|
| GGAUCUCAGCAGCCCGACAT | 557 |
| GGAGCUCAACAGTCUGACAT | 558 |
| GCAGCUCAAGAGCCUGACAT | 559 |
| GGAGCUCAGCCGATUAACAT | 560 |
| GCAACUCAGCAGCCUGACAT | 561 |
| GGAACTUGCCAGATUGACAT | 562 |
| GGAGCUCAGCAGCCUGACAA | 563 |
| GGACGUCCGCAGCCUGACAT | 564 |
| GGAGCUCCTGAGCCUGACAT | 565 |
| GCACCUCAGCAGCCUGACAT | 566 |
| GGAGCUCAACAGCCUGACAT | 567 |
| GCAACUGAGCAGCCUGACAT | 568 |
| GGAGCUAAACAGCCTGACUT | 569 |
| GGAACUCAGCAGCCUCACAT | 570 |
| GCAACUCAGCAGCTUGACAT | 571 |
| GGATCUCAGCAGCCUGACAT | 572 |
| GGAGCUCAGCAGCCUGACCT | 573 |
| GCAGTUCAGCAGCCUGACAT | 574 |
| GCAGCUCAACAGCCUGACAT | 575 |
| GCATCUCAACAGCCUGACAT | 576 |
| GCAGUCCAGCAGCCUGACAT | 577 |
| GCAGCUGAGCAGCCUGACAT | 578 |
| GCAGCUCAGCAGCCUAACAT | 579 |
| GGAGCUCCGGAGCCUGACAT | 580 |
| GGTGTUGAACAGCCUGACAT | 581 |
| TGTACCTGCAAAUGAGCAGTCTGAGUT | 582 |
| TGTACCTGGAAAUGAGCAGTCUGAGGT | 583 |
| TGTACCTGCAAAUGAGCCATCUGAAGT | 584 |
| TATACCTGCAAAUGAGCAGTCUGAAGT | 585 |
| TTTACCTGCAAAUGACCAGTCUGAAGT | 586 |
| TGTACCTGCAAAUGAGCCGTCUGAAGT | 587 |
| TGTACCTGCAAAUGAGCAGTCUGAAGT | 588 |
| TGTTCCTGCAAAUGACCAGTCUAAGGT | 589 |
| TGTACCTGCAAAUGAGCAGTCUGAGGT | 590 |
| TGTTCCTGCAAAUGACCAGTCUGAGGT | 591 |
| CTTAAAAAUGAACAGTCUCCAAA | 592 |
| CTTAAAACUGAACAGTCUGCAAA | 593 |
| CTTAAAAAUGAACAGTCUGCAAA | 594 |

TABLE 4-continued

IgH V gene FR3

| Sequence | SEQ ID NO. |
|---|---|
| CTTTAAAAUGAACAGTCUGCAAG | 595 |
| CTTTAAAAUGAACAGTCUGCAAT | 596 |
| ATGCTCTATCUGCAAATGAACAACCUGAAAA | 597 |
| ATGCTCTATCUGCAAATGAACAACTUGAAAA | 598 |
| GTCTACCUGCAAATGAACAACTUAAGGG | 599 |
| GTCTACCTGCAGAUGGACAGATUAAGAG | 600 |
| GTCTACCUGCAAAAGAACAGCTUAAGAG | 601 |
| GTCTACCTGCAAAUGAACAGCTUAAGAG | 602 |
| GTCTACCTGCAUATGAACAGCTUAAGAG | 603 |
| GTATACCTGCAAAUGAACAACTUAAGAG | 604 |
| GTCTACCUGCAAATGAACAACTUAAGAG | 605 |
| GTCTACCUAGAGATGAACAGATUAAGAG | 606 |
| GTCTACCUGCAGATGAACAGATUAAGAG | 607 |
| GCTGTACCUGCAAATGAGCAAAGUGAGAT | 608 |
| AGTTTTCTTTAAAAUGAGCAGTCUGCAAA | 609 |
| CCTGTACCUGCAGATGAGCAATGUGCGAT | 610 |
| GTTCTTCCTCCAAUTGAACTCTGUGACCA | 611 |
| GTTCTTTCTGCAAUTGAACTCTGUGACCA | 612 |
| ATTCTTTATCCAGCUGAGCTCTGUGACAA | 613 |
| TTCCTGCAGTUGAATTCTGTGACUAC | 614 |
| TTCCTGAAGTUGAATTCTGTGACUAC | 615 |
| TTCCTGCAGTUGAACTCTGTGACUAT | 616 |
| TCACTGAAGTUGAGTTCTGTGACUAC | 617 |
| TTCCTGCAGTUGAACTCTGTGACUAC | 618 |
| TTCCTGGAAAUGAACTCTTTGACUGC | 619 |
| TTCTTGAAGTUGAATTCTGTGACUAC | 620 |
| TACCTGCAGTUGAATTCTGTGACUAC | 621 |
| TACCTACAGTUGAATTCTGTGACUAC | 622 |
| TACCTGCAGTUGAATTCTGTGACTUC | 623 |
| TCCTCTATCTUCAAATGAACACCCUGAGAG | 624 |
| TCCTCTACCTUCAGATGAATGCCCUGAGAG | 625 |
| TCCTCTATCTUCAAATGAACACCCUGAGGG | 626 |
| TCCTCTATCTUCAAATGAATGCCCUGAGAG | 627 |
| TTGCAGAUCAACAACCUCAAAAA | 628 |
| TTACAGAUAAGCAACCUCAAAAA | 629 |
| GGTATTCCTCAAGAUCACCACTGUGGACA | 630 |
| GGTATTCCTCAAGAUCGCCAGTGUGGACA | 631 |
| GGTATTCCTCAAGAUCGCCAATGUGGACA | 632 |

TABLE 4-continued

| IgH V gene FR3 | |
|---|---|
| Sequence | SEQ ID NO. |
| GGTATTCCTCAAGAUCACCAGTGUGGACA | 633 |
| GCTCAAGAGCCUGACATCUGA | 634 |
| TCTCAACAGCCUGACATCUGA | 635 |
| GCTTAGTAGAUTGACATCUGA | 636 |
| ACTTGCCAGAUTGACATCUGA | 637 |
| GCTCAGCAGCCUGACAAAUGA | 638 |
| GTTCAGCAGCCUGACATCUGA | 639 |
| GCTCAGCCGAUTAACATCUGA | 640 |
| GCTCAACAGCCUGACATCUGA | 641 |
| GCTCAGCAGCCUGACATCUGA | 642 |
| ACTCAGCAGCCUCACATCUGA | 643 |
| TCTCAGCAGCCUGACCTCUGA | 644 |
| GCTCCGGAGCCUGACATCUGA | 645 |
| GCTCCGCAGCCUGACAUCGGA | 646 |
| ACTGAGCAGCCUGACATCUGA | 647 |
| GCTCAGCAGCCUAACATCUGA | 648 |
| TCTCAGCAGCCUGACATCUGA | 649 |
| ACUCAGCAGCCCGACATCUGA | 650 |
| GCTCAGCAGCCUGACTTCUGA | 651 |
| GCTCCUGAGCCTGACATCUGA | 652 |
| ACTCAGCAGCUTGACATCUGA | 653 |
| GTCCAGCAGCCUGACATCUGA | 654 |
| GCTGAGCAGCCUGACATAUGA | 655 |
| GCTCCACAGCCUGACATCUGA | 656 |
| GCTCAACAGUCTGACAUCCGA | 657 |
| CCTCAGCAGCCUGACATCUGA | 658 |
| GCTCCGCAGCCUGACATCUGA | 659 |
| TCUCAGCAGCCCGACATCUGA | 660 |
| GCTCAGCAGCCUGGCATCUGA | 661 |
| ACTCAGCAGCCUGACATCUGA | 662 |
| GCTCAGAAGCCUGACATCUGA | 663 |
| TCTCAGCAGCCUGACATCUAA | 664 |
| GCTCCGGAGCCUGGCATCUGA | 665 |
| GTTGAACAGCCUGACATCUGA | 666 |
| ACTCAGCAGCCUGACAACUGA | 667 |
| GCTAAACAGCCUGACTTCUGA | 668 |
| CGTCCGCAGCCUGACATCUGA | 669 |
| GCTCAACAGUCTGACATCUGA | 670 |

TABLE 4-continued

| IgH V gene FR3 | |
|---|---|
| Sequence | SEQ ID NO. |
| GCTCAGCAGCCUGACCTCUGA | 671 |
| GTTCAACAGCCUGACATCUGA | 672 |
| AATGACCAGUCTGAGGTCUGAG | 673 |
| AATGAGCAGUCTGAAGTCUGAG | 674 |
| AATGACCAGUCTAAGGTCUGAG | 675 |
| AATGAGCCAUCTGAAGTCUGAG | 676 |
| AATGAGCCGUCTGAAGTCUGAG | 677 |
| AATGAGCAGUCTGAGTTCUAAG | 678 |
| AATGAGCAGUCTGAGGTCUGAG | 679 |
| AATGACCAGUCTGAAGUCAGAG | 680 |
| TAAAAATGAACAGUCTCCAAACUGAT | 681 |
| TTAAAATGAACAGUCTGCAAGCUAAT | 682 |
| TTAAAATGAACAGUCTGCAATCUAAT | 683 |
| TTAAAATGAACAGUCTGCAAGCUGAT | 684 |
| TAAAACTGAACAGUCTGCAAACUGAT | 685 |
| TAAAAATGAACAGUCTGCAAACUGAT | 686 |
| TCTATCTGCAAAUGAACAACTTGAAAACUGAG | 687 |
| TCTATCTGCAAAUGAACAACCTGAAAACUGAG | 688 |
| CTGCAAAUGAACAACTTAAGAGCUGAA | 689 |
| CTGCAAAAGAACAGCUTAAGAGCUGAA | 690 |
| CTGCAGAUGAACAGATUAAGAGAGGAA | 691 |
| CTAGAGAUGAACAGATUAAGAGAGGAA | 692 |
| CTGCAGAUGGACAGATUAAGAGAGGAA | 693 |
| CTGCAAAUGAACAGCTTAAGAGCUGAA | 694 |
| CTGCAAATGAACAACUTAAGGGCUGAA | 695 |
| CTGCAUATGAACAGCTUAAGAGCCGAA | 696 |
| CCTGCAGAUGAGCAATGTGCGATCUGAG | 697 |
| CCTGCAGAUGAGCAATGTGCGAUCGGAG | 698 |
| TATCCAGCTGAGCUCTGTGACAAAUGAG | 699 |
| CCTCCAAUTGAACTCTGUGACCACAGAG | 700 |
| TCTGCAAUTGAACTCTGUGACCACAGAG | 701 |
| CTTTAAAATGAGCAGUCTGCAAAGUGAA | 702 |
| CCTGCAAAUGAGCAAAGTGAGATCUGAG | 703 |
| AGTTGAGTTCUGTGACTACUGAGG | 704 |
| AAATGAACTCUTTGACTGCUGAGG | 705 |
| AGTTGAATTCUGTGACTTCUGAGG | 706 |
| AAATGAACTCUTTGACTGCUGAAG | 707 |
| AGTTGAACTCUGTGACTACUGAAG | 708 |

TABLE 4-continued

IgH V gene FR3

| Sequence | SEQ ID NO. |
|---|---|
| AGTTGAATTCUGTGACTACUGAGG | 709 |
| AGTTGAACUCTGTGACTATUGAAG | 710 |
| CTTCAAATGAACACCCUGAGGGCUGAG | 711 |
| CTTCAGATGAAUGCCCTGAGAGCUGAG | 712 |
| CTTCAAATGAAUGCCCTGAGAGCUGAG | 713 |
| CTTCAAATGAACACCCUGAGAGCUGAG | 714 |
| CAGATCAACAACCUCAAAAAUCAG | 715 |
| CAGATAAGCAACCUCAAAAAUGAG | 716 |
| CAGATCAACAACCUCAAAAAUGAG | 717 |
| TATTCCTCAAGAUCACCAGTGTGGACACUGCA | 718 |
| TATTCCTCAAGAUCGCCAGTGTGGACACUGCA | 719 |
| TATTCCTCAAGAUCGCCAATGTGGACACUGCA | 720 |
| TATTCCTCAAGAUCACCACTGTGGACACUGCA | 721 |
| TATTCCTCAAGAUCACCACTGTGGACACTGUA | 722 |
| CAGCAGCCUGACATCUGAGGAC | 723 |
| CAACAGUCTGACATCUGAGGAC | 724 |
| TGCCAGAUTGACATCUGAGGAT | 725 |
| CAGCAGCCUGACATCUAAGGAC | 726 |
| CAGAAGCCUGACATCUGAG | 727 |
| CAACAGCCUGACATCUGAGGAT | 728 |
| CAGCAGCCUCACATCUGAGGAC | 729 |
| GAGCAGCCUGACATAUGAGGAC | 730 |
| CAGCAGCUTGACATCUGAGGAC | 731 |
| CAGCCGAUTAACATCTGAUGAC | 732 |
| CAGCAGCCUGACAAAUGAGGAC | 733 |
| CAGCAGCCUGACAACUGAGGAC | 734 |
| TAGTAGAUTGACATCUGAAGAC | 735 |
| CAGCAGCCCGACAUCUGAGGAC | 736 |
| CAGCAGCCUGACATCUGAAGAC | 737 |
| AAACAGCCUGACTTCUGAGGAC | 738 |
| GAGCAGCCUGACATCUGAGGAC | 739 |
| CAGAAGCCUGACATCUGAGGAC | 740 |
| CCACAGCCUGACATCUGAGGAC | 741 |
| CCGCAGCCUGACATCUGAGGAC | 742 |
| CAGCAGCCUGACATCTGAUGAC | 743 |
| CAAGAGCCUGACATCUGAGGAC | 744 |
| CAGCAGCCUGACCTCUGAGGAC | 745 |
| CCGGAGCCUGGCATCUGAGGAC | 746 |

TABLE 4-continued

IgH V gene FR3

| Sequence | SEQ ID NO. |
|---|---|
| CAACAGCCUGACATCUGAGGAC | 747 |
| CAACAGCCUGACATCUGAAGAC | 748 |
| CCTGAGCCUGACATCUGAGGAC | 749 |
| CAGCAGCCUAACATCUGAGGAC | 750 |
| CAGCAGCCUGGCATCUGAGGAC | 751 |
| GAACAGCCUGACATCUGAGGAC | 752 |
| CAGCAGCCUGACTTCUGAGAAC | 753 |
| CAACAGUCTGACAUCCGAGGAC | 754 |
| CCGGAGCCUGACATCUGAGGAC | 755 |
| CCGCAGCCUGACAUCGGAGGAT | 756 |
| CAGCAGCCUGACATCUGACGAC | 757 |
| GACCAGUCTGAGGTCUGAGGAC | 758 |
| GAGCAGUCTGAGTTCUAAGGAC | 759 |
| GAGCCAUCTGAAGTCUGAGGAC | 760 |
| GACCAGUCTAAGGTCUGAGGAC | 761 |
| GAGCAGUCTGAAGTCUGAGGAC | 762 |
| GAGCCGUCTGAAGTCUGAGGAC | 763 |
| GAGCAGUCTGAGGTCUGAGGAC | 764 |
| GACCAGUCTGAAGUCAGAGGAC | 765 |
| AAATGAACAGUCTGCAAGCTAAUGAC | 766 |
| AAATGAACAGUCTCCAAACTGAUGAC | 767 |
| AAATGAACAGTCUGCAAGCTGAUGAC | 768 |
| AAATGAACAGUCTGCAAACTGAUGAC | 769 |
| AAATGAACAGUCTGCAATCTAAUGAC | 770 |
| AACTGAACAGUCTGCAAACTGAUGAC | 771 |
| CTGCAAAUGAACAACTTGAAAACUGAGGAC | 772 |
| CTGCAAAUGAACAACCTGAAAACUGAGGAC | 773 |
| CAAATGAACAGCUTAAGAGCUGAAGAC | 774 |
| CAUATGAACAGCTUAAGAGCCGAAGAT | 775 |
| CAAAAGAACAGCUTAAGAGCUGAAGAT | 776 |
| CAAATGAACAACUTAAGAGCUGAAGAC | 777 |
| CAGAUGAACAGATUAAGAGAGGAAGAC | 778 |
| GAGAUGAACAGATUAAGAGAGGAAGAC | 779 |
| CAAATGAACAACUTAAGGGCUGAAGAC | 780 |
| CAGAUGGACAGATUAAGAGAGGAAGAC | 781 |
| CCAGCTGAGCUCTGTGACAAAUGAGGAC | 782 |
| GCAAATGAGCAAAGUGAGATCUGAGGAC | 783 |
| CCAAUTGAACTCTGUGACCACAGAGGAC | 784 |

TABLE 4-continued

| IgH V gene FR3 | |
|---|---|
| Sequence | SEQ ID NO. |
| TAAAATGAGCAGUCTGCAAAGUGAAGAC | 785 |
| GCAGATGAGCAAUGTGCGAUCGGAGGAC | 786 |
| GCAAUTGAACTCTGUGACCACAGAGGAC | 787 |
| GCAGATGAGCAAUGTGCGATCUGAGGAC | 788 |
| TTGAACTCUGTGACTACUGAAGA | 789 |
| ATGAACTCUTTGACTGCUGAGGA | 790 |
| TTGAATTCUGTGACTTCUGAGGA | 791 |
| TTGAGTTCUGTGACTACUGAGGA | 792 |
| TTGAACTCUGTGACTATUGAAGA | 793 |
| TTGAATTCUGTGACTACUGAGGA | 794 |
| ATGAACTCUTTGACTGCUGAAGA | 795 |
| CAGATGAAUGCCCTGAGAGCUGAGGAC | 796 |
| CAAATGAACACCCUGAGAGCUGAGGAC | 797 |
| CAAATGAAUGCCCTGAGAGCUGAGGAC | 798 |
| CAAATGAACACCCUGAGGGCUGAGGAC | 799 |
| CAAATGAACACCCUGAGAGCUGAGGCC | 800 |
| CAACAACCUCAAAAAUCAGGAC | 801 |
| AAGCAACCUCAAAAAUGAGGAC | 802 |
| CAACAACCUCAAAAAUGAGGAC | 803 |
| AAGATCGCCAAUGTGGACACUGCAGAT | 804 |
| AAGATCACCACUGTGGACACUGCAGAT | 805 |
| AAGATCACCAGUGTGGACACUGCAGAT | 806 |
| AAGATCGCCAGUGTGGACACUGCAGAT | 807 |
| AAGATCACCACUGTGGACACTGUAGAT | 808 |
| AGCAGCCCGACAUCUGAGGACT | 809 |
| AGCAGCCUGACATCTGAUGACT | 810 |
| GCCAGATUGACATCTGAGGAUT | 811 |
| CGGAGCCUGGCATCUGAGGACT | 812 |
| AACAGCCUGACTTCUGAGGACT | 813 |
| AGAAGCCUGACATCUGAGGACT | 814 |
| AACAGCCUGACATCTGAGGAUT | 815 |
| AGCAGCCUGACATCUGAGGACA | 816 |
| AGAAGCCUGACATCUGAG | 817 |
| AACAGCCUGACATCUGAGGACC | 818 |
| AGCCGATUAACATCTGAUGACT | 819 |
| AGCAGCCUGACTTCUGAGAACT | 820 |
| AGCAGCCUGACCTCUGAGGACT | 821 |
| CTGAGCCUGACATCUGAGGACT | 822 |

TABLE 4-continued

| IgH V gene FR3 | |
|---|---|
| Sequence | SEQ ID NO. |
| AACAGCCUGACATCUGAGGACT | 823 |
| AACAGCCUGACATCUGAAGACT | 824 |
| AGCAGCCUGACATCUGAAGACT | 825 |
| AGCAGCUTGACATCUGAGGACT | 826 |
| AGCAGCCUGACATCUGAGGACT | 827 |
| AAGAGCCUGACATCUGAGGACT | 828 |
| AGCAGCCUGACAACUGAGGACT | 829 |
| CGCAGCCUGACATCUGAGGACT | 830 |
| AGCAGCCUGGCATCUGAGGACT | 831 |
| AGCAGCCUGACATCUAAGGACT | 832 |
| AGTAGAUTGACATCUGAAGACT | 833 |
| CGGAGCCUGACATCUGAGGACT | 834 |
| AGCAGCCUGACATCUGACGACT | 835 |
| CACAGCCUGACATCUGAGGACT | 836 |
| AGCAGCCUAACATCUGAGGACT | 837 |
| AACAGUCTGACAUCCGAGGACT | 838 |
| AACAGTCUGACATCUGAGGACT | 839 |
| AGCAGCCUGACAAAUGAGGACT | 840 |
| AGCAGCCUGACATAUGAGGACT | 841 |
| CGCAGCCUGACATCUGAGGACA | 842 |
| AGCAGCCUCACATCUGAGGACT | 843 |
| CGCAGCCUGACATCGGAGGAUT | 844 |
| GAGCAGUCTGAGGTCUGAGGACA | 845 |
| GACCAGUCTAAGGTCUGAGGACA | 846 |
| GAGCAGUCTGAGTTCUAAGGACA | 847 |
| GACCAGUCTGAGGTCUGAGGACA | 848 |
| GAGCCGUCTGAAGTCUGAGGACA | 849 |
| GACCAGUCTGAAGUCAGAGGACA | 850 |
| GAGCCAUCTGAAGTCUGAGGACA | 851 |
| GAGCAGUCTGAAGTCUGAGGACA | 852 |
| AAATGAACAGUCTGCAATCTAAUGACA | 853 |
| AACTGAACAGUCTGCAAACTGAUGACA | 854 |
| AAATGAACAGUCTGCAAGCTAAUGACA | 855 |
| AAATGAACAGTCUGCAAGCTGAUGACA | 856 |
| AAATGAACAGUCTGCAAACTGAUGACA | 857 |
| AAATGAACAGUCTCCAAACTGAUGACA | 858 |
| CAAATGAACAACCUGAAAACUGAGGACA | 859 |
| CAAATGAACAACUTGAAAACUGAGGACA | 860 |

TABLE 4-continued

| IgH V gene FR3 | |
|---|---|
| Sequence | SEQ ID NO. |
| ATGAACAACUTAAGAGCUGAAGACA | 861 |
| ATGAACAACUTAAGGGCUGAAGACA | 862 |
| ATGAACAGCUTAAGAGCUGAAGACA | 863 |
| AUGGACAGATUAAGAGAGGAAGACA | 864 |
| AAGAACAGCTUAAGAGCTGAAGAUA | 865 |
| AUGAACAGATUAAGAGAGGAAGACA | 866 |
| ATGAACAGCTUAAGAGCCGAAGAUA | 867 |
| CAAATGAGCAAAGUGAGATCUGAGGACA | 868 |
| CAGATGAGCAAUGTGCGATCUGAGGACA | 869 |
| CAGATGAGCAAUGTGCGATCUGAGGACC | 870 |
| CAAUTGAACTCTGUGACCACAGAGGACA | 871 |
| CAGATGAGCAAUGTGCGAUCGGAGGACA | 872 |
| AAAATGAGCAGUCTGCAAAGUGAAGACA | 873 |
| CAGCTGAGCUCTGTGACAAAUGAGGACA | 874 |
| GAACTCTGUGACTACTGAAGAUA | 875 |
| GAATTCTGUGACTTCUGAGGACA | 876 |
| GAACTCTGUGACTATTGAAGAUA | 877 |
| GAATTCUGTGACTACUGAGGACG | 878 |
| GAACTCTUTGACTGCUGAGGACA | 879 |
| GAATTCTGUGACTACUGAGGACA | 880 |
| GAACTCTUTGACTGCUGAAGACA | 881 |
| GAGTTCUGTGACTACUGAGGACA | 882 |
| TCAAATGAAUGCCCTGAGAGCUGAGGACA | 883 |
| TCAAATGAACACCCUGAGAGCUGAGGACA | 884 |
| TCAAATGAACACCCUGAGGGCUGAGGACA | 885 |
| TCAAATGAACACCCUGAGAGCUGAGGCCA | 886 |
| TCAGATGAAUGCCCTGAGAGCUGAGGACA | 887 |
| AACCUCAAAAAUGAGGACA | 888 |
| AACCUCAAAAAUCAGGACA | 889 |
| AAGATCGCCAATGUGGACACTGCAGAUA | 890 |
| AAGATCGCCAGTGUGGACACTGCAGAUA | 891 |
| AAGATCACCACTGUGGACACTGCAGAUA | 892 |
| AAGATCACCAGTGUGGACACTGCAGAUA | 893 |
| AAGATCACCACTGUGGACACTGTAGAUA | 894 |
| CGCAGCCUGACATCTGAGGACUC | 895 |
| CACAGCCTGACAUCTGAGGACUC | 896 |
| AGCAGCCTCACAUCTGAGGACUC | 897 |
| AGCAGCCTGACUTCTGAGAACUC | 898 |

TABLE 4-continued

| IgH V gene FR3 | |
|---|---|
| Sequence | SEQ ID NO. |
| AGCAGCCUGACATATGAGGACUC | 899 |
| AACAGCCTGACUTCTGAGGACUC | 900 |
| AACAGCCTGACAUCTGAGGACUT | 901 |
| AGCAGCCTGACAUCTGACGACUC | 902 |
| AGCAGCCUGACATCTGAAGACUC | 903 |
| AGCAGCCUGACATCUGAGGACAC | 904 |
| AACAGCCTGACAUCTGAAGACUC | 905 |
| AGCCGATTAACAUCTGATGACUC | 906 |
| AACAGCCTGACAUCTGAGGATUC | 907 |
| AGAAGCCUGACATCUGAG | 908 |
| AGCAGCCUGACAAATGAGGACUC | 909 |
| AACAGTCTGACAUCTGAGGACUC | 910 |
| AGCAGCCUGACATCTGATGACUC | 911 |
| AGCAGCCTGGCAUCTGAGGACUC | 912 |
| AGCAGCCCGACAUCTGAGGACUC | 913 |
| AACAGCCTGACAUCTGAGGACUC | 914 |
| AGCAGCTTGACAUCTGAGGACUC | 915 |
| AGCAGCCUGACATCTAAGGACUC | 916 |
| CGGAGCCUGGCATCTGAGGACUC | 917 |
| AGCAGCCUGACAACTGAGGACUC | 918 |
| CGCAGCCUGACATCGGAGGATUC | 919 |
| AGAAGCCTGACAUCTGAGGACUC | 920 |
| AGCAGCCTGACAUCTGAGGACUC | 921 |
| AGTAGATTGACAUCTGAAGACUC | 922 |
| AACAGTCTGACAUCCGAGGACUC | 923 |
| AGCAGCCTGACCUCTGAGGACUC | 924 |
| GCCAGATTGACAUCTGAGGATUC | 925 |
| CGGAGCCUGACATCTGAGGACUC | 926 |
| AAGAGCCTGACAUCTGAGGACUC | 927 |
| CTGAGCCTGACAUCTGAGGACUT | 928 |
| AACAGCCUGACATCUGAGGACCC | 929 |
| CGCAGCCUGACATCUGAGGACAC | 930 |
| AGCAGCCTAACAUCTGAGGACUC | 931 |
| AGCAGUCTGAAGTCUGAGGACAC | 932 |
| ACCAGUCTGAAGUCAGAGGACAC | 933 |
| AGCCAUCTGAAGTCUGAGGACAC | 934 |
| ACCAGUCTGAGGTCUGAGGACAC | 935 |
| ACCAGUCTAAGGTCUGAGGACAC | 936 |

TABLE 4-continued

IgH V gene FR3

| Sequence | SEQ ID NO. |
|---|---|
| AGCAGUCTGAGGTCUGAGGACAC | 937 |
| AGCAGUCTGAGTTCUAAGGACAC | 938 |
| AGCCGUCTGAAGTCUGAGGACAC | 939 |
| GAACAGTCUGCAAGCTAAUGACAC | 940 |
| GAACAGTCUCCAAACTGAUGACAC | 941 |
| GAACAGTCUGCAAACTGAUGACAC | 942 |
| GAACAGTCUGCAATCTAAUGACAC | 943 |
| GAACAGTCUGCAAGCTGAUGACAC | 944 |
| TGAACAACUTGAAAACUGAGGACAC | 945 |
| TGAACAACCUGAAAACUGAGGACAC | 946 |
| ATATGAACAGCTUAAGAGCCGAAGAUAC | 947 |
| AAATGAACAGCUTAAGAGCUGAAGACAC | 948 |
| AAAAGAACAGCTUAAGAGCTGAAGAUAC | 949 |
| AGAUGGACAGATUAAGAGAGGAAGACAC | 950 |
| AAATGAACAACUTAAGAGCUGAAGACAT | 951 |
| AGAUGAACAGATUAAGAGAGGAAGACAC | 952 |
| AAATGAACAACUTAAGGGCUGAAGACAC | 953 |
| AAATGAACAACUTAAGAGCUGAAGACAC | 954 |
| AAATGAGCAAAGUGAGATCUGAGGACAC | 955 |
| AAATGAGCAGUCTGCAAAGUGAAGACAC | 956 |
| AAUTGAACTCTGUGACCACAGAGGACAC | 957 |
| AGATGAGCAAUGTGCGATCUGAGGACCC | 958 |
| AGATGAGCAAUGTGCGAUCGGAGGACAC | 959 |
| AGATGAGCAAUGTGCGATCUGAGGACAC | 960 |
| AGCTGAGCUCTGTGACAAAUGAGGACAC | 961 |
| AACTCTGUGACTATTGAAGAUAT | 962 |
| AACTCTGTGACUACTGAAGAUAT | 963 |
| AATTCUGTGACTACUGAGGACGC | 964 |
| AACTCUTTGACTGCUGAGGACAC | 965 |
| AACTCUTTGACTGCUGAAGACAC | 966 |
| AATTCUGTGACTACUGAGGACAC | 967 |
| AGTTCUGTGACTACUGAGGACAC | 968 |
| AATTCUGTGACTTCUGAGGACAC | 969 |
| TCAAATGAAUGCCCTGAGAGCUGAGGACA | 970 |
| TCAAATGAACACCCUGAGAGCUGAGGACA | 971 |
| TCAAATGAACACCCUGAGGGCUGAGGACA | 972 |
| TCAAATGAACACCCUGAGAGCUGAGGCCA | 973 |
| TCAGATGAAUGCCCTGAGAGCUGAGGACA | 974 |

TABLE 4-continued

IgH V gene FR3

| Sequence | SEQ ID NO. |
|---|---|
| CAACCUCAAAAAUCAGGACAC | 975 |
| CAACCUCAAAAAUGAGGACAC | 976 |
| CAACCUCAAAAAUGAGGACAT | 977 |
| AGATCACCACTGUGGACACTGTAGAUAC | 978 |
| AGATCGCCAATGUGGACACTGCAGAUAC | 979 |
| AGATCACCAGTGUGGACACTGCAGAUAC | 980 |
| AGATCGCCAGTGUGGACACTGCAGAUAC | 981 |
| AGATCACCACTGUGGACACTGCAGAUAC | 982 |

TABLE 5

IgH J gene

| Sequence | SEQ ID NO. |
|---|---|
| GACTGTGAGAGTGGTGCCTT | 983 |
| GACAGTGACCAGAGTCCCTT | 984 |
| GACGGTGACCGTGGTCCCTG | 985 |
| GACTGTGAGACTGGTGCCTT | 986 |
| GACTGTGAGAGAGGTGCCTT | 987 |
| GACGGTGACTGAGGTTCCTT | 988 |
| AACGGTGACCGTGGTCCCTG | 989 |
| GAGACGGTGACTGAGGTTCC | 990 |
| GAGACTGTGAGACTGGTGCC | 991 |
| GAGACGGTGACCGTGGTCCC | 992 |
| GAAACGGTGACCGTGGTCCC | 993 |
| GAGACTGTGAGAGTGGTGCC | 994 |
| GAGACAGTGACCAGAGTCCC | 995 |
| GAGACTGTGAGAGAGGTGCC | 996 |
| AGACGGTGACTGAGGTTCC | 997 |
| AGACGGTGACCGTGGTCCC | 998 |
| AGACTGTGAGACTGGTGCC | 999 |
| AAACGGTGACCGTGGTCCC | 1000 |
| AGACTGTGAGAGAGGTGCC | 1001 |
| AGACAGTGACCAGAGTCCC | 1002 |
| AGACTGTGAGAGTGGTGCC | 1003 |
| GACTGTGAGAGTGGTGCCT | 1004 |
| GACGGTGACCGTGGTCCCT | 1005 |
| AACGGTGACCGTGGTCCCT | 1006 |
| GACAGTGACCAGAGTCCCT | 1007 |
| GACGGTGACTGAGGTTCCT | 1008 |

TABLE 5-continued

| IgH J gene | |
|---|---|
| Sequence | SEQ ID NO. |
| GACTGTGAGAGAGGTGCCT | 1009 |
| GACTGTGAGACTGGTGCCT | 1010 |
| CTGAGGAGACTGTGAGAGTGG | 1011 |
| CTGAGGAGACGGTGACTGAGG | 1012 |
| CTGAGGAGACTGTGAGACTGG | 1013 |
| CTGAGGAGACTGTGAGAGAGG | 1014 |
| CTGCAGAGACAGTGACCAGAG | 1015 |
| CTGAGGAGACGGTGACCGTGG | 1016 |
| CTGAGGAAACGGTGACCGTGG | 1017 |
| GACTGTGAGAGUGGTGCCUT | 1018 |
| GACAGUGACCAGAGTCCCUT | 1019 |
| GACGGTGACCGUGGTCCCUG | 1020 |
| GACTGTGAGACUGGTGCCUT | 1021 |
| GACTGUGAGAGAGGTGCCUT | 1022 |
| GACGGTGACUGAGGTTCCUT | 1023 |
| AACGGTGACCGUGGTCCCUG | 1024 |
| GAGACGGUGACTGAGGTUCC | 1025 |
| GAGACTGUGAGACTGGUGCC | 1026 |
| GAGACGGUGACCGTGGUCCC | 1027 |
| GAAACGGUGACCGTGGUCCC | 1028 |
| GAGACTGUGAGAGTGGUGCC | 1029 |
| GAGACAGUGACCAGAGUCCC | 1030 |
| GAGACTGUGAGAGAGGUGCC | 1031 |
| AGACGGUGACTGAGGTUCC | 1032 |
| AGACGGUGACCGTGGUCCC | 1033 |
| AGACTGUGAGACTGGUGCC | 1034 |
| AAACGGUGACCGTGGUCCC | 1035 |
| AGACTGUGAGAGAGGUGCC | 1036 |
| AGACAGUGACCAGAGUCCC | 1037 |
| AGACTGUGAGAGTGGUGCC | 1038 |
| GACTGUGAGAGTGGUGCCT | 1039 |
| GACGGUGACCGTGGUCCCT | 1040 |
| AACGGUGACCGTGGUCCCT | 1041 |
| GACAGUGACCAGAGUCCCT | 1042 |
| GACGGUGACTGAGGTUCCT | 1043 |
| GACTGUGAGAGAGGUGCCT | 1044 |
| GACTGUGAGACTGGUGCCT | 1045 |
| CTGAGGAGACUGTGAGAGUGG | 1046 |

TABLE 5-continued

| IgH J gene | |
|---|---|
| Sequence | SEQ ID NO. |
| CTGAGGAGACGGUGACUGAGG | 1047 |
| CTGAGGAGACUGTGAGACUGG | 1048 |
| CUGAGGAGACTGUGAGAGAGG | 1049 |
| CUGCAGAGACAGUGACCAGAG | 1050 |
| CTGAGGAGACGGUGACCGUGG | 1051 |
| CTGAGGAAACGGUGACCGUGG | 1052 |

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

EXAMPLES

Provided immune repertoire compositions include, without limitation, reagents designed for library preparation and sequencing of murine expressed TCR beta sequences, rearranged genomic TCR beta sequences, expressed IgH sequences, and rearranged genomic IgH sequences. Generally, RNAs extracted from samples (e.g., blood samples, sorted cell samples, normal tissue samples, tumor samples (e.g., fresh, frozen, FFPE, of various types)) were reverse transcribed; gDNA was extracted from samples; libraries were generated, templates prepared, e.g., using Ion Chef™ or Ion OneTouch™ 2 System, then prepared templates were sequenced using next generation sequencing technology, e.g., an Ion S5™ System, an Ion PGM™ System and sequence analysis was performed using Ion Reporter™ software. Kits suitable for extracting and/or isolating RNA and genomic DNA from biological samples are commercially available from, for example, Thermo Fisher Scientific, BioChain Institute Inc., and Takara Bio, Inc.

Example 1

The TRB V gene FR3 primers of Table 2 and TRB J gene primers of Table 3 were designed to amplify all currently known expressed or gDNA TCR beta gene rearrangements found in most mouse strains commonly used in laboratory research and disease modeling. In multiplex PCR, a pool of forward and reverse primers selected from Tables 2 and 3 were used as primer pairs in amplifying sequences from the V gene FR3 region to the J gene of TRB cDNA. In the exemplary TRB V gene FR3-J amplification reactions, the multiplex primer set included forward primers SEQ ID NOs: 34-66 and reverse primers SEQ ID NOs: 84-100 and assays were performed on cDNA from different sources.

In separate reactions, total RNA from murine thymus tissue (Zyagen) and Universal Mouse Reference RNA (Thermo Fisher Scientific) was reverse transcribed to cDNA with SuperScript™ IV VILO™ Master Mix (Thermo Fisher Scientific) according to manufacturer instructions. To a single well of a 96-well PCR plate was added 10 microliters prepared cDNA (25 ng), 4 microliters of 1 μM forward and reverse primer pool, 4 microliters of 5× Ion AmpliSeq™ HiFi Mix (Thermo Fisher Scientific), and DNase/RNase free water to bring the final reaction volume to 20 microliters. The PCR plate was sealed, reaction mixtures mixed, and loaded into a thermal cycler (e.g., Veriti™ 96-well thermal cycler (Applied Biosystems)) and run on the following temperature profile to generate the amplicon library. An initial holding stage was performed at 95° C. for 2 minutes, followed by about 20 cycles of a denaturing stage at 95° C. for 30 seconds, an annealing stage at 60° C. for 45 seconds, and an extending stage for 72° C. for 45 seconds. After cycling, a final extension 72° C. for 10 minutes was performed and the amplicon library was held at 10° C. until proceeding. Typically, about 20 cycles are used to generate the amplicon library from cDNA input. For some applications (eg., more or less cDNA starting material, FFPE sourced RNA, etc), cycle number may be reduced (e.g., −3) or increased (e.g., +3, +6, up to 30 cycles).

The amplicon sample was briefly centrifuged to collect contents before proceeding. To the amplicon library (~20 microliters), 2 microliters of FuPa reagent was added. The reaction mixture was sealed, mixed thoroughly to ensure uniformity and incubated at 50° C. for 10 minutes, 55° C. for 10 minutes, 60° C. for 20 minutes, then held at 10° C. for up to 1 hour. The sample was briefly centrifuged to collect contents before proceeding to a ligation step. The reaction mixture now containing the phosphorylated amplicon library was combined with 2 microliters of Ion Torrent™ Dual Barcode Adapters (Thermo Fisher Scientific), 4 microliters of AmpliSeq Plus Switch Solution (sold as a component of the Ion AmpliSeq™ Library Kit Plus, Thermo Fisher Scientific) and 2 microliters of DNA ligase, added last (sold as a component of the Ion AmpliSeq™ Library Kit Plus, Thermo Fisher Scientific), then incubated at the following: 22° C. for 30 minutes, 68° C. for 5 minutes, 72° C. for 5 minutes, then held at 10° C. for up to 1 hour. The sample was briefly centrifuged to collect contents before proceeding to a library purification step.

After the ligation step incubation, 45 microliters (1.5× sample volume) of room temperature AMPure® XP beads (Beckman Coulter) was added to ligated DNA and the mixture was pipetted thoroughly to mix the bead suspension with the DNA. The mixture was incubated at room temperature for 5 minutes, placed on a magnetic rack such as a DynaMag™-96 side magnet (Invitrogen, Part No. 12331D) for two minutes. After the solution had cleared, the supernatant was discarded. Without removing the plate from the magnetic rack, 150 microliters of freshly prepared 70% ethanol was introduced into the sample, and incubated while gently rotating the tube on the magnetic rack. After the solution cleared, the supernatant was discarded without disturbing the pellet. A second ethanol wash was performed, the supernatant discarded, and any remaining ethanol was removed by pulse-spinning the tube and carefully removing residual ethanol while not disturbing the pellet. The pellet was air-dried for about 5 minutes at room temperature. The ligated DNA was eluted from the beads in 50 microliters of low TE buffer.

The eluted libraries were quantitated by qPCR using the Ion Library TaqMan® Quantitation Kit (Ion Torrent, Cat. No. 4468802), according to manufacturer instructions. After quantification, the libraries were diluted to a concentration of about 25 μM.

The libraries were normalized to 25 pM and aliquots of the final libraries were used in template preparation and chip loading using the Ion Chef™ instrument according to the manufacturer instructions. Sequencing was performed using Ion 540™ chips on the Ion S5™ System according to manufacturer instructions, and gene sequence analysis was performed with the Ion Torrent Suite™ software. Since the sequences were generated from use of J gene primers, they were subjected to a J gene sequence inference process involving adding the inferred J gene sequence to the sequence read to create an extended sequence read, aligning the extended sequence read to a reference sequence, and identifying productive reads, as described herein. In addition, all of the generated sequence data was further subjected to the error identification and removal programs provided herein.

Exemplary results from the TRB FR3-J assay using starting samples of murine thymus total RNA and a Universal Mouse Reference RNA are shown in Table 6. Each of these assays yielded libraries in which about 70% were productive. Evenness, also referred to as Clone Normalized Shannon Entropy, describes how even clone representation is in the sample; the closer to 1.0, the more evenly sized the clonal populations are.

TABLE 6

| Library | Total Reads | Mean Read Length (nt) | % Productive Reads | Clones Identified | Clone Shannon Diversity | Evenness |
|---|---|---|---|---|---|---|
| Thymus RNA | 6,739,244 | 85 | 69.0 | 157061 | 16.5438 | 0.9585 |
| Thymus RNA | 6,674,723 | 85 | 69.2 | 153003 | 16.5111 | 0.9587 |
| Thymus RNA | 7,477,470 | 84 | 69.6 | 167541 | 16.6365 | 0.9586 |
| Universal RNA | 4,346,260 | 81 | 69.6 | 10103 | 12.7999 | 0.9622 |
| Universal RNA | 3,011,711 | 81 | 69.8 | 10380 | 12.8183 | 0.9608 |
| Universal RNA | 3,986,538 | 81 | 69.7 | 10056 | 12.7905 | 0.9620 |

Example 2

Universal mouse genomic DNA (Takara Bio, Inc.) was used in multiplex polymerase chain reactions with a set of forward primers from the TRB V gene FR3 region and reverse primers from theTRB J gene as primer pairs in amplifying sequences from the V gene FR3 region to the J gene of rearranged TCR beta gDNA. The exemplary set of forward and reverse primers were selected from Tables 2 and 3 and included forward primers SEQ ID NOs: 34-66 and reverse primers SEQ ID NOs: 84-100. Assays were performed in replicate with varying amounts of input gDNA: 100 ng, 250 ng, 500 ng, 800 ng, and 1000 ng.

To a single well of a 96-well PCR plate was added the mouse gDNA (100, 250, 500, 800, or 1000 ng), 4 microliters of 1 μM Primer Mix (FR3 forward primers and J reverse primers, 1 μM each), 4 microliters of 5× Ion AmpliSeq™ HiFi Mix (Invitrogen, Catalog No. 11304), 2 microliters of dNTP Mix (dGTP, dCTP, dATP, and dTTP; 7.5 mM each) and DNase/RNase free water to bring the final reaction volume to 20 microliters.

The PCR plate was sealed, reaction mixtures mixed, and the plate loaded into a thermal cycler (e.g., Veriti™ 96-well thermal cycler (Applied Biosystems)) and run on the following temperature profile to generate the amplicon library. An initial holding stage was performed at 95° C. for 2 minutes, followed by about 25 cycles of a denaturing stage at 95° C. for 30 seconds, an annealing stage at 60° C. for 45 seconds, and an extending stage for 72° C. for 45 seconds. After cycling, a final extension 72° C. for 10 minutes was performed and the amplicon library was held at 10° C. until proceeding. Typically, about 25 cycles are used to generate the amplicon library from gDNA input. For some applications (eg., more or less gDNA starting material, FFPE sourced samples, etc), cycle number may be reduced (e.g., −3, −6) or increased (e.g., +3, +6, up to 30 cycles).

Amplicon and library preparation, chip loading, sequencing and sequence data processing was performed as described in Example 1. Exemplary results from the TRB FR3-J assay using varying input amounts of universal mouse gDNA are shown in Table 7. Each of these assays yielded libraries in which about 51-56% were productive and the mean sequence read length was about 81 nucleotides.

TABLE 7

| Library | Total Reads | Mean Read Length (nt) | % Productive Reads | Clones Identified | Clone Shannon Diversity | Evenness |
|---|---|---|---|---|---|---|
| 100 ng_Rep1 | 5,086,218 | 80 | 55.9 | 5661 | 11.8289 | 0.9488 |
| 100 ng_Rep2 | 4,416,887 | 81 | 53.7 | 5743 | 11.8139 | 0.9461 |
| 250 ng_Rep1 | 5,194,502 | 81 | 51.6 | 13177 | 13.0286 | 0.952 |
| 250 ng_Rep2 | 4,696,469 | 81 | 52.6 | 13539 | 13.0975 | 0.9543 |
| 500 ng_Rep1 | 5,421,416 | 81 | 51.6 | 20457 | 13.6035 | 0.9499 |
| 500 ng_Rep2 | 4,913,704 | 81 | 52.4 | 20991 | 13.6469 | 0.9505 |
| 800 ng_Rep1 | 5,574,483 | 81 | 53.4 | 27333 | 13.9284 | 0.945 |
| 800 ng_Rep2 | 5,406,053 | 81 | 52.2 | 28047 | 13.9628 | 0.945 |
| 1000 ng_Rep1 | 4,162,978 | 81 | 53.6 | 28474 | 13.9676 | 0.9439 |
| 1000 ng_Rep2 | 4,105,409 | 81 | 54.2 | 28857 | 13.9482 | 0.9414 |

Example 3

The IgH V gene FR3 primers of Table 4 and IgH J gene primers of Table 5 were designed to amplify all currently known expressed or gDNA IgH gene rearrangements found in most mouse strains commonly used in laboratory research and disease modeling. A variety of primer sets for amplifying sequences from the V gene FR3 region to the J gene of IgH cDNA or gDNA were generated using forward primers selected from Table 4 and reverse primers selected from Table 5. Exemplary IgH FR3-J primer set panels for multiplex amplification are provided in Table 8, with each primer in the pool at a 1 micromolar concentration.

TABLE 8

| FR3-J Primer Set | SEQ ID NOS |
|---|---|
| 1 | 542-633, 1018-1024 |
| 2 | 634-722, 1025-1031 |
| 3 | 723-808, 1032-1038 |
| 4 | 809-894, 1039-1045 |
| 5 | 895-982, 1046-1052 |

cDNA was prepared from Universal Mouse Reference RNA (Thermo Fisher Scientific) as described in Example 1. Universal Mouse Reference RNA is an RNA extract from pooled samples of normal mouse tissue. Replicate multiplex amplification reactions were performed using 25 ng of the cDNA and a primer set of Table 8, libraries were prepared from the resulting amplicons and the libraries sequenced as described in Example 1. Exemplary assay results from these IgH primer sets are shown in Table 9.

TABLE 9

| Library | Total Reads | Mean Read Length (nt) | % Productive Reads | Clones Identified | Clone Shannon Diversity | Evenness |
|---|---|---|---|---|---|---|
| 1_Rep1 | 5,166,190 | 78 | 79.4 | 40574 | 9.9651 | 0.6510 |
| 1_Rep2 | 7,029,541 | 78 | 78.5 | 50356 | 10.2152 | 0.6540 |
| 2_Rep1 | 4,513,553 | 79 | 79.0 | 40129 | 10.4762 | 0.6851 |
| 2_Rep2 | 4,043,864 | 79 | 78.0 | 35335 | 10.3757 | 0.6867 |
| 3_Rep1 | 2,980,061 | 77 | 78.7 | 28672 | 10.4489 | 0.7057 |
| 3_Rep2 | 3,048,312 | 78 | 79.6 | 30125 | 10.5717 | 0.7105 |
| 4_Rep1 | 2,120,393 | 76 | 80.4 | 21561 | 10.2036 | 0.7088 |
| 4_Rep2 | 802,850 | 76 | 78.9 | 9421 | 9.4884 | 0.7187 |
| 5_Rep1 | 1,224,356 | 78 | 79.7 | 12349 | 9.5617 | 0.7035 |
| 5_Rep2 | 5,216,448 | 79 | 78.3 | 41926 | 10.3183 | 0.6720 |

Universal mouse genomic DNA (Takara Bio, Inc.) was used in multiplex polymerase chain reactions with the IgH FR3-J primer sets of Table 8. Replicate multiplex amplification reactions were performed using 500 ng of the gDNA and a primer set of Table 8, libraries were prepared from the resulting amplicons and the libraries sequenced as described in Example 2. Exemplary assay results from these IgH primer sets are shown in Table 10.

TABLE 10

| Library | Total Reads | Mean Read Length (nt) | % Productive Reads | Clones Identified | Clone Shannon Diversity | Evenness |
|---|---|---|---|---|---|---|
| 1_Rep1 | 838,771 | 75 | 61.6 | 8295 | 12.6489 | 0.9716 |
| 1_Rep2 | 953,477 | 75 | 61.1 | 8599 | 12.6919 | 0.9711 |
| 2_Rep1 | 440,339 | 72 | 64.5 | 8802 | 12.8439 | 0.9802 |
| 2_Rep2 | 1,846,350 | 72 | 63.6 | 10352 | 13.0088 | 0.9753 |
| 3_Rep1 | 1,009,051 | 71 | 61.6 | 9623 | 12.9483 | 0.9785 |
| 3_Rep2 | 822,938 | 71 | 61.8 | 9517 | 12.9482 | 0.9797 |
| 4_Rep1 | 1,937,402 | 71 | 62.0 | 10516 | 13.0977 | 0.9803 |
| 4_Rep2 | 892,948 | 71 | 62.3 | 9983 | 13.0454 | 0.9819 |
| 5_Rep1 | 1,652,744 | 74 | 60.9 | 13213 | 13.3187 | 0.9729 |
| 5_Rep2 | 1,183,841 | 74 | 61.3 | 12926 | 13.2988 | 0.9737 |

Multiplex amplification reactions were performed with varying amounts of universal mouse genomic DNA (Takara Bio, Inc.) as input. These assays were performed in replicate with the IgH FR3-J primer set 1 of Table 8 with varying amounts of input gDNA: 100 ng, 250 ng, 500 ng, 800 ng, and 1000 ng. The amplification reactions were performed, libraries prepared from the resulting amplicons and the libraries sequenced as described in Example 2. Exemplary results from the IgH FR3-J assay using varying input amounts of mouse gDNA are shown in Table 11.

TABLE 11

| Library | Total Reads | Mean Read Length (nt) | % Productive Reads | Clones Identified | Clone Shannon Diversity | Evenness |
|---|---|---|---|---|---|---|
| 100 ng_Rep1 | 2,790,439 | 75 | 61.4 | 4437 | 11.6035 | 0.9577 |
| 100 ng_Rep2 | 2,339,280 | 75 | 62.7 | 4507 | 11.6338 | 0.9585 |
| 250 ng_Rep1 | 4,146,160 | 75 | 60.7 | 10301 | 12.851 | 0.964 |
| 250 ng_Rep2 | 4,018,503 | 75 | 60.5 | 10250 | 12.8388 | 0.9636 |
| 500 ng_Rep1 | 3,917,557 | 74 | 60.5 | 17690 | 13.6326 | 0.9661 |
| 500 ng_Rep2 | 5,690,043 | 74 | 63.0 | 18823 | 13.6806 | 0.9634 |
| 800 ng_Rep1 | 5,208,066 | 74 | 59.9 | 26175 | 14.2494 | 0.9709 |
| 800 ng_Rep2 | 3,806,043 | 74 | 59.7 | 24970 | 14.1329 | 0.9675 |
| 1000 ng_Rep1 | 4,547,674 | 73 | 64.9 | 26097 | 14.0936 | 0.9606 |
| 1000 ng_Rep2 | 3,194,811 | 73 | 63.5 | 24963 | 14.0546 | 0.9621 |

What is claimed is:

1. A method for amplification of nucleic acid sequences of a murine immune receptor repertoire in a sample, comprising:

performing a single multiplex amplification reaction to amplify target murine immune receptor nucleic acid template molecules using at least one set of:

i) a plurality of V gene primers directed to a majority of different V genes of at least one murine immune receptor coding sequence comprising at least a portion of framework region 3 (FR3) within the V gene; and ii) a plurality of J gene primers directed to at least a portion of a majority of different murine J genes of the at least one murine immune receptor coding sequence;

wherein the nucleic acid template molecules are obtained from RNA or genomic DNA (gDNA) from a biological sample;

wherein each set of i) and ii) primers is directed to coding sequences of the same target murine immune receptor gene selected from a T cell receptor (TCR) gene or a B cell receptor (BCR) gene and wherein performing the amplification using the at least one set of i) and ii) primers results in amplicon molecules representing the target murine immune receptor repertoire in the sample;

wherein each of the plurality of V gene primers and/or the plurality of J gene primers includes one or more cleavable groups located (i) near or at the termini of the primer or (ii) near or about the center nucleotide of the primer;

thereby generating immune receptor amplicon molecules comprising the expressed target murine immune receptor repertoire.

2. The method of claim 1, wherein each of the plurality of V gene primers and the plurality of J gene primers has any one or more of the following criteria:

(1) includes two or more modified nucleotides within the primer, at least one of which is included near or at the termini of the primer and at least one of which is included at, or about the center nucleotide position of the primer;

(2) length is about 15 to about 40 bases in length;

(3) $T_m$ of from above 60° C. to about 70° C.;

(4) has low cross-reactivity with non-target sequences present in the sample;

(5) at least the first four nucleotides (going from 3' to 5' direction) are non-complementary to any sequence within any other primer present in the same reaction; and (6) are non-complementary to any consecutive stretch of at least 5 nucleotides within any other produced target amplicon.

3. The method of claim 1, wherein each of the plurality of V gene primers and/or the plurality of J gene primers includes two or more modified nucleotides having a cleavable group selected from a methylguanine, 8-oxo-guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

4. The method of claim 1, wherein the target immune receptor gene is TCR beta, wherein the plurality of V gene primers comprises at least 25 primers that anneal to at least a portion of the FR3 region of TCR beta nucleic acid template molecules, and wherein the plurality of J gene primers comprises at least ten primers that anneal to at least a portion of the J gene portion of TCR beta nucleic acid template molecules.

5. The method of claim 4, wherein the at least one set of i) and ii) is selected from primers of SEQ ID Nos: 34-66 and SEQ ID NOs: 84-100, respectively.

6. The method of claim 1, wherein the target immune receptor gene is IgH, wherein the plurality of V gene primers comprises at least 70 primers that anneal to at least a portion of the FR3 region of IgH template nucleic acid molecules, and wherein the plurality of J gene primers comprises at least two primers that anneal to at least a portion of the J gene portion of IgH nucleic acid template molecules.

7. The method of claim 6, wherein the at least one set of i) and ii) is selected from primers of SEQ ID Nos: 101-982 and SEQ ID NOs: 983-1052, respectively.

8. A method for preparing a murine immune receptor repertoire library, comprising:

i) treating the target immune receptor amplicon molecules of claim 1 to form blunt-ended amplicon molecules;

ii) ligating at least one adapter to at least one of the treated amplicon molecules, thereby producing a library of adapter-ligated target immune receptor amplicon molecules comprising the target murine immune receptor repertoire.

9. A method for providing sequence of a murine immune receptor repertoire in a biological sample, comprising:

i) performing sequencing of the target immune receptor repertoire library of claim 8;

ii) determining the sequence of the library molecules, wherein determining the sequence includes obtaining initial sequence reads, inferring the sequence of the J gene primer and the target J gene and adding the inferred J gene sequence to the initial sequence read, aligning the initial sequence read to a reference sequence, identifying productive reads, and correcting one or more indel errors to generate rescued productive sequence reads; and iii) reporting the sequences determined for the library molecules, thereby providing sequence of the murine immune receptor repertoire in the sample.

10. A method for identifying a biomarker for a disease or adverse condition, comprising:

performing a single multiplex amplification reaction to amplify target immune receptor nucleic acid template molecules from a sample according to claim 1, wherein the biological sample is from a mouse with a disease or adverse condition;

performing sequencing of the target immune receptor amplicon molecules and determining the sequence of the molecules, wherein determining the sequence includes obtaining initial sequence reads, inferring the sequence of the J gene primer and the target J gene and adding the inferred J gene sequence to the initial sequence read, aligning the initial sequence read to a reference sequence, identifying productive reads, and correcting one or more indel errors to generate rescued productive sequence reads;

identifying BCR or TCR clonal populations from the determined target immune receptor sequences; and identifying the sequence of at least one BCR or TCR clone for use as a biomarker for the disease or adverse condition.

11. The method of claim 10, wherein the disease or adverse condition is selected from cancer, autoimmune disease, infectious disease, allergy, response to vaccination, and response to an immunotherapy treatment.

12. The method of claim 10, wherein the target immune receptor gene is IgH or TCR beta.

13. The method of claim 1, wherein the nucleic acid template molecules comprise cDNA produced by reverse transcribing RNA molecules from the sample.

14. The method of claim 1, wherein the nucleic acid template molecules comprise gDNA from the sample.

15. The method of claim 1, wherein the sample comprises hematopoietic cells, lymphocytes, tumor cells, or cell-free DNA (cfDNA) and is selected from the group consisting of peripheral blood mononuclear cells (PBMCs), B cells, circulating tumor cells, tumor infiltrating lymphocytes, formalin-fixed paraffin-embedded (FFPE) tissue, fresh tissue, frozen tissue, blood, and plasma.

* * * * *

SEQUENCE LISTING

<160> NUMBER OF SEQ ID NOS: 1054

<210> SEQ ID NO 1
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1
ccttttcatc tatgacagtt ttaaatgcat 30

<210> SEQ ID NO 2
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
gaacccaaca tcctaaagtg gggccagcag atc 33

<210> SEQ ID NO 3
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
agagctttcc cctgacatta gagtcaacca gtt 33

<210> SEQ ID NO 4
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
ctcatttgaa tcttcgaatc aagtctgtag agc 33

<210> SEQ ID NO 5
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
cttctccctc attctggagt tggcta 26

<210> SEQ ID NO 6
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ctctgaaatg aacatgagtg ccttgg 26

<210> SEQ ID NO 7
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tttctctctc attctggagt tggctt 26

<210> SEQ ID NO 8
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gtgcatcctg gaaatcctat cctctg 26

<210> SEQ ID NO 9
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ctgcagcttg gaaatcagtt cctctg 26

<210> SEQ ID NO 10
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gctactttta catgtatctg ccgtgg 26

<210> SEQ ID NO 11
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11

-continued ctgcatcctg gaaatcctat cctcug 26

<210> SEQ ID NO 12
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
ctccactctg aagattcaac ctacag 26

<210> SEQ ID NO 13
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 13
ctcaactctg aagatccaga gcacgc 26

<210> SEQ ID NO 14
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 14
cttcaccttc actgtggaat tggcct 26

<210> SEQ ID NO 15
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 15
tttctccctg attctggatt ctgcta 26

<210> SEQ ID NO 16
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
cttcatcttg gaaatgcagt cctcag 26

<210> SEQ ID NO 17
<211> LENGTH: 26
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 17
ctctgagatt aacctgagtg ccttgg 26

<210> SEQ ID NO 18
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ttgcagccta gaaattcagt cctctg 26

<210> SEQ ID NO 19
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gctactttta catatatctg ccgtgg 26

<210> SEQ ID NO 20
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ctgctctctc tacattggct ctgcag 26

<210> SEQ ID NO 21
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cttcttcctc ctgctggaat tggctt 26

<210> SEQ ID NO 22
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ctccactctc aagatccagt ctgcaa 26

<210> SEQ ID NO 23

-continued

<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
attctccctc attctggagt tggcta 26

<210> SEQ ID NO 24
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
ctcaacgttg acagtgaaca atgcaa 26

<210> SEQ ID NO 25
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
tttagacctt cagatcacag ctctaa 26

<210> SEQ ID NO 26
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
atgtaccata gagatccagt ccagca 26

<210> SEQ ID NO 27
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27
ctctgagatg aacatgagtg ccttgg 26

<210> SEQ ID NO 28
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 28
tttcactctg aaaatccaac ccacag 26

<210> SEQ ID NO 29
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 29
attcatccta agcacggaga agctgc 26

<210> SEQ ID NO 30
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 30
ctccatgttg aagagccaat caacac 26

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 31
actgtgacat ctgcccagaa g 21

<210> SEQ ID NO 32
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 32
ctgcaagtgg ccaacatgag c 21

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 33
ggaatcagaa cgtgcgaagc a 21

<210> SEQ ID NO 34
<211> LENGTH: 30
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 34 cctttcatc taugacagtt ttaaatgcau 30

<210> SEQ ID NO 35
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 35
gaacccaaca ucctaaagug gggccagcag auc 33

<210> SEQ ID NO 36
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 36
agagcttucc cctgacauta gagtcaacca gtu 33

<210> SEQ ID NO 37
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 37
ctcatttgaa tctucgaatc aagtctguag agc 33

<210> SEQ ID NO 38
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 38
cttctccctc atuctggagt tggcua 26

<210> SEQ ID NO 39
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 39
ctctgaaatg aacaugagtg cctugg 26

<210> SEQ ID NO 40
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 40
tttctctctc atuctggagt tggctu 26

<210> SEQ ID NO 41
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 41
gtgcatcctg gaaaucctat cctcug 26

<210> SEQ ID NO 42
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 42
ctgcagcttg gaaaucagtt cctcug 26

<210> SEQ ID NO 43

<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 43
gctactttta caugtatctg ccgugg 26

<210> SEQ ID NO 44
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 44
ctgcatcctg gaaaucctat cctcug 26

<210> SEQ ID NO 45
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 45
ctccactcug aagattcaac cuacag 26

<210> SEQ ID NO 46
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 46
cucaactctg aagauccaga gcacgc 26

<210> SEQ ID NO 47
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Description of Combined DNA/RNA
      Molecule: Synthetic oligonucleotide"

<400> SEQUENCE: 47
cttcaccttc acugtggaat tggccu 26

<210> SEQ ID NO 48
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 48
tttctccctg atuctggatt ctgcua 26

<210> SEQ ID NO 49
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 49
cttcatcttg gaaaugcagt ccucag 26

<210> SEQ ID NO 50
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 50
ctctgagatu aacctgagtg cctugg 26

<210> SEQ ID NO 51
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 51
ttgcagccta gaaautcagt cctcug 26

<210> SEQ ID NO 52
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 52
gctactttta cauatatctg ccgugg 26

<210> SEQ ID NO 53
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 53
ctgctctctc uacattggct cugcag 26

<210> SEQ ID NO 54
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 54
cttcttcctc cugctggaat tggctu 26

<210> SEQ ID NO 55
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 55
ctccactcuc aagatccagt cugcaa 26

<210> SEQ ID NO 56
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 56
attctccctc atuctggagt tggcua 26

<210> SEQ ID NO 57
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 57
ctcaacgtug acagtgaaca augcaa 26

<210> SEQ ID NO 58
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 58
tttagacctt cagaucacag ctcuaa 26

<210> SEQ ID NO 59
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 59
atgtaccaua gagatccagu ccagca 26

<210> SEQ ID NO 60
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA -continued Molecule: Synthetic oligonucleotide"

<400> SEQUENCE: 60
ctctgagatg aacaugagtg cctugg 26

<210> SEQ ID NO 61
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 61
uttcactctg aaaauccaac ccacag 26

<210> SEQ ID NO 62
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 62
attcatccua agcacggaga agcugc 26

<210> SEQ ID NO 63
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 63
ctccatgtug aagagccaau caacac 26

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 64
acugtgacat cugcccagaa g 21

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 65
ctgcaagugg ccaacaugag c 21

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 66
ggaaucagaa cgugcgaagc a 21

<210> SEQ ID NO 67
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 67
cttataccta agttcctttc caagacc 27

<210> SEQ ID NO 68
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 68
cgaggagccg agtgcctg 18

<210> SEQ ID NO 69
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 69
cagtgagccg ggtgcctg 18

<210> SEQ ID NO 70
<211> LENGTH: 22
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic oligonucleotide"

<400> SEQUENCE: 70
tacaactgtg agtgtggttc ct 22

<210> SEQ ID NO 71
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ctacaactgt gagtctggtt cct 23

<210> SEQ ID NO 72
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ctaggacggt gagtcgtgtc cc 22

<210> SEQ ID NO 73
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
ccaagacaga cagcttggtt cc 22

<210> SEQ ID NO 74
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
ctacaacaat gagccggctt cc 22

<210> SEQ ID NO 75
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
ctattaccaa aagcctggtc cc 22

<210> SEQ ID NO 76
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 76
ctaaaaccgt gagcctggtg cc 22

<210> SEQ ID NO 77
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 77
ccagcactgt cagctttgag cc 22

<210> SEQ ID NO 78
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 78
ataggctgtt caatcggctg cc 22

<210> SEQ ID NO 79
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 79
cgagaacagt cagtctggtt cc 22

<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 80
taaaaccgtg agcctagtgc c 21

<210> SEQ ID NO 81
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 81
ctagcaccga tagtcgggtg cc 22

<210> SEQ ID NO 82
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 82
ccaggacaga cagcttggtt cc 22

<210> SEQ ID NO 83
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
ctagaacaga gagtcgagtc cc 22

<210> SEQ ID NO 84
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 84
cttataccua agttccttuc caagacc 27

<210> SEQ ID NO 85
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
cgaggagccg agugccug 18

<210> SEQ ID NO 86
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 86
cagtgagccg ggugccug 18

<210> SEQ ID NO 87
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 87
tacaactgtg agugtggttc cu 22

<210> SEQ ID NO 88
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 88
ctacaactgu gagtctggtt ccu 23

<210> SEQ ID NO 89
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 89
ctaggacggu gagtcgtguc cc 22

<210> SEQ ID NO 90
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 90
ccaagacaga cagcutggtu cc 22

<210> SEQ ID NO 91
<211> LENGTH: 22
<212> TYPE: DNA

-continued

<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 91
ctacaacaau gagccggctu cc 22

<210> SEQ ID NO 92
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 92
ctatuaccaa aagcctgguc cc 22

<210> SEQ ID NO 93
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 93
ctaaaaccgu gagcctggug cc 22

<210> SEQ ID NO 94
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 94
ccagcacugt cagcttugag cc 22

<210> SEQ ID NO 95
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 95
ataggctgtu caatcggcug cc 22

<210> SEQ ID NO 96
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 96
cgagaacagu cagtctggtu cc 22

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 97
taaaaccgug agcctagugc c 21

<210> SEQ ID NO 98
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 98
ctagcaccga uagtcgggug cc 22

<210> SEQ ID NO 99
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 99
ccaggacaga cagcutggtu cc 22

<210> SEQ ID NO 100
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 100
ctagaacaga gagucgaguc cc 22

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
gcagctcaga agcctgacat 20

<210> SEQ ID NO 102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
ggagctcagc agcctgacat 20

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
gcagctcagc agcctgactt 20

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
ggagctccgc agcctgacat 20

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
gcaactcagc agcctgacaa 20

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
gcagctcagc agcctgacct 20

<210> SEQ ID NO 107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 107
gcaactcagc agcccgacat 20

<210> SEQ ID NO 108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 108
ggagctccac agcctgacat 20

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 109
gcagttcaac agcctgacat 20

<210> SEQ ID NO 110
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 110
tcagctcagc agcctggcat 20

<210> SEQ ID NO 111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 111
ggagcttagt agattgacat 20

<210> SEQ ID NO 112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 112
gcagctcagc agcctgacat 20

<210> SEQ ID NO 113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 113
gttgctcagc agcctgacct 20

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 114
ggatctcagc agcctgacct 20

<210> SEQ ID NO 115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 115
ggagctccgg agcctggcat 20

<210> SEQ ID NO 116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 116
ggatctcagc agcccgacat 20

<210> SEQ ID NO 117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
ggagctcaac agtctgacat 20

<210> SEQ ID NO 118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 118
gcagctcaag agcctgacat 20

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 119
ggagctcagc cgattaacat 20

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 120
gcaactcagc agcctgacat 20

<210> SEQ ID NO 121
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
ggaacttgcc agattgacat 20

<210> SEQ ID NO 122
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122
ggagctcagc agcctgacaa 20

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123
ggacgtccgc agcctgacat 20

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 124
ggagctcctg agcctgacat 20

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125
gcacctcagc agcctgacat 20

<210> SEQ ID NO 126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 126
ggagctcaac agcctgacat 20

<210> SEQ ID NO 127
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 127
gcaactgagc agcctgacat 20

<210> SEQ ID NO 128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 128
ggagctaaac agcctgactt 20

<210> SEQ ID NO 129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 129
ggaactcagc agcctcacat 20

<210> SEQ ID NO 130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 130
gcaactcagc agcttgacat 20

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 131
ggatctcagc agcctgacat 20

<210> SEQ ID NO 132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 132
ggagctcagc agcctgacct 20

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 133
gcagttcagc agcctgacat 20

<210> SEQ ID NO 134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 134
gcagctcaac agcctgacat 20

<210> SEQ ID NO 135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135
gcatctcaac agcctgacat 20

<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
gcagtccagc agcctgacat 20

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 137
gcagctgagc agcctgacat 20

<210> SEQ ID NO 138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138
gcagctcagc agcctaacat 20

<210> SEQ ID NO 139
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 139
ggagctccgg agcctgacat 20

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
ggtgttgaac agcctgacat 20

<210> SEQ ID NO 141
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 141
tgtacctgca aatgagcagt ctgagtt 27

<210> SEQ ID NO 142
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 142
tgtacctgga aatgagcagt ctgaggt 27

<210> SEQ ID NO 143
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 143
tgtacctgca aatgagccat ctgaagt 27

<210> SEQ ID NO 144
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 144
tatacctgca aatgagcagt ctgaagt 27

<210> SEQ ID NO 145
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145
tttacctgca aatgaccagt ctgaagt 27

<210> SEQ ID NO 146
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 146
tgtacctgca aatgagccgt ctgaagt 27

<210> SEQ ID NO 147
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 147
tgtacctgca aatgagcagt ctgaagt 27

<210> SEQ ID NO 148
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 148
tgttcctgca aatgaccagt ctaaggt 27

<210> SEQ ID NO 149
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 149
tgtacctgca aatgagcagt ctgaggt 27

<210> SEQ ID NO 150
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 150
tgttcctgca aatgaccagt ctgaggt 27

<210> SEQ ID NO 151
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 151
cttaaaaatg aacagtctcc aaa 23

<210> SEQ ID NO 152
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 152
cttaaaactg aacagtctgc aaa 23

<210> SEQ ID NO 153
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 153
cttaaaaatg aacagtctgc aaa 23

<210> SEQ ID NO 154
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 154
ctttaaaatg aacagtctgc aag 23

<210> SEQ ID NO 155
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 155
ctttaaaatg aacagtctgc aat 23

<210> SEQ ID NO 156

-continued

<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
atgctctatc tgcaaatgaa caacctgaaa a 31

<210> SEQ ID NO 157
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
atgctctatc tgcaaatgaa caacttgaaa a 31

<210> SEQ ID NO 158
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
gtctacctgc aaatgaacaa cttaaggg 28

<210> SEQ ID NO 159
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 159
gtctacctgc agatggacag attaagag 28

<210> SEQ ID NO 160
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
gtctacctgc aaaagaacag cttaagag 28

<210> SEQ ID NO 161
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
gtctacctgc aaatgaacag cttaagag 28

<210> SEQ ID NO 162
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
gtctacctgc atatgaacag cttaagag 28

<210> SEQ ID NO 163
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
gtatacctgc aaatgaacaa cttaagag 28

<210> SEQ ID NO 164
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
gtctacctgc aaatgaacaa cttaagag 28

<210> SEQ ID NO 165
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 165
gtctacctag agatgaacag attaagag 28

<210> SEQ ID NO 166
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
gtctacctgc agatgaacag attaagag 28

<210> SEQ ID NO 167
<211> LENGTH: 29
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 167
gctgtacctg caaatgagca aagtgagat 29

<210> SEQ ID NO 168
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 168
agttttcttt aaaatgagca gtctgcaaa 29

<210> SEQ ID NO 169
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 169
cctgtacctg cagatgagca atgtgcgat 29

<210> SEQ ID NO 170
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
gttcttcctc caattgaact ctgtgacca 29

<210> SEQ ID NO 171
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
gttctttctg caattgaact ctgtgacca 29

<210> SEQ ID NO 172
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
attctttatc cagctgagct ctgtgacaa 29

<210> SEQ ID NO 173
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 173
ttcctgcagt tgaattctgt gactac 26

<210> SEQ ID NO 174
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 174
ttcctgaagt tgaattctgt gactac 26

<210> SEQ ID NO 175
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 175
ttcctgcagt tgaactctgt gactat 26

<210> SEQ ID NO 176
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 176
tcactgaagt tgagttctgt gactac 26

<210> SEQ ID NO 177
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 177
ttcctgcagt tgaactctgt gactac 26

<210> SEQ ID NO 178
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 178
ttcctggaaa tgaactcttt gactgc 26

<210> SEQ ID NO 179
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
ttcttgaagt tgaattctgt gactac 26

<210> SEQ ID NO 180
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
tacctgcagt tgaattctgt gactac 26

<210> SEQ ID NO 181
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
tacctacagt tgaattctgt gactac 26

<210> SEQ ID NO 182
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
tacctgcagt tgaattctgt gacttc 26

<210> SEQ ID NO 183
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
tcctctatct tcaaatgaac accctgagag 30

<210> SEQ ID NO 184
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 184
tcctctacct tcagatgaat gccctgagag 30

<210> SEQ ID NO 185
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 185
tcctctatct tcaaatgaac accctgaggg 30

<210> SEQ ID NO 186
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 186
tcctctatct tcaaatgaat gccctgagag 30

<210> SEQ ID NO 187
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 187
ttgcagatca acaacctcaa aaa 23

<210> SEQ ID NO 188
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 188
ttacagataa gcaacctcaa aaa 23

<210> SEQ ID NO 189
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 189
ggtattcctc aagatcacca ctgtggaca 29

<210> SEQ ID NO 190
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 190
ggtattcctc aagatcgcca gtgtggaca 29

<210> SEQ ID NO 191
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 191
ggtattcctc aagatcgcca atgtggaca 29

<210> SEQ ID NO 192
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 192
ggtattcctc aagatcacca gtgtggaca 29

<210> SEQ ID NO 193
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 193
gctcaagagc ctgacatctg a 21

<210> SEQ ID NO 194
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 194
tctcaacagc ctgacatctg a 21

<210> SEQ ID NO 195
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195
gcttagtaga ttgacatctg a 21

<210> SEQ ID NO 196
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
acttgccaga ttgacatctg a 21

<210> SEQ ID NO 197
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
gctcagcagc ctgacaaatg a 21

<210> SEQ ID NO 198
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
gttcagcagc ctgacatctg a 21

<210> SEQ ID NO 199
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 199
gctcagccga ttaacatctg a 21

<210> SEQ ID NO 200
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 200
gctcaacagc ctgacatctg a 21

<210> SEQ ID NO 201
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 201
gctcagcagc ctgacatctg a 21

<210> SEQ ID NO 202
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 202
actcagcagc ctcacatctg a 21

<210> SEQ ID NO 203
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 203
tctcagcagc ctgacctctg a 21

<210> SEQ ID NO 204
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204
gctccggagc ctgacatctg a 21

<210> SEQ ID NO 205
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 205
gctccgcagc ctgacatcgg a 21

<210> SEQ ID NO 206
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
actgagcagc ctgacatctg a 21

<210> SEQ ID NO 207
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 207
gctcagcagc ctaacatctg a 21

<210> SEQ ID NO 208
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 208
tctcagcagc ctgacatctg a 21

<210> SEQ ID NO 209
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 209
actcagcagc ccgacatctg a 21

<210> SEQ ID NO 210
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 210
gctcagcagc ctgacttctg a 21

<210> SEQ ID NO 211
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 211
gctcctgagc ctgacatctg a 21

<210> SEQ ID NO 212
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 212
actcagcagc ttgacatctg a 21

<210> SEQ ID NO 213
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 213
gtccagcagc ctgacatctg a 21

<210> SEQ ID NO 214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 214
gctgagcagc ctgacatatg a 21

<210> SEQ ID NO 215
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 215
gctccacagc ctgacatctg a 21

<210> SEQ ID NO 216
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 216
gctcaacagt ctgacatccg a 21

<210> SEQ ID NO 217
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 217
cctcagcagc ctgacatctg a 21

<210> SEQ ID NO 218
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218

gctccgcagc ctgacatctg a                                              21


<210> SEQ ID NO 219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219

tctcagcagc ccgacatctg a                                              21


<210> SEQ ID NO 220
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220

gctcagcagc ctggcatctg a                                              21


<210> SEQ ID NO 221
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221

actcagcagc ctgacatctg a                                              21


<210> SEQ ID NO 222
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222

gctcagaagc ctgacatctg a                                              21


<210> SEQ ID NO 223
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
```

tctcagcagc ctgacatcta a 21

<210> SEQ ID NO 224
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224
gctccggagc ctggcatctg a 21

<210> SEQ ID NO 225
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
gttgaacagc ctgacatctg a 21

<210> SEQ ID NO 226
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226
actcagcagc ctgacaactg a 21

<210> SEQ ID NO 227
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227
gctaaacagc ctgacttctg a 21

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 228
cgtccgcagc ctgacatctg a 21

<210> SEQ ID NO 229
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 229
gctcaacagt ctgacatctg a 21

<210> SEQ ID NO 230
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 230
gctcagcagc ctgacctctg a 21

<210> SEQ ID NO 231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 231
gttcaacagc ctgacatctg a 21

<210> SEQ ID NO 232
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 232
aatgaccagt ctgaggtctg ag 22

<210> SEQ ID NO 233
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 233
aatgagcagt ctgaagtctg ag 22

<210> SEQ ID NO 234
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 234
aatgaccagt ctaaggtctg ag 22

<210> SEQ ID NO 235

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 235
aatgagccat ctgaagtctg ag 22

<210> SEQ ID NO 236
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 236
aatgagccgt ctgaagtctg ag 22

<210> SEQ ID NO 237
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 237
aatgagcagt ctgagttcta ag 22

<210> SEQ ID NO 238
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 238
aatgagcagt ctgaggtctg ag 22

<210> SEQ ID NO 239
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 239
aatgaccagt ctgaagtcag ag 22

<210> SEQ ID NO 240
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 240

-continued taaaaatgaa cagtctccaa actgat 26

<210> SEQ ID NO 241
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 241
ttaaaatgaa cagtctgcaa gctaat 26

<210> SEQ ID NO 242
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 242
ttaaaatgaa cagtctgcaa tctaat 26

<210> SEQ ID NO 243
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 243
ttaaaatgaa cagtctgcaa gctgat 26

<210> SEQ ID NO 244
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 244
taaaactgaa cagtctgcaa actgat 26

<210> SEQ ID NO 245
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 245
taaaaatgaa cagtctgcaa actgat 26

<210> SEQ ID NO 246
<211> LENGTH: 32
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 246
tctatctgca aatgaacaac ttgaaaactg ag 32

<210> SEQ ID NO 247
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 247
tctatctgca aatgaacaac ctgaaaactg ag 32

<210> SEQ ID NO 248
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 248
ctgcaaatga acaacttaag agctgaa 27

<210> SEQ ID NO 249
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 249
ctgcaaaaga acagcttaag agctgaa 27

<210> SEQ ID NO 250
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 250
ctgcagatga acagattaag agaggaa 27

<210> SEQ ID NO 251
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 251
ctagagatga acagattaag agaggaa 27

<210> SEQ ID NO 252
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
ctgcagatgg acagattaag agaggaa 27

<210> SEQ ID NO 253
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
ctgcaaatga acagcttaag agctgaa 27

<210> SEQ ID NO 254
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
ctgcaaatga acaacttaag ggctgaa 27

<210> SEQ ID NO 255
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
ctgcatatga acagcttaag agccgaa 27

<210> SEQ ID NO 256
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
cctgcagatg agcaatgtgc gatctgag 28

<210> SEQ ID NO 257
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
cctgcagatg agcaatgtgc gatcggag 28

<210> SEQ ID NO 258
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
tatccagctg agctctgtga caaatgag 28

<210> SEQ ID NO 259
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
cctccaattg aactctgtga ccacagag 28

<210> SEQ ID NO 260
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
tctgcaattg aactctgtga ccacagag 28

<210> SEQ ID NO 261
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
ctttaaaatg agcagtctgc aaagtgaa 28

<210> SEQ ID NO 262
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
cctgcaaatg agcaaagtga gatctgag 28

<210> SEQ ID NO 263
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 263
agttgagttc tgtgactact gagg 24

<210> SEQ ID NO 264
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 264
aaatgaactc tttgactgct gagg 24

<210> SEQ ID NO 265
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 265
agttgaattc tgtgacttct gagg 24

<210> SEQ ID NO 266
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 266
aaatgaactc tttgactgct gaag 24

<210> SEQ ID NO 267
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 267
agttgaactc tgtgactact gaag 24

<210> SEQ ID NO 268
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 268
agttgaattc tgtgactact gagg 24

<210> SEQ ID NO 269
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 269
agttgaactc tgtgactatt gaag 24

<210> SEQ ID NO 270
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 270
cttcaaatga acaccctgag ggctgag 27

<210> SEQ ID NO 271
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 271
cttcagatga atgccctgag agctgag 27

<210> SEQ ID NO 272
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 272
cttcaaatga atgccctgag agctgag 27

<210> SEQ ID NO 273
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 273
cttcaaatga acaccctgag agctgag 27

<210> SEQ ID NO 274
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 274
cagatcaaca acctcaaaaa tcag 24

<210> SEQ ID NO 275
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 275
cagataagca acctcaaaaa tgag 24

<210> SEQ ID NO 276
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 276
cagatcaaca acctcaaaaa tgag 24

<210> SEQ ID NO 277
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
tattcctcaa gatcaccagt gtggacactg ca 32

<210> SEQ ID NO 278
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 278
tattcctcaa gatcgccagt gtggacactg ca 32

<210> SEQ ID NO 279
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
tattcctcaa gatcgccaat gtggacactg ca 32

<210> SEQ ID NO 280
<211> LENGTH: 32
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
tattcctcaa gatcaccact gtggacactg ca 32

<210> SEQ ID NO 281
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
tattcctcaa gatcaccact gtggacactg ta 32

<210> SEQ ID NO 282
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
cagcagcctg acatctgagg ac 22

<210> SEQ ID NO 283
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
caacagtctg acatctgagg ac 22

<210> SEQ ID NO 284
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
tgccagattg acatctgagg at 22

<210> SEQ ID NO 285
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
cagcagcctg acatctaagg ac 22

<210> SEQ ID NO 286
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 286
cagaagcctg acatctgag 19

<210> SEQ ID NO 287
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
caacagcctg acatctgagg at 22

<210> SEQ ID NO 288
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
cagcagcctc acatctgagg ac 22

<210> SEQ ID NO 289
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
gagcagcctg acatatgagg ac 22

<210> SEQ ID NO 290
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
cagcagcttg acatctgagg ac 22

<210> SEQ ID NO 291
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 291
cagccgatta acatctgatg ac 22

<210> SEQ ID NO 292
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292
cagcagcctg acaaatgagg ac 22

<210> SEQ ID NO 293
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 293
cagcagcctg acaactgagg ac 22

<210> SEQ ID NO 294
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 294
tagtagattg acatctgaag ac 22

<210> SEQ ID NO 295
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 295
cagcagcccg acatctgagg ac 22

<210> SEQ ID NO 296
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 296
cagcagcctg acatctgaag ac 22

<210> SEQ ID NO 297
<211> LENGTH: 22

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 297
aaacagcctg acttctgagg ac 22

<210> SEQ ID NO 298
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
gagcagcctg acatctgagg ac 22

<210> SEQ ID NO 299
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 299
cagaagcctg acatctgagg ac 22

<210> SEQ ID NO 300
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
ccacagcctg acatctgagg ac 22

<210> SEQ ID NO 301
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
ccgcagcctg acatctgagg ac 22

<210> SEQ ID NO 302
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
cagcagcctg acatctgatg ac 22

<210> SEQ ID NO 303
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 303
caagagcctg acatctgagg ac 22

<210> SEQ ID NO 304
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 304
cagcagcctg acctctgagg ac 22

<210> SEQ ID NO 305
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 305
ccggagcctg gcatctgagg ac 22

<210> SEQ ID NO 306
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 306
caacagcctg acatctgagg ac 22

<210> SEQ ID NO 307
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 307
caacagcctg acatctgaag ac 22

<210> SEQ ID NO 308
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 308
cctgagcctg acatctgagg ac 22

<210> SEQ ID NO 309
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 309
cagcagccta acatctgagg ac 22

<210> SEQ ID NO 310
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 310
cagcagcctg gcatctgagg ac 22

<210> SEQ ID NO 311
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 311
gaacagcctg acatctgagg ac 22

<210> SEQ ID NO 312
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 312
cagcagcctg acttctgaga ac 22

<210> SEQ ID NO 313
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 313
caacagtctg acatccgagg ac 22

<210> SEQ ID NO 314

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 314
ccggagcctg acatctgagg ac 22

<210> SEQ ID NO 315
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 315
ccgcagcctg acatcggagg at 22

<210> SEQ ID NO 316
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 316
cagcagcctg acatctgacg ac 22

<210> SEQ ID NO 317
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 317
gaccagtctg aggtctgagg ac 22

<210> SEQ ID NO 318
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
gagcagtctg agttctaagg ac 22

<210> SEQ ID NO 319
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
gagccatctg aagtctgagg ac 22

<210> SEQ ID NO 320
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 320
gaccagtcta aggtctgagg ac 22

<210> SEQ ID NO 321
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 321
gagcagtctg aagtctgagg ac 22

<210> SEQ ID NO 322
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 322
gagccgtctg aagtctgagg ac 22

<210> SEQ ID NO 323
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 323
gagcagtctg aggtctgagg ac 22

<210> SEQ ID NO 324
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 324
gaccagtctg aagtcagagg ac 22

<210> SEQ ID NO 325
<211> LENGTH: 26
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 325

aaatgaacag tctgcaagct aatgac                                      26


<210> SEQ ID NO 326
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326

aaatgaacag tctccaaact gatgac                                      26


<210> SEQ ID NO 327
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327

aaatgaacag tctgcaagct gatgac                                      26


<210> SEQ ID NO 328
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328

aaatgaacag tctgcaaact gatgac                                      26


<210> SEQ ID NO 329
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329

aaatgaacag tctgcaatct aatgac                                      26


<210> SEQ ID NO 330
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330

aactgaacag tctgcaaact gatgac                                      26
```

<210> SEQ ID NO 331
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 331
ctgcaaatga acaacttgaa aactgaggac 30

<210> SEQ ID NO 332
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 332
ctgcaaatga acaacctgaa aactgaggac 30

<210> SEQ ID NO 333
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 333
caaatgaaca gcttaagagc tgaagac 27

<210> SEQ ID NO 334
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 334
catatgaaca gcttaagagc cgaagat 27

<210> SEQ ID NO 335
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 335
caaaagaaca gcttaagagc tgaagat 27

<210> SEQ ID NO 336
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 336
caaatgaaca acttaagagc tgaagac 27

<210> SEQ ID NO 337
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 337
cagatgaaca gattaagaga ggaagac 27

<210> SEQ ID NO 338
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 338
gagatgaaca gattaagaga ggaagac 27

<210> SEQ ID NO 339
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 339
caaatgaaca acttaagggc tgaagac 27

<210> SEQ ID NO 340
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 340
cagatggaca gattaagaga ggaagac 27

<210> SEQ ID NO 341
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 341
ccagctgagc tctgtgacaa atgaggac 28

<210> SEQ ID NO 342
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 342
gcaaatgagc aaagtgagat ctgaggac 28

<210> SEQ ID NO 343
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 343
ccaattgaac tctgtgacca cagaggac 28

<210> SEQ ID NO 344
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 344
taaaatgagc agtctgcaaa gtgaagac 28

<210> SEQ ID NO 345
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 345
gcagatgagc aatgtgcgat cggaggac 28

<210> SEQ ID NO 346
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 346
gcaattgaac tctgtgacca cagaggac 28

<210> SEQ ID NO 347
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 347
gcagatgagc aatgtgcgat ctgaggac 28

<210> SEQ ID NO 348
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 348
ttgaactctg tgactactga aga 23

<210> SEQ ID NO 349
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 349
atgaactctt tgactgctga gga 23

<210> SEQ ID NO 350
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 350
ttgaattctg tgacttctga gga 23

<210> SEQ ID NO 351
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 351
ttgagttctg tgactactga gga 23

<210> SEQ ID NO 352
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 352
ttgaactctg tgactattga aga 23

<210> SEQ ID NO 353
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 353
ttgaattctg tgactactga gga 23

<210> SEQ ID NO 354
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 354
atgaactctt tgactgctga aga 23

<210> SEQ ID NO 355
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 355
cagatgaatg ccctgagagc tgaggac 27

<210> SEQ ID NO 356
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 356
caaatgaaca ccctgagagc tgaggac 27

<210> SEQ ID NO 357
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 357
caaatgaatg ccctgagagc tgaggac 27

<210> SEQ ID NO 358
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 358
caaatgaaca ccctgagggc tgaggac 27

<210> SEQ ID NO 359
<211> LENGTH: 27
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 359
caaatgaaca ccctgagagc tgaggcc 27

<210> SEQ ID NO 360
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 360
caacaacctc aaaaatcagg ac 22

<210> SEQ ID NO 361
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 361
aagcaacctc aaaaatgagg ac 22

<210> SEQ ID NO 362
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 362
caacaacctc aaaaatgagg ac 22

<210> SEQ ID NO 363
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 363
aagatcgcca atgtggacac tgcagat 27

<210> SEQ ID NO 364
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 364
aagatcacca ctgtggacac tgcagat 27

<210> SEQ ID NO 365
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 365
aagatcacca gtgtggacac tgcagat 27

<210> SEQ ID NO 366
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
aagatcgcca gtgtggacac tgcagat 27

<210> SEQ ID NO 367
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 367
aagatcacca ctgtggacac tgtagat 27

<210> SEQ ID NO 368
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 368
agcagcccga catctgagga ct 22

<210> SEQ ID NO 369
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 369
agcagcctga catctgatga ct 22

<210> SEQ ID NO 370
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 370
gccagattga catctgagga tt 22

<210> SEQ ID NO 371
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 371
cggagcctgg catctgagga ct 22

<210> SEQ ID NO 372
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
aacagcctga cttctgagga ct 22

<210> SEQ ID NO 373
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
agaagcctga catctgagga ct 22

<210> SEQ ID NO 374
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374
aacagcctga catctgagga tt 22

<210> SEQ ID NO 375
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 375
agcagcctga catctgagga ca 22

<210> SEQ ID NO 376
<211> LENGTH: 18

-continued

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 376
agaagcctga catctgag 18

<210> SEQ ID NO 377
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 377
aacagcctga catctgagga cc 22

<210> SEQ ID NO 378
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 378
agccgattaa catctgatga ct 22

<210> SEQ ID NO 379
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 379
agcagcctga cttctgagaa ct 22

<210> SEQ ID NO 380
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 380
agcagcctga cctctgagga ct 22

<210> SEQ ID NO 381
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
ctgagcctga catctgagga ct 22

<210> SEQ ID NO 382
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 382
aacagcctga catctgagga ct 22

<210> SEQ ID NO 383
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 383
aacagcctga catctgaaga ct 22

<210> SEQ ID NO 384
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 384
agcagcctga catctgaaga ct 22

<210> SEQ ID NO 385
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 385
agcagcttga catctgagga ct 22

<210> SEQ ID NO 386
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 386
agcagcctga catctgagga ct 22

<210> SEQ ID NO 387
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 387
aagagcctga catctgagga ct 22

<210> SEQ ID NO 388
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 388
agcagcctga caactgagga ct 22

<210> SEQ ID NO 389
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 389
cgcagcctga catctgagga ct 22

<210> SEQ ID NO 390
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 390
agcagcctgg catctgagga ct 22

<210> SEQ ID NO 391
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 391
agcagcctga catctaagga ct 22

<210> SEQ ID NO 392
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
agtagattga catctgaaga ct 22

<210> SEQ ID NO 393

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
cggagcctga catctgagga ct 22

<210> SEQ ID NO 394
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
agcagcctga catctgacga ct 22

<210> SEQ ID NO 395
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
cacagcctga catctgagga ct 22

<210> SEQ ID NO 396
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
agcagcctaa catctgagga ct 22

<210> SEQ ID NO 397
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
aacagtctga catccgagga ct 22

<210> SEQ ID NO 398
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 398
aacagtctga catctgagga ct 22

<210> SEQ ID NO 399
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 399
agcagcctga caaatgagga ct 22

<210> SEQ ID NO 400
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 400
agcagcctga catatgagga ct 22

<210> SEQ ID NO 401
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 401
cgcagcctga catctgagga ca 22

<210> SEQ ID NO 402
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 402
agcagcctca catctgagga ct 22

<210> SEQ ID NO 403
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 403
cgcagcctga catcggagga tt 22

<210> SEQ ID NO 404
<211> LENGTH: 23
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 404
gagcagtctg aggtctgagg aca 23

<210> SEQ ID NO 405
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 405
gaccagtcta aggtctgagg aca 23

<210> SEQ ID NO 406
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 406
gagcagtctg agttctaagg aca 23

<210> SEQ ID NO 407
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 407
gaccagtctg aggtctgagg aca 23

<210> SEQ ID NO 408
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 408
gagccgtctg aagtctgagg aca 23

<210> SEQ ID NO 409
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 409
gaccagtctg aagtcagagg aca 23

-continued

<210> SEQ ID NO 410
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 410
gagccatctg aagtctgagg aca 23

<210> SEQ ID NO 411
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 411
gagcagtctg aagtctgagg aca 23

<210> SEQ ID NO 412
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 412
aaatgaacag tctgcaatct aatgaca 27

<210> SEQ ID NO 413
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 413
aactgaacag tctgcaaact gatgaca 27

<210> SEQ ID NO 414
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 414
aaatgaacag tctgcaagct aatgaca 27

<210> SEQ ID NO 415
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 415
aaatgaacag tctgcaagct gatgaca 27

<210> SEQ ID NO 416
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 416
aaatgaacag tctgcaaact gatgaca 27

<210> SEQ ID NO 417
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 417
aaatgaacag tctccaaact gatgaca 27

<210> SEQ ID NO 418
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 418
caaatgaaca acctgaaaac tgaggaca 28

<210> SEQ ID NO 419
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 419
caaatgaaca acttgaaaac tgaggaca 28

<210> SEQ ID NO 420
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 420
atgaacaact taagagctga agaca 25

<210> SEQ ID NO 421
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
atgaacaact taagggctga agaca 25

<210> SEQ ID NO 422
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 422
atgaacagct taagagctga agaca 25

<210> SEQ ID NO 423
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 423
atggacagat taagagagga agaca 25

<210> SEQ ID NO 424
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 424
aagaacagct taagagctga agata 25

<210> SEQ ID NO 425
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 425
atgaacagat taagagagga agaca 25

<210> SEQ ID NO 426
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 426
atgaacagct taagagccga agata 25

```
<210> SEQ ID NO 427
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427

caaatgagca aagtgagatc tgaggaca                                    28


<210> SEQ ID NO 428
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428

cagatgagca atgtgcgatc tgaggaca                                    28


<210> SEQ ID NO 429
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429

cagatgagca atgtgcgatc tgaggacc                                    28


<210> SEQ ID NO 430
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430

caattgaact ctgtgaccac agaggaca                                    28


<210> SEQ ID NO 431
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431

cagatgagca atgtgcgatc ggaggaca                                    28


<210> SEQ ID NO 432
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 432
aaaatgagca gtctgcaaag tgaagaca 28

<210> SEQ ID NO 433
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
cagctgagct ctgtgacaaa tgaggaca 28

<210> SEQ ID NO 434
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
gaactctgtg actactgaag ata 23

<210> SEQ ID NO 435
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
gaattctgtg acttctgagg aca 23

<210> SEQ ID NO 436
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 436
gaactctgtg actattgaag ata 23

<210> SEQ ID NO 437
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
gaattctgtg actactgagg acg 23

<210> SEQ ID NO 438
<211> LENGTH: 23
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
gaactctttg actgctgagg aca 23

<210> SEQ ID NO 439
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
gaattctgtg actactgagg aca 23

<210> SEQ ID NO 440
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
gaactctttg actgctgaag aca 23

<210> SEQ ID NO 441
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
gagttctgtg actactgagg aca 23

<210> SEQ ID NO 442
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
tcaaatgaat gccctgagag ctgaggaca 29

<210> SEQ ID NO 443
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
tcaaatgaac accctgagag ctgaggaca 29

<210> SEQ ID NO 444
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 444
tcaaatgaac accctgaggg ctgaggaca 29

<210> SEQ ID NO 445
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
tcaaatgaac accctgagag ctgaggcca 29

<210> SEQ ID NO 446
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 446
tcagatgaat gccctgagag ctgaggaca 29

<210> SEQ ID NO 447
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 447
aacctcaaaa atgaggaca 19

<210> SEQ ID NO 448
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 448
aacctcaaaa atcaggaca 19

<210> SEQ ID NO 449
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 449
aagatcgcca atgtggacac tgcagata 28

<210> SEQ ID NO 450
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 450
aagatcgcca gtgtggacac tgcagata 28

<210> SEQ ID NO 451
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 451
aagatcacca ctgtggacac tgcagata 28

<210> SEQ ID NO 452
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 452
aagatcacca gtgtggacac tgcagata 28

<210> SEQ ID NO 453
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 453
aagatcacca ctgtggacac tgtagata 28

<210> SEQ ID NO 454
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 454
cgcagcctga catctgagga ctc 23

<210> SEQ ID NO 455
<211> LENGTH: 23

-continued

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 455
cacagcctga catctgagga ctc 23

<210> SEQ ID NO 456
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 456
agcagcctca catctgagga ctc 23

<210> SEQ ID NO 457
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 457
agcagcctga cttctgagaa ctc 23

<210> SEQ ID NO 458
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 458
agcagcctga catatgagga ctc 23

<210> SEQ ID NO 459
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 459
aacagcctga cttctgagga ctc 23

<210> SEQ ID NO 460
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 460
aacagcctga catctgagga ctt 23

<210> SEQ ID NO 461
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 461
agcagcctga catctgacga ctc 23

<210> SEQ ID NO 462
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 462
agcagcctga catctgaaga ctc 23

<210> SEQ ID NO 463
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 463
agcagcctga catctgagga cac 23

<210> SEQ ID NO 464
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 464
aacagcctga catctgaaga ctc 23

<210> SEQ ID NO 465
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 465
agccgattaa catctgatga ctc 23

<210> SEQ ID NO 466
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 466
aacagcctga catctgagga ttc 23

<210> SEQ ID NO 467
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 467
agaagcctga catctgag 18

<210> SEQ ID NO 468
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 468
agcagcctga caaatgagga ctc 23

<210> SEQ ID NO 469
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 469
aacagtctga catctgagga ctc 23

<210> SEQ ID NO 470
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 470
agcagcctga catctgatga ctc 23

<210> SEQ ID NO 471
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 471
agcagcctgg catctgagga ctc 23

<210> SEQ ID NO 472

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 472
agcagcccga catctgagga ctc 23

<210> SEQ ID NO 473
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 473
aacagcctga catctgagga ctc 23

<210> SEQ ID NO 474
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 474
agcagcttga catctgagga ctc 23

<210> SEQ ID NO 475
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 475
agcagcctga catctaagga ctc 23

<210> SEQ ID NO 476
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 476
cggagcctgg catctgagga ctc 23

<210> SEQ ID NO 477
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 477
agcagcctga caactgagga ctc 23

<210> SEQ ID NO 478
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 478
cgcagcctga catcggagga ttc 23

<210> SEQ ID NO 479
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 479
agaagcctga catctgagga ctc 23

<210> SEQ ID NO 480
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 480
agcagcctga catctgagga ctc 23

<210> SEQ ID NO 481
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 481
agtagattga catctgaaga ctc 23

<210> SEQ ID NO 482
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 482
aacagtctga catccgagga ctc 23

<210> SEQ ID NO 483
<211> LENGTH: 23
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 483
agcagcctga cctctgagga ctc 23

<210> SEQ ID NO 484
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 484
gccagattga catctgagga ttc 23

<210> SEQ ID NO 485
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 485
cggagcctga catctgagga ctc 23

<210> SEQ ID NO 486
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 486
aagagcctga catctgagga ctc 23

<210> SEQ ID NO 487
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 487
ctgagcctga catctgagga ctt 23

<210> SEQ ID NO 488
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 488
aacagcctga catctgagga ccc 23

<210> SEQ ID NO 489
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 489
cgcagcctga catctgagga cac 23

<210> SEQ ID NO 490
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 490
agcagcctaa catctgagga ctc 23

<210> SEQ ID NO 491
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 491
agcagtctga agtctgagga cac 23

<210> SEQ ID NO 492
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 492
accagtctga agtcagagga cac 23

<210> SEQ ID NO 493
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 493
agccatctga agtctgagga cac 23

<210> SEQ ID NO 494
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 494
accagtctga ggtctgagga cac 23

<210> SEQ ID NO 495
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 495
accagtctaa ggtctgagga cac 23

<210> SEQ ID NO 496
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 496
agcagtctga ggtctgagga cac 23

<210> SEQ ID NO 497
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 497
agcagtctga gttctaagga cac 23

<210> SEQ ID NO 498
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 498
agccgtctga agtctgagga cac 23

<210> SEQ ID NO 499
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 499
gaacagtctg caagctaatg acac 24

<210> SEQ ID NO 500
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 500
gaacagtctc caaactgatg acac 24

<210> SEQ ID NO 501
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 501
gaacagtctg caaactgatg acac 24

<210> SEQ ID NO 502
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 502
gaacagtctg caatctaatg acac 24

<210> SEQ ID NO 503
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 503
gaacagtctg caagctgatg acac 24

<210> SEQ ID NO 504
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 504
tgaacaactt gaaaactgag gacac 25

<210> SEQ ID NO 505
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 505
tgaacaacct gaaaactgag gacac 25

<210> SEQ ID NO 506
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 506
atatgaacag cttaagagcc gaagatac 28

<210> SEQ ID NO 507
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 507
aaatgaacag cttaagagct gaagacac 28

<210> SEQ ID NO 508
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 508
aaaagaacag cttaagagct gaagatac 28

<210> SEQ ID NO 509
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 509
agatggacag attaagagag gaagacac 28

<210> SEQ ID NO 510
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 510
aaatgaacaa cttaagagct gaagacat 28

<210> SEQ ID NO 511
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 511
agatgaacag attaagagag gaagacac 28

<210> SEQ ID NO 512
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 512
aaatgaacaa cttaagggct gaagacac 28

<210> SEQ ID NO 513
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 513
aaatgaacaa cttaagagct gaagacac 28

<210> SEQ ID NO 514
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 514
aaatgagcaa agtgagatct gaggacac 28

<210> SEQ ID NO 515
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 515
aaatgagcag tctgcaaagt gaagacac 28

<210> SEQ ID NO 516
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 516
aattgaactc tgtgaccaca gaggacac 28

<210> SEQ ID NO 517
<211> LENGTH: 28
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 517
agatgagcaa tgtgcgatct gaggaccc 28

<210> SEQ ID NO 518
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 518
agatgagcaa tgtgcgatcg gaggacac 28

<210> SEQ ID NO 519
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 519
agatgagcaa tgtgcgatct gaggacac 28

<210> SEQ ID NO 520
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 520
agctgagctc tgtgacaaat gaggacac 28

<210> SEQ ID NO 521
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 521
aactctgtga ctattgaaga tat 23

<210> SEQ ID NO 522
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 522
aactctgtga ctactgaaga tat 23

<210> SEQ ID NO 523
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 523
aattctgtga ctactgagga cgc 23

<210> SEQ ID NO 524
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 524
aactctttga ctgctgagga cac 23

<210> SEQ ID NO 525
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 525
aactctttga ctgctgaaga cac 23

<210> SEQ ID NO 526
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 526
aattctgtga ctactgagga cac 23

<210> SEQ ID NO 527
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 527
agttctgtga ctactgagga cac 23

<210> SEQ ID NO 528
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 528
aattctgtga cttctgagga cac 23

<210> SEQ ID NO 529
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 529
tcaaatgaat gccctgagag ctgaggaca 29

<210> SEQ ID NO 530
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 530
tcaaatgaac accctgagag ctgaggaca 29

<210> SEQ ID NO 531
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 531
tcaaatgaac accctgaggg ctgaggaca 29

<210> SEQ ID NO 532
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 532
tcaaatgaac accctgagag ctgaggcca 29

<210> SEQ ID NO 533
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 533
tcagatgaat gccctgagag ctgaggaca 29

<210> SEQ ID NO 534
<211> LENGTH: 21

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 534
caacctcaaa aatcaggaca c 21

<210> SEQ ID NO 535
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 535
caacctcaaa aatgaggaca c 21

<210> SEQ ID NO 536
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 536
caacctcaaa aatgaggaca t 21

<210> SEQ ID NO 537
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 537
agatcaccac tgtggacact gtagatac 28

<210> SEQ ID NO 538
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 538
agatcgccaa tgtggacact gcagatac 28

<210> SEQ ID NO 539
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 539
agatcaccag tgtggacact gcagatac 28

<210> SEQ ID NO 540
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 540
agatcgccag tgtggacact gcagatac 28

<210> SEQ ID NO 541
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 541
agatcaccac tgtggacact gcagatac 28

<210> SEQ ID NO 542
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 542
gcagcucaga agccugacat 20

<210> SEQ ID NO 543
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 543
ggagcucagc agccugacat 20

<210> SEQ ID NO 544
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 544
gcagcucagc agcctgacut 20

<210> SEQ ID NO 545
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 545
ggagcuccgc agccugacat 20

<210> SEQ ID NO 546
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 546
gcaacucagc agccugacaa 20

<210> SEQ ID NO 547
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 547
gcagcucagc agccugacct 20

<210> SEQ ID NO 548
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 548
gcaacucagc agcccgacat 20

<210> SEQ ID NO 549
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 549

ggagcuccac agccugacat                                              20


<210> SEQ ID NO 550
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 550

gcagtucaac agccugacat                                              20


<210> SEQ ID NO 551
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 551

tcagcucagc agccuggcat                                              20


<210> SEQ ID NO 552
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 552

ggagcutagt agatugacat                                              20


<210> SEQ ID NO 553
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 553
gcagcucagc agccugacat 20

<210> SEQ ID NO 554
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 554
gttgcucagc agccugacct 20

<210> SEQ ID NO 555
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 555
ggatcucagc agccugacct 20

<210> SEQ ID NO 556
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 556
ggagcuccgg agccuggcat 20

<210> SEQ ID NO 557
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 557
ggaucucagc agcccgacat 20

<210> SEQ ID NO 558

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 558
ggagcucaac agtcugacat 20

<210> SEQ ID NO 559
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 559
gcagcucaag agccugacat 20

<210> SEQ ID NO 560
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 560
ggagcucagc cgatuaacat 20

<210> SEQ ID NO 561
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 561
gcaacucagc agccugacat 20

<210> SEQ ID NO 562
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<220> FEATURE:
<221> NAME/KEY: source
<223> OTHER INFORMATION: /note="Description of Combined DNA/RNA
      Molecule: Synthetic oligonucleotide"

<400> SEQUENCE: 562
ggaactugcc agatugacat 20

<210> SEQ ID NO 563
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
ggagcucagc agccugacaa 20

<210> SEQ ID NO 564
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 564
ggacguccgc agccugacat 20

<210> SEQ ID NO 565
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 565
ggagcucctg agccugacat 20

<210> SEQ ID NO 566
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 566
gcaccucagc agccugacat 20

<210> SEQ ID NO 567

-continued

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 567
ggagcucaac agccugacat 20

<210> SEQ ID NO 568
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 568
gcaacugagc agccugacat 20

<210> SEQ ID NO 569
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 569
ggagcuaaac agcctgacut 20

<210> SEQ ID NO 570
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 570
ggaacucagc agccucacat 20

<210> SEQ ID NO 571
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Description of Combined DNA/RNA
Molecule: Synthetic oligonucleotide"

<400> SEQUENCE: 571
gcaacucagc agctugacat 20

<210> SEQ ID NO 572
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 572
ggatcucagc agccugacat 20

<210> SEQ ID NO 573
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 573
ggagcucagc agccugacct 20

<210> SEQ ID NO 574
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 574
gcagtucagc agccugacat 20

<210> SEQ ID NO 575
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 575
gcagcucaac agccugacat 20

<210> SEQ ID NO 576
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 576
gcatcucaac agccugacat 20

<210> SEQ ID NO 577
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 577
gcaguccagc agccugacat 20

<210> SEQ ID NO 578
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 578
gcagcugagc agccugacat 20

<210> SEQ ID NO 579
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 579
gcagcucagc agccuaacat 20

<210> SEQ ID NO 580
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 580
ggagcuccgg agccugacat 20

<210> SEQ ID NO 581
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 581
ggtgtugaac agccugacat 20

<210> SEQ ID NO 582
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 582
tgtacctgca aaugagcagt ctgagut 27

<210> SEQ ID NO 583
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 583
tgtacctgga aaugagcagt cugaggt 27

<210> SEQ ID NO 584
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 584
tgtacctgca aaugagccat cugaagt 27

<210> SEQ ID NO 585
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 585
tatacctgca aaugagcagt cugaagt 27

<210> SEQ ID NO 586
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 586
tttacctgca aaugaccagt cugaagt 27

<210> SEQ ID NO 587
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 587
tgtacctgca aaugagccgt cugaagt 27

<210> SEQ ID NO 588
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 588
tgtacctgca aaugagcagt cugaagt 27

```
<210> SEQ ID NO 589
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 589

tgttcctgca aaugaccagt cuaaggt                                          27


<210> SEQ ID NO 590
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 590

tgtacctgca aaugagcagt cugaggt                                          27


<210> SEQ ID NO 591
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 591

tgttcctgca aaugaccagt cugaggt                                          27


<210> SEQ ID NO 592
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 592

cttaaaaaug aacagtcucc aaa                                              23


<210> SEQ ID NO 593
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 593
cttaaaacug aacagtcugc aaa 23

<210> SEQ ID NO 594
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 594
cttaaaaaug aacagtcugc aaa 23

<210> SEQ ID NO 595
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 595
ctttaaaaug aacagtcugc aag 23

<210> SEQ ID NO 596
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 596
ctttaaaaug aacagtcugc aat 23

<210> SEQ ID NO 597
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 597
atgctctatc ugcaaatgaa caaccugaaa a 31

<210> SEQ ID NO 598
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 598
atgctctatc ugcaaatgaa caactugaaa a 31

<210> SEQ ID NO 599
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 599
gtctaccugc aaatgaacaa ctuaaggg 28

<210> SEQ ID NO 600
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 600
gtctacctgc agauggacag atuaagag 28

<210> SEQ ID NO 601
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 601
gtctaccugc aaaagaacag ctuaagag 28

<210> SEQ ID NO 602
<211> LENGTH: 28
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 602
gtctacctgc aaaugaacag ctuaagag 28

<210> SEQ ID NO 603
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 603
gtctacctgc auatgaacag ctuaagag 28

<210> SEQ ID NO 604
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 604
gtatacctgc aaaugaacaa ctuaagag 28

<210> SEQ ID NO 605
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 605
gtctaccugc aaatgaacaa ctuaagag 28

<210> SEQ ID NO 606
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 606
gtctaccuag agatgaacag atuaagag 28

<210> SEQ ID NO 607
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 607
gtctaccugc agatgaacag atuaagag 28

<210> SEQ ID NO 608
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 608
gctgtaccug caaatgagca aagugagat 29

<210> SEQ ID NO 609
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 609
agttttcttt aaaaugagca gtcugcaaa 29

<210> SEQ ID NO 610
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 610
cctgtaccug cagatgagca atgugcgat 29

<210> SEQ ID NO 611
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 611
gttcttcctc caautgaact ctgugacca 29

<210> SEQ ID NO 612
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 612
gttctttctg caautgaact ctgugacca 29

<210> SEQ ID NO 613
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 613
attctttatc cagcugagct ctgugacaa 29

<210> SEQ ID NO 614
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 614
ttcctgcagt ugaattctgt gacuac 26

<210> SEQ ID NO 615
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 615
ttcctgaagt ugaattctgt gacuac 26

<210> SEQ ID NO 616
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 616
ttcctgcagt ugaactctgt gacuat 26

<210> SEQ ID NO 617
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 617
tcactgaagt ugagttctgt gacuac 26

<210> SEQ ID NO 618
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 618
ttcctgcagt ugaactctgt gacuac 26

<210> SEQ ID NO 619
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 619
ttcctggaaa ugaactcttt gacugc 26

<210> SEQ ID NO 620
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 620
ttcttgaagt ugaattctgt gacuac 26

<210> SEQ ID NO 621
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 621
tacctgcagt ugaattctgt gacuac 26

<210> SEQ ID NO 622
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 622
tacctacagt ugaattctgt gacuac 26

<210> SEQ ID NO 623
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 623
tacctgcagt ugaattctgt gactuc 26

<210> SEQ ID NO 624
<211> LENGTH: 30

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 624
tcctctatct ucaaatgaac acccugagag 30

<210> SEQ ID NO 625
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 625
tcctctacct ucagatgaat gcccugagag 30

<210> SEQ ID NO 626
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 626
tcctctatct ucaaatgaac acccugaggg 30

<210> SEQ ID NO 627
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 627
tcctctatct ucaaatgaat gcccugagag 30

<210> SEQ ID NO 628
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: source
<223> OTHER INFORMATION: /note="Description of Combined DNA/RNA
      Molecule: Synthetic oligonucleotide"

<400> SEQUENCE: 628
ttgcagauca acaaccucaa aaa 23

<210> SEQ ID NO 629
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 629
ttacagauaa gcaaccucaa aaa 23

<210> SEQ ID NO 630
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 630
ggtattcctc aagaucacca ctguggaca 29

<210> SEQ ID NO 631
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 631
ggtattcctc aagaucgcca gtguggaca 29

<210> SEQ ID NO 632
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 632
ggtattcctc aagaucgcca atguggaca 29

<210> SEQ ID NO 633
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 633
ggtattcctc aagaucacca gtguggaca 29

<210> SEQ ID NO 634
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 634
gctcaagagc cugacatcug a 21

<210> SEQ ID NO 635
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 635
tctcaacagc cugacatcug a 21

<210> SEQ ID NO 636
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 636
gcttagtaga utgacatcug a 21

<210> SEQ ID NO 637
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 637
acttgccaga utgacatcug a 21

<210> SEQ ID NO 638
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 638
gctcagcagc cugacaaaug a 21

<210> SEQ ID NO 639
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 639
gttcagcagc cugacatcug a 21

<210> SEQ ID NO 640
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 640
gctcagccga utaacatcug a 21

<210> SEQ ID NO 641
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 641
gctcaacagc cugacatcug a 21

<210> SEQ ID NO 642
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 642
gctcagcagc cugacatcug a 21

<210> SEQ ID NO 643
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 643
actcagcagc cucacatcug a 21

<210> SEQ ID NO 644
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 644
tctcagcagc cugacctcug a 21

<210> SEQ ID NO 645
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 645
gctccggagc cugacatcug a 21

<210> SEQ ID NO 646

<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 646
gctccgcagc cugacaucgg a 21

<210> SEQ ID NO 647
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 647
actgagcagc cugacatcug a 21

<210> SEQ ID NO 648
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 648
gctcagcagc cuaacatcug a 21

<210> SEQ ID NO 649
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 649
tctcagcagc cugacatcug a 21

<210> SEQ ID NO 650
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Description of Combined DNA/RNA
Molecule: Synthetic oligonucleotide"

<400> SEQUENCE: 650
acucagcagc ccgacatcug a 21

<210> SEQ ID NO 651
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 651
gctcagcagc cugacttcug a 21

<210> SEQ ID NO 652
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 652
gctccugagc ctgacatcug a 21

<210> SEQ ID NO 653
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 653
actcagcagc utgacatcug a 21

<210> SEQ ID NO 654
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 654

-continued gtccagcagc cugacatcug a 21

<210> SEQ ID NO 655
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 655
gctgagcagc cugacataug a 21

<210> SEQ ID NO 656
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 656
gctccacagc cugacatcug a 21

<210> SEQ ID NO 657
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 657
gctcaacagu ctgacauccg a 21

<210> SEQ ID NO 658
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 658
cctcagcagc cugacatcug a 21

<210> SEQ ID NO 659
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 659
gctccgcagc cugacatcug a 21

<210> SEQ ID NO 660
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 660
tcucagcagc ccgacatcug a 21

<210> SEQ ID NO 661
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 661
gctcagcagc cuggcatcug a 21

<210> SEQ ID NO 662
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 662
actcagcagc cugacatcug a 21

<210> SEQ ID NO 663
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 663
gctcagaagc cugacatcug a 21

<210> SEQ ID NO 664
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 664
tctcagcagc cugacatcua a 21

<210> SEQ ID NO 665
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 665
gctccggagc cuggcatcug a 21

<210> SEQ ID NO 666
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 666
gttgaacagc cugacatcug a 21

<210> SEQ ID NO 667
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 667
actcagcagc cugacaacug a 21

<210> SEQ ID NO 668
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 668
gctaaacagc cugacttcug a 21

<210> SEQ ID NO 669
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 669
cgtccgcagc cugacatcug a 21

<210> SEQ ID NO 670
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 670
gctcaacagu ctgacatcug a 21

<210> SEQ ID NO 671
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 671
gctcagcagc cugacctcug a 21

<210> SEQ ID NO 672
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 672
gttcaacagc cugacatcug a 21

<210> SEQ ID NO 673
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 673
aatgaccagu ctgaggtcug ag 22

<210> SEQ ID NO 674
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 674
aatgagcagu ctgaagtcug ag 22

<210> SEQ ID NO 675
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 675
aatgaccagu ctaaggtcug ag 22

<210> SEQ ID NO 676
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 676
aatgagccau ctgaagtcug ag 22

<210> SEQ ID NO 677
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 677
aatgagccgu ctgaagtcug ag 22

<210> SEQ ID NO 678
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 678
aatgagcagu ctgagttcua ag 22

<210> SEQ ID NO 679
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 679
aatgagcagu ctgaggtcug ag 22

<210> SEQ ID NO 680
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 680
aatgaccagu ctgaagucag ag 22

<210> SEQ ID NO 681
<211> LENGTH: 26
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 681
taaaaatgaa cagucuccaa acugat 26

<210> SEQ ID NO 682
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 682
ttaaaatgaa cagucugcaa gcuaat 26

<210> SEQ ID NO 683
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 683
ttaaaatgaa cagucugcaa tcuaat 26

<210> SEQ ID NO 684
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 684
ttaaaatgaa cagucugcaa gcugat 26

<210> SEQ ID NO 685
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 685
taaaactgaa cagucugcaa acugat 26

<210> SEQ ID NO 686
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 686
taaaaatgaa cagucugcaa acugat 26

<210> SEQ ID NO 687
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 687
tctatctgca aaugaacaac ttgaaaacug ag 32

<210> SEQ ID NO 688
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 688
tctatctgca aaugaacaac ctgaaaacug ag 32

<210> SEQ ID NO 689
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 689
ctgcaaauga acaacttaag agcugaa 27

<210> SEQ ID NO 690
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 690
ctgcaaaaga acagcutaag agcugaa 27

<210> SEQ ID NO 691
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 691
ctgcagauga acagatuaag agaggaa 27

<210> SEQ ID NO 692
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 692
ctagagauga acagatuaag agaggaa 27

<210> SEQ ID NO 693
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 693
ctgcagaugg acagatuaag agaggaa 27

<210> SEQ ID NO 694
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 694
ctgcaaauga acagcttaag agcugaa 27

<210> SEQ ID NO 695
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 695
ctgcaaatga acaacutaag ggcugaa 27

<210> SEQ ID NO 696
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 696
ctgcauatga acagctuaag agccgaa 27

<210> SEQ ID NO 697
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 697
cctgcagaug agcaatgtgc gatcugag 28

<210> SEQ ID NO 698
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 698
cctgcagaug agcaatgtgc gaucggag 28

<210> SEQ ID NO 699
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 699
tatccagctg agcuctgtga caaaugag 28

<210> SEQ ID NO 700
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 700
cctccaautg aactctguga ccacagag 28

<210> SEQ ID NO 701
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 701
tctgcaautg aactctguga ccacagag 28

<210> SEQ ID NO 702
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 702
ctttaaaatg agcaguctgc aaagugaa 28

<210> SEQ ID NO 703
<211> LENGTH: 28

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 703
cctgcaaaug agcaaagtga gatcugag 28

<210> SEQ ID NO 704
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 704
agttgagttc ugtgactacu gagg 24

<210> SEQ ID NO 705
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 705
aaatgaactc uttgactgcu gagg 24

<210> SEQ ID NO 706
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 706
agttgaattc ugtgacttcu gagg 24

<210> SEQ ID NO 707
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: source
<223> OTHER INFORMATION: /note="Description of Combined DNA/RNA
      Molecule: Synthetic oligonucleotide"

<400> SEQUENCE: 707
aaatgaactc uttgactgcu gaag 24

<210> SEQ ID NO 708
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 708
agttgaactc ugtgactacu gaag 24

<210> SEQ ID NO 709
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 709
agttgaattc ugtgactacu gagg 24

<210> SEQ ID NO 710
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 710
agttgaacuc tgtgactatu gaag 24

<210> SEQ ID NO 711
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 711
cttcaaatga acacccugag ggcugag 27

<210> SEQ ID NO 712
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 712
cttcagatga augccctgag agcugag 27

<210> SEQ ID NO 713
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 713
cttcaaatga augccctgag agcugag 27

<210> SEQ ID NO 714
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 714
cttcaaatga acacccugag agcugag 27

<210> SEQ ID NO 715
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 715
cagatcaaca accucaaaaa ucag 24

<210> SEQ ID NO 716
<211> LENGTH: 24
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 716
cagataagca accucaaaaa ugag 24

<210> SEQ ID NO 717
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 717
cagatcaaca accucaaaaa ugag 24

<210> SEQ ID NO 718
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 718
tattcctcaa gaucaccagt gtggacacug ca 32

<210> SEQ ID NO 719
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 719
tattcctcaa gaucgccagt gtggacacug ca 32

<210> SEQ ID NO 720
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 720
tattcctcaa gaucgccaat gtggacacug ca 32

<210> SEQ ID NO 721
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 721
tattcctcaa gaucaccact gtggacacug ca 32

<210> SEQ ID NO 722
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 722
tattcctcaa gaucaccact gtggacactg ua 32

<210> SEQ ID NO 723
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 723
cagcagccug acatcugagg ac 22

<210> SEQ ID NO 724
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 724
caacagucug acatcugagg ac 22

<210> SEQ ID NO 725

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 725
tgccagautg acatcugagg at 22

<210> SEQ ID NO 726
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 726
cagcagccug acatcuaagg ac 22

<210> SEQ ID NO 727
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 727
cagaagccug acatcugag 19

<210> SEQ ID NO 728
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 728
caacagccug acatcugagg at 22

<210> SEQ ID NO 729
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Description of Combined DNA/RNA
      Molecule: Synthetic oligonucleotide"

<400> SEQUENCE: 729
cagcagccuc acatcugagg ac 22

<210> SEQ ID NO 730
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 730
gagcagccug acataugagg ac 22

<210> SEQ ID NO 731
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 731
cagcagcutg acatcugagg ac 22

<210> SEQ ID NO 732
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 732
cagccgauta acatctgaug ac 22

<210> SEQ ID NO 733
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
cagcagccug acaaaugagg ac 22

<210> SEQ ID NO 734

<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 734
cagcagccug acaacugagg ac 22

<210> SEQ ID NO 735
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 735
tagtagautg acatcugaag ac 22

<210> SEQ ID NO 736
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 736
cagcagcccg acaucugagg ac 22

<210> SEQ ID NO 737
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 737
cagcagccug acatcugaag ac 22

<210> SEQ ID NO 738
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 738
aaacagccug acttcugagg ac 22

<210> SEQ ID NO 739
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 739
gagcagccug acaucugagg ac 22

<210> SEQ ID NO 740
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 740
cagaagccug acaucugagg ac 22

<210> SEQ ID NO 741
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 741
ccacagccug acaucugagg ac 22

<210> SEQ ID NO 742
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 742
ccgcagccug acaucugagg ac 22

<210> SEQ ID NO 743
<211> LENGTH: 22
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 743
cagcagccug acatctgaug ac 22

<210> SEQ ID NO 744
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 744
caagagccug acatcugagg ac 22

<210> SEQ ID NO 745
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 745
cagcagccug acctcugagg ac 22

<210> SEQ ID NO 746
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 746
ccggagccug gcatcugagg ac 22

<210> SEQ ID NO 747
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 747
caacagccug acatcugagg ac 22

<210> SEQ ID NO 748
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 748
caacagccug acatcugaag ac 22

<210> SEQ ID NO 749
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 749
cctgagccug acatcugagg ac 22

<210> SEQ ID NO 750
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 750
cagcagccua acatcugagg ac 22

<210> SEQ ID NO 751
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 751
cagcagccug gcatcugagg ac 22

<210> SEQ ID NO 752

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 752
gaacagccug acatcugagg ac 22

<210> SEQ ID NO 753
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 753
cagcagccug acttcugaga ac 22

<210> SEQ ID NO 754
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 754
caacagucug acauccgagg ac 22

<210> SEQ ID NO 755
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 755
ccggagccug acatcugagg ac 22

<210> SEQ ID NO 756
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<220> FEATURE:
<221> NAME/KEY: source
<223> OTHER INFORMATION: /note="Description of Combined DNA/RNA
      Molecule: Synthetic oligonucleotide"

<400> SEQUENCE: 756
ccgcagccug acaucggagg at 22

<210> SEQ ID NO 757
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 757
cagcagccug acatcugacg ac 22

<210> SEQ ID NO 758
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 758
gaccaguctg aggtcugagg ac 22

<210> SEQ ID NO 759
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 759
gagcaguctg agttcuaagg ac 22

<210> SEQ ID NO 760
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 760
gagccauctg aagtcugagg ac 22

<210> SEQ ID NO 761
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 761
gaccagucta aggtcugagg ac 22

<210> SEQ ID NO 762
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 762
gagcaguctg aagtcugagg ac 22

<210> SEQ ID NO 763
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 763
gagccguctg aagtcugagg ac 22

<210> SEQ ID NO 764
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 764
gagcaguctg aggtcugagg ac 22

<210> SEQ ID NO 765
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 765
gaccaguctg aagucagagg ac 22

<210> SEQ ID NO 766
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 766
aaatgaacag uctgcaagct aaugac 26

<210> SEQ ID NO 767
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 767
aaatgaacag uctccaaact gaugac 26

<210> SEQ ID NO 768
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 768
aaatgaacag tcugcaagct gaugac 26

<210> SEQ ID NO 769
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 769
aaatgaacag uctgcaaact gaugac 26

<210> SEQ ID NO 770
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 770
aaatgaacag uctgcaatct aaugac 26

<210> SEQ ID NO 771
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 771
aactgaacag uctgcaaact gaugac 26

<210> SEQ ID NO 772
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 772
ctgcaaauga acaacttgaa aacugaggac 30

<210> SEQ ID NO 773
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 773
ctgcaaauga acaacctgaa aacugaggac 30

<210> SEQ ID NO 774
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 774
caaatgaaca gcutaagagc ugaagac 27

<210> SEQ ID NO 775
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 775
cauatgaaca gctuaagagc cgaagat 27

<210> SEQ ID NO 776
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 776
caaaagaaca gcutaagagc ugaagat 27

<210> SEQ ID NO 777
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 777
caaatgaaca acutaagagc ugaagac 27

<210> SEQ ID NO 778
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 778
cagaugaaca gatuaagaga ggaagac 27

<210> SEQ ID NO 779
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 779
gagaugaaca gatuaagaga ggaagac 27

<210> SEQ ID NO 780
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 780
caaatgaaca acutaagggc ugaagac 27

<210> SEQ ID NO 781
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 781
cagauggaca gatuaagaga ggaagac 27

<210> SEQ ID NO 782
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 782
ccagctgagc uctgtgacaa augaggac 28

<210> SEQ ID NO 783
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 783
gcaaatgagc aaagugagat cugaggac 28

<210> SEQ ID NO 784
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 784
ccaautgaac tctgugacca cagaggac 28

<210> SEQ ID NO 785
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 785
taaaatgagc aguctgcaaa gugaagac 28

<210> SEQ ID NO 786
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 786
gcagatgagc aaugtgcgau cggaggac 28

<210> SEQ ID NO 787
<211> LENGTH: 28
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 787
gcaautgaac tctgugacca cagaggac 28

<210> SEQ ID NO 788
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 788
gcagatgagc aaugtgcgat cugaggac 28

<210> SEQ ID NO 789
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 789
ttgaactcug tgactacuga aga 23

<210> SEQ ID NO 790
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 790
atgaactcut tgactgcuga gga 23

<210> SEQ ID NO 791
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 791
ttgaattcug tgacttcuga gga 23

<210> SEQ ID NO 792
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 792
ttgagttcug tgactacuga gga 23

<210> SEQ ID NO 793
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 793
ttgaactcug tgactatuga aga 23

<210> SEQ ID NO 794
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 794
ttgaattcug tgactacuga gga 23

<210> SEQ ID NO 795
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 795
atgaactcut tgactgcuga aga 23

<210> SEQ ID NO 796
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 796
cagatgaaug ccctgagagc ugaggac 27

<210> SEQ ID NO 797
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 797
caaatgaaca cccugagagc ugaggac 27

<210> SEQ ID NO 798
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 798
caaatgaaug ccctgagagc ugaggac 27

<210> SEQ ID NO 799
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 799
caaatgaaca cccugagggc ugaggac 27

<210> SEQ ID NO 800
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 800
caaatgaaca cccugagagc ugaggcc 27

<210> SEQ ID NO 801
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 801
caacaaccuc aaaaaucagg ac 22

<210> SEQ ID NO 802
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 802
aagcaaccuc aaaaaugagg ac 22

<210> SEQ ID NO 803
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 803
caacaaccuc aaaaaugagg ac 22

<210> SEQ ID NO 804
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 804
aagatcgcca augtggacac ugcagat 27

<210> SEQ ID NO 805
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 805
aagatcacca cugtggacac ugcagat 27

<210> SEQ ID NO 806
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 806
aagatcacca gugtggacac ugcagat 27

<210> SEQ ID NO 807
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 807
aagatcgcca gugtggacac ugcagat 27

<210> SEQ ID NO 808
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 808
aagatcacca cugtggacac tguagat 27

<210> SEQ ID NO 809
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 809
agcagcccga caucugagga ct 22

<210> SEQ ID NO 810
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 810
agcagccuga catctgauga ct 22

<210> SEQ ID NO 811
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 811
gccagatuga catctgagga ut 22

<210> SEQ ID NO 812
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 812
cggagccugg catcugagga ct 22

<210> SEQ ID NO 813
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 813
aacagccuga cttcugagga ct 22

<210> SEQ ID NO 814
<211> LENGTH: 22
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 814
agaagccuga catcugagga ct 22

<210> SEQ ID NO 815
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 815
aacagccuga catctgagga ut 22

<210> SEQ ID NO 816
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 816
agcagccuga catcugagga ca 22

<210> SEQ ID NO 817
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 817
agaagccuga catcugag 18

<210> SEQ ID NO 818
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 818
aacagccuga catcugagga cc 22

<210> SEQ ID NO 819
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 819
agccgatuaa catctgauga ct 22

<210> SEQ ID NO 820
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 820
agcagccuga cttcugagaa ct 22

<210> SEQ ID NO 821
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 821
agcagccuga cctcugagga ct 22

<210> SEQ ID NO 822
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 822
ctgagccuga catcugagga ct 22

<210> SEQ ID NO 823
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 823
aacagccuga catcugagga ct 22

<210> SEQ ID NO 824
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 824
aacagccuga catcugaaga ct 22

<210> SEQ ID NO 825
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 825
agcagccuga catcugaaga ct 22

<210> SEQ ID NO 826
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 826
agcagcutga catcugagga ct 22

<210> SEQ ID NO 827
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 827
agcagccuga catcugagga ct 22

<210> SEQ ID NO 828
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 828
aagagccuga catcugagga ct 22

<210> SEQ ID NO 829
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 829
agcagccuga caacugagga ct 22

<210> SEQ ID NO 830
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 830
cgcagccuga catcugagga ct 22

<210> SEQ ID NO 831
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 831
agcagccugg catcugagga ct 22

<210> SEQ ID NO 832
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 832
agcagccuga catcuaagga ct 22

<210> SEQ ID NO 833
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 833
agtagautga catcugaaga ct 22

<210> SEQ ID NO 834
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 834
cggagccuga catcugagga ct 22

<210> SEQ ID NO 835
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 835
agcagccuga catcugacga ct 22

<210> SEQ ID NO 836
<211> LENGTH: 22

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 836
cacagccuga catcugagga ct 22

<210> SEQ ID NO 837
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 837
agcagccuaa catcugagga ct 22

<210> SEQ ID NO 838
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 838
aacagucuga cauccgagga ct 22

<210> SEQ ID NO 839
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 839
aacagtcuga catcugagga ct 22

<210> SEQ ID NO 840
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: source
<223> OTHER INFORMATION: /note="Description of Combined DNA/RNA
Molecule: Synthetic oligonucleotide"

<400> SEQUENCE: 840
agcagccuga caaaugagga ct 22

<210> SEQ ID NO 841
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 841
agcagccuga cataugagga ct 22

<210> SEQ ID NO 842
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 842
cgcagccuga catcugagga ca 22

<210> SEQ ID NO 843
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 843
agcagccuca catcugagga ct 22

<210> SEQ ID NO 844
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 844
cgcagccuga catcggagga ut 22

<210> SEQ ID NO 845
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 845
gagcaguctg aggtcugagg aca 23

<210> SEQ ID NO 846
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 846
gaccagucta aggtcugagg aca 23

<210> SEQ ID NO 847
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 847
gagcaguctg agttcuaagg aca 23

<210> SEQ ID NO 848
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 848
gaccaguctg aggtcugagg aca 23

<210> SEQ ID NO 849
<211> LENGTH: 23
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 849
gagccgugtg aagtcugagg aca 23

<210> SEQ ID NO 850
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 850
gaccagugtg aagucagagg aca 23

<210> SEQ ID NO 851
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 851
gagccaugtg aagtcugagg aca 23

<210> SEQ ID NO 852
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 852
gagcagugtg aagtcugagg aca 23

<210> SEQ ID NO 853
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 853
aaatgaacag uctgcaatct aaugaca 27

<210> SEQ ID NO 854
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 854
aactgaacag uctgcaaact gaugaca 27

<210> SEQ ID NO 855
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 855
aaatgaacag uctgcaagct aaugaca 27

<210> SEQ ID NO 856
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 856
aaatgaacag tcugcaagct gaugaca 27

<210> SEQ ID NO 857
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 857
aaatgaacag uctgcaaact gaugaca 27

<210> SEQ ID NO 858

<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 858
aaatgaacag uctccaaact gaugaca 27

<210> SEQ ID NO 859
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 859
caaatgaaca accugaaaac ugaggaca 28

<210> SEQ ID NO 860
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 860
caaatgaaca acutgaaaac ugaggaca 28

<210> SEQ ID NO 861
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 861
atgaacaacu taagagcuga agaca 25

<210> SEQ ID NO 862
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<220> FEATURE:
<221> NAME/KEY: source
<223> OTHER INFORMATION: /note="Description of Combined DNA/RNA
      Molecule: Synthetic oligonucleotide"

<400> SEQUENCE: 862
atgaacaacu taagggcuga agaca 25

<210> SEQ ID NO 863
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 863
atgaacagcu taagagcuga agaca 25

<210> SEQ ID NO 864
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 864
auggacagat uaagagagga agaca 25

<210> SEQ ID NO 865
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 865
aagaacagct uaagagctga agaua 25

<210> SEQ ID NO 866
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 866
augaacagat uaagagagga agaca 25

<210> SEQ ID NO 867
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 867
atgaacagct uaagagccga agaua 25

<210> SEQ ID NO 868
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 868
caaatgagca aagugagatc ugaggaca 28

<210> SEQ ID NO 869
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 869
cagatgagca augtgcgatc ugaggaca 28

<210> SEQ ID NO 870
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 870
cagatgagca augtgcgatc ugaggacc 28

<210> SEQ ID NO 871
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 871
caautgaact ctgugaccac agaggaca 28

<210> SEQ ID NO 872
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 872
cagatgagca augtgcgauc ggaggaca 28

<210> SEQ ID NO 873
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 873
aaaatgagca guctgcaaag ugaagaca 28

<210> SEQ ID NO 874
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 874
cagctgagcu ctgtgacaaa ugaggaca 28

<210> SEQ ID NO 875
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 875
gaactctgug actactgaag aua 23

<210> SEQ ID NO 876
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 876
gaattctgug acttcugagg aca 23

<210> SEQ ID NO 877
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 877
gaactctgug actattgaag aua 23

<210> SEQ ID NO 878
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 878
gaattcugtg actacugagg acg 23

<210> SEQ ID NO 879
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 879
gaactctutg actgcugagg aca 23

-continued

<210> SEQ ID NO 880
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 880
gaattctgug actacugagg aca 23

<210> SEQ ID NO 881
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 881
gaactctutg actgcugaag aca 23

<210> SEQ ID NO 882
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 882
gagttcugtg actacugagg aca 23

<210> SEQ ID NO 883
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 883
tcaaatgaau gccctgagag cugaggaca 29

<210> SEQ ID NO 884
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 884
tcaaatgaac acccugagag cugaggaca 29

<210> SEQ ID NO 885
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 885
tcaaatgaac acccugaggg cugaggaca 29

<210> SEQ ID NO 886
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 886
tcaaatgaac acccugagag cugaggcca 29

<210> SEQ ID NO 887
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 887
tcagatgaau gccctgagag cugaggaca 29

<210> SEQ ID NO 888
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 888
aaccucaaaa augaggaca 19

<210> SEQ ID NO 889
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 889
aaccucaaaa aucaggaca 19

<210> SEQ ID NO 890
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 890
aagatcgcca atguggacac tgcagaua 28

<210> SEQ ID NO 891
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 891
aagatcgcca gtguggacac tgcagaua 28

<210> SEQ ID NO 892
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 892
aagatcacca ctguggacac tgcagaua 28

<210> SEQ ID NO 893
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 893
aagatcacca gtguggacac tgcagaua 28

<210> SEQ ID NO 894
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 894
aagatcacca ctguggacac tgtagaua 28

<210> SEQ ID NO 895
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 895
cgcagccuga catctgagga cuc 23

<210> SEQ ID NO 896
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 896
cacagcctga cauctgagga cuc 23

<210> SEQ ID NO 897
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 897
agcagcctca cauctgagga cuc 23

<210> SEQ ID NO 898
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 898
agcagcctga cutctgagaa cuc 23

<210> SEQ ID NO 899
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 899
agcagccuga catatgagga cuc 23

<210> SEQ ID NO 900
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 900
aacagcctga cutctgagga cuc 23

<210> SEQ ID NO 901
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 901
aacagcctga cauctgagga cut 23

<210> SEQ ID NO 902
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 902
agcagcctga cauctgacga cuc 23

<210> SEQ ID NO 903
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 903
agcagccuga catctgaaga cuc 23

<210> SEQ ID NO 904
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 904
agcagccuga catcugagga cac 23

<210> SEQ ID NO 905
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 905
aacagcctga cauctgaaga cuc 23

<210> SEQ ID NO 906
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 906
agccgattaa cauctgatga cuc 23

<210> SEQ ID NO 907
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 907
aacagcctga cauctgagga tuc 23

<210> SEQ ID NO 908
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 908
agaagccuga catcugag 18

<210> SEQ ID NO 909
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 909
agcagccuga caaatgagga cuc 23

<210> SEQ ID NO 910
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 910
aacagtctga cauctgagga cuc 23

<210> SEQ ID NO 911
<211> LENGTH: 23
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 911
agcagccuga catctgatga cuc 23

<210> SEQ ID NO 912
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 912
agcagcctgg cauctgagga cuc 23

<210> SEQ ID NO 913
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 913
agcagcccga cauctgagga cuc 23

<210> SEQ ID NO 914
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 914
aacagcctga cauctgagga cuc 23

<210> SEQ ID NO 915
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 915
agcagcttga cauctgagga cuc 23

<210> SEQ ID NO 916
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 916
agcagccuga catctaagga cuc 23

<210> SEQ ID NO 917
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 917
cggagccugg catctgagga cuc 23

<210> SEQ ID NO 918
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 918
agcagccuga caactgagga cuc 23

<210> SEQ ID NO 919
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 919
cgcagccuga catcggagga tuc 23

<210> SEQ ID NO 920
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 920
agaagcctga cauctgagga cuc 23

<210> SEQ ID NO 921
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 921
agcagcctga cauctgagga cuc 23

<210> SEQ ID NO 922
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 922
agtagattga cauctgaaga cuc 23

<210> SEQ ID NO 923
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 923
aacagtctga cauccgagga cuc 23

<210> SEQ ID NO 924
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 924
agcagcctga ccuctgagga cuc 23

<210> SEQ ID NO 925
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 925
gccagattga cauctgagga tuc 23

<210> SEQ ID NO 926
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 926
cggagccuga catctgagga cuc 23

<210> SEQ ID NO 927
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 927
aagagcctga cauctgagga cuc 23

<210> SEQ ID NO 928
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 928
ctgagcctga cauctgagga cut 23

<210> SEQ ID NO 929
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 929
aacagccuga catcugagga ccc 23

<210> SEQ ID NO 930
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 930
cgcagccuga catcugagga cac 23

<210> SEQ ID NO 931
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 931
agcagcctaa cauctgagga cuc 23

<210> SEQ ID NO 932
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 932
agcaguctga agtcugagga cac 23

<210> SEQ ID NO 933
<211> LENGTH: 23

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 933
accagucuga agucagagga cac 23

<210> SEQ ID NO 934
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 934
agccaucuga agucugagga cac 23

<210> SEQ ID NO 935
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 935
accagucuga ggucugagga cac 23

<210> SEQ ID NO 936
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 936
accagucuaa ggucugagga cac 23

<210> SEQ ID NO 937
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: source
<223> OTHER INFORMATION: /note="Description of Combined DNA/RNA
Molecule: Synthetic oligonucleotide"

<400> SEQUENCE: 937
agcaguctga ggtcugagga cac 23

<210> SEQ ID NO 938
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 938
agcaguctga gttcuaagga cac 23

<210> SEQ ID NO 939
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 939
agccguctga agtcugagga cac 23

<210> SEQ ID NO 940
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 940
gaacagtcug caagctaaug acac 24

<210> SEQ ID NO 941
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 941
gaacagtcuc caaactgaug acac 24

<210> SEQ ID NO 942
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 942
gaacagtcug caaactgaug acac 24

<210> SEQ ID NO 943
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 943
gaacagtcug caatctaaug acac 24

<210> SEQ ID NO 944
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 944
gaacagtcug caagctgaug acac 24

<210> SEQ ID NO 945
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 945
tgaacaacut gaaaacugag gacac 25

<210> SEQ ID NO 946
<211> LENGTH: 25
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 946
tgaacaaccu gaaaacugag gacac 25

<210> SEQ ID NO 947
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 947
atatgaacag ctuaagagcc gaagauac 28

<210> SEQ ID NO 948
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 948
aaatgaacag cutaagagcu gaagacac 28

<210> SEQ ID NO 949
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 949
aaaagaacag ctuaagagct gaagauac 28

<210> SEQ ID NO 950
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 950
agauggacag atuaagagag gaagacac 28

<210> SEQ ID NO 951
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 951
aaatgaacaa cutaagagcu gaagacat 28

<210> SEQ ID NO 952
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 952
agaugaacag atuaagagag gaagacac 28

<210> SEQ ID NO 953
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 953
aaatgaacaa cutaagggcu gaagacac 28

<210> SEQ ID NO 954
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 954
aaatgaacaa cutaagagcu gaagacac 28

<210> SEQ ID NO 955

<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 955
aaatgagcaa agugagatcu gaggacac 28

<210> SEQ ID NO 956
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 956
aaatgagcag uctgcaaagu gaagacac 28

<210> SEQ ID NO 957
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 957
aautgaactc tgugaccaca gaggacac 28

<210> SEQ ID NO 958
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 958
agatgagcaa ugtgcgatcu gaggaccc 28

<210> SEQ ID NO 959
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Description of Combined DNA/RNA
      Molecule: Synthetic oligonucleotide"

<400> SEQUENCE: 959
agatgagcaa ugtgcgaucg gaggacac 28

<210> SEQ ID NO 960
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 960
agatgagcaa ugtgcgatcu gaggacac 28

<210> SEQ ID NO 961
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 961
agctgagcuc tgtgacaaau gaggacac 28

<210> SEQ ID NO 962
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 962
aactctguga ctattgaaga uat 23

<210> SEQ ID NO 963
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 963
aactctgtga cuactgaaga uat 23

<210> SEQ ID NO 964
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 964
aattcugtga ctacugagga cgc 23

<210> SEQ ID NO 965
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 965
aactcuttga ctgcugagga cac 23

<210> SEQ ID NO 966
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 966
aactcuttga ctgcugaaga cac 23

<210> SEQ ID NO 967
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 967
aattcugtga ctacugagga cac 23

<210> SEQ ID NO 968
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 968
agttcugtga ctacugagga cac 23

<210> SEQ ID NO 969
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 969
aattcugtga cttcugagga cac 23

<210> SEQ ID NO 970
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 970
tcaaatgaau gccctgagag cugaggaca 29

<210> SEQ ID NO 971
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 971
tcaaatgaac acccugagag cugaggaca 29

<210> SEQ ID NO 972
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 972
tcaaatgaac acccugaggg cugaggaca 29

<210> SEQ ID NO 973
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 973
tcaaatgaac acccugagag cugaggcca 29

<210> SEQ ID NO 974
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 974
tcagatgaau gccctgagag cugaggaca 29

<210> SEQ ID NO 975
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 975
caaccucaaa aaucaggaca c 21

<210> SEQ ID NO 976
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 976
caaccucaaa aaugaggaca c 21

<210> SEQ ID NO 977
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 977

caaccucaaa aaugaggaca t                                              21


<210> SEQ ID NO 978
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 978

agatcaccac tguggacact gtagauac                                       28


<210> SEQ ID NO 979
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 979

agatcgccaa tguggacact gcagauac                                       28


<210> SEQ ID NO 980
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 980

agatcaccag tguggacact gcagauac                                       28


<210> SEQ ID NO 981
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 981
```

agatcgccag tguggacact gcagauac 28

<210> SEQ ID NO 982
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 982
agatcaccac tguggacact gcagauac 28

<210> SEQ ID NO 983
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 983
gactgtgaga gtggtgcctt 20

<210> SEQ ID NO 984
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 984
gacagtgacc agagtccctt 20

<210> SEQ ID NO 985
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 985
gacggtgacc gtggtccctg 20

<210> SEQ ID NO 986
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 986
gactgtgaga ctggtgcctt 20

<210> SEQ ID NO 987
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 987
gactgtgaga gaggtgcctt 20

<210> SEQ ID NO 988
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 988
gacggtgact gaggttcctt 20

<210> SEQ ID NO 989
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 989
aacggtgacc gtggtccctg 20

<210> SEQ ID NO 990
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 990
gagacggtga ctgaggttcc 20

<210> SEQ ID NO 991
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 991
gagactgtga gactggtgcc 20

<210> SEQ ID NO 992
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 992
gagacggtga ccgtggtccc 20

<210> SEQ ID NO 993
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 993
gaaacggtga ccgtggtccc 20

<210> SEQ ID NO 994
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 994
gagactgtga gagtggtgcc 20

<210> SEQ ID NO 995
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 995
gagacagtga ccagagtccc 20

<210> SEQ ID NO 996
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 996
gagactgtga gagaggtgcc 20

<210> SEQ ID NO 997
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 997
agacggtgac tgaggttcc 19

<210> SEQ ID NO 998
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 998
agacggtgac cgtggtccc 19

<210> SEQ ID NO 999
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 999
agactgtgag actggtgcc 19

<210> SEQ ID NO 1000
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1000
aaacggtgac cgtggtccc 19

<210> SEQ ID NO 1001
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1001
agactgtgag agaggtgcc 19

<210> SEQ ID NO 1002
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1002
agacagtgac cagagtccc 19

<210> SEQ ID NO 1003
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1003
agactgtgag agtggtgcc 19

<210> SEQ ID NO 1004

<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1004
gactgtgaga gtggtgcct 19

<210> SEQ ID NO 1005
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1005
gacggtgacc gtggtccct 19

<210> SEQ ID NO 1006
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1006
aacggtgacc gtggtccct 19

<210> SEQ ID NO 1007
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1007
gacagtgacc agagtccct 19

<210> SEQ ID NO 1008
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1008
gacggtgact gaggttcct 19

<210> SEQ ID NO 1009
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1009
gactgtgaga gaggtgcct 19

<210> SEQ ID NO 1010
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1010
gactgtgaga ctggtgcct 19

<210> SEQ ID NO 1011
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1011
ctgaggagac tgtgagagtg g 21

<210> SEQ ID NO 1012
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1012
ctgaggagac ggtgactgag g 21

<210> SEQ ID NO 1013
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1013
ctgaggagac tgtgagactg g 21

<210> SEQ ID NO 1014
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1014
ctgaggagac tgtgagagag g 21

<210> SEQ ID NO 1015
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 1015
ctgcagagac agtgaccaga g 21

<210> SEQ ID NO 1016
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1016
ctgaggagac ggtgaccgtg g 21

<210> SEQ ID NO 1017
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1017
ctgaggaaac ggtgaccgtg g 21

<210> SEQ ID NO 1018
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 1018
gactgtgaga guggtgccut 20

<210> SEQ ID NO 1019
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 1019
gacagugacc agagtcccut 20

<210> SEQ ID NO 1020
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1020
gacggtgacc guggtcccug                                          20

<210> SEQ ID NO 1021
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1021
gactgtgaga cuggtgccut                                          20

<210> SEQ ID NO 1022
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1022
gactgugaga gaggtgccut                                          20

<210> SEQ ID NO 1023
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1023
gacggtgacu gaggttccut                                          20

<210> SEQ ID NO 1024
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1024
aacggtgacc guggtcccug 20

<210> SEQ ID NO 1025
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1025
gagacgguga ctgaggtucc 20

<210> SEQ ID NO 1026
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1026
gagactguga gactggugcc 20

<210> SEQ ID NO 1027
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1027
gagacgguga ccgtgguccc 20

<210> SEQ ID NO 1028
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1028
gaaacgguga ccgtgguccc 20

<210> SEQ ID NO 1029
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1029
gagactguga gagtggugcc 20

<210> SEQ ID NO 1030
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1030
gagacaguga ccagaguccc 20

<210> SEQ ID NO 1031
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1031
gagactguga gagaggugcc 20

<210> SEQ ID NO 1032
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1032
agacggugac tgaggtucc 19

<210> SEQ ID NO 1033
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1033
agacggugac cgtgguccc 19

<210> SEQ ID NO 1034
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1034
agactgugag actggugcc 19

<210> SEQ ID NO 1035
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1035
aaacggugac cgtgguccc 19

<210> SEQ ID NO 1036
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1036
agactgugag agaggugcc 19

<210> SEQ ID NO 1037
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1037
agacagugac cagaguccc 19

<210> SEQ ID NO 1038
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1038
agactgugag agtggugcc 19

<210> SEQ ID NO 1039
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1039
gactgugaga gtggugcct 19

<210> SEQ ID NO 1040
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1040
gacggugacc gtgguccct 19

<210> SEQ ID NO 1041
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1041
aacggugacc gtgguccct 19

<210> SEQ ID NO 1042
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1042
gacagugacc agaguccct 19

<210> SEQ ID NO 1043
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1043
gacggugact gaggtucct 19

<210> SEQ ID NO 1044
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1044
gactgugaga gaggugcct 19

<210> SEQ ID NO 1045
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1045
gactgugaga ctggugcct 19

<210> SEQ ID NO 1046
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1046
ctgaggagac ugtgagagug g 21

<210> SEQ ID NO 1047
<211> LENGTH: 21

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1047
ctgaggagac ggugacugag g 21

<210> SEQ ID NO 1048
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1048
ctgaggagac ugtgagacug g 21

<210> SEQ ID NO 1049
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1049
cugaggagac tgugagagag g 21

<210> SEQ ID NO 1050
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1050
cugcagagac agugaccaga g 21

<210> SEQ ID NO 1051
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

-continued

<400> SEQUENCE: 1051
ctgaggagac ggugaccgug g 21

<210> SEQ ID NO 1052
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1052
ctgaggaaac ggugaccgug g 21

<210> SEQ ID NO 1053
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1053
aaaatttggt 10

<210> SEQ ID NO 1054
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1054
aaaattttta tccccccccg gg 22